US009101539B2

(12) United States Patent
Nagata et al.

(10) Patent No.: US 9,101,539 B2
(45) Date of Patent: Aug. 11, 2015

(54) INTRANASAL PHARMACEUTICAL COMPOSITIONS WITH IMPROVED PHARMACOKINETICS

(75) Inventors: Ryoichi Nagata, Kagoshima (JP); Shunji Haruta, Kagoshima (JP)

(73) Assignee: SHIN NIPPON BIOMEDICAL LABORATORIES, LTD., Kagoshima (JP)

( * ) Notice: Subject to any disclaimer, the term of this patent is extended or adjusted under 35 U.S.C. 154(b) by 0 days.

(21) Appl. No.: 12/780,433

(22) Filed: May 14, 2010

(65) Prior Publication Data

US 2011/0033544 A1 Feb. 10, 2011

Related U.S. Application Data

(60) Provisional application No. 61/178,900, filed on May 15, 2009.

(51) Int. Cl.
*A61K 9/14* (2006.01)
*A61K 9/16* (2006.01)
*C07D 209/10* (2006.01)
*A61K 9/00* (2006.01)

(52) U.S. Cl.
CPC ............. *A61K 9/0043* (2013.01); *A61K 9/1688* (2013.01); *A61K 9/0075* (2013.01)

(58) Field of Classification Search
None
See application file for complete search history.

(56) References Cited

U.S. PATENT DOCUMENTS

| | | | |
|---|---|---|---|
| 3,906,950 A | 9/1975 | Cocozza | |
| 4,013,075 A | 3/1977 | Cocozza | |
| 4,159,345 A | 6/1979 | Takeo et al. | |
| 4,226,233 A | 10/1980 | Kritzer | |
| 4,300,545 A | 11/1981 | Goodnow et al. | |
| 4,613,500 A * | 9/1986 | Suzuki et al. | 424/85.4 |
| 4,889,114 A | 12/1989 | Kladders | |
| 5,098,907 A | 3/1992 | Kondo et al. | |
| 5,320,094 A | 6/1994 | Laube et al. | |
| 5,419,315 A | 5/1995 | Rubsamen | |
| 5,647,349 A | 7/1997 | Ohki et al. | |
| 5,672,581 A | 9/1997 | Rubsamen et al. | |
| 5,674,507 A | 10/1997 | Banker et al. | |
| 5,683,361 A | 11/1997 | Elk et al. | |
| 5,731,303 A | 3/1998 | Hsieh | |
| 5,756,483 A | 5/1998 | Merkus | |
| 5,804,209 A | 9/1998 | De Ponti et al. | |
| 5,810,004 A | 9/1998 | Ohki et al. | |
| 5,939,100 A | 8/1999 | Albrechtsen et al. | |
| 5,942,242 A | 8/1999 | Mizushima et al. | |
| 5,948,749 A | 9/1999 | Igarashi et al. | |
| 5,958,458 A | 9/1999 | Norling et al. | |
| 5,989,217 A | 11/1999 | Ohki et al. | |
| 6,136,295 A | 10/2000 | Edwards et al. | |
| 6,197,328 B1 | 3/2001 | Yanagawa | |
| 6,248,363 B1 | 6/2001 | Patel et al. | |
| 6,273,086 B1 | 8/2001 | Ohki et al. | |
| 6,298,846 B1 | 10/2001 | Ohki et al. | |
| 6,516,795 B1 | 2/2003 | Bougamont et al. | |
| 6,815,424 B2 | 11/2004 | Vickery et al. | |
| 6,824,080 B2 | 11/2004 | Matsugi et al. | |
| 6,835,389 B1 | 12/2004 | Dohi et al. | |
| 6,855,913 B2 | 2/2005 | Nikodym | |
| 6,906,027 B2 | 6/2005 | Oki et al. | |
| 7,022,311 B1 | 4/2006 | Ohkuma et al. | |
| 7,115,281 B2 | 10/2006 | Singh et al. | |
| 7,278,982 B2 | 10/2007 | Tsutsui | |
| 7,306,787 B2 | 12/2007 | Tarara et al. | |
| 7,353,823 B2 | 4/2008 | Tsutsui | |
| 7,638,138 B2 | 12/2009 | Oki et al. | |
| 7,806,117 B2 | 10/2010 | Tsutsui | |
| 8,062,670 B2 | 11/2011 | Baran, Jr. et al. | |
| 2001/0027301 A1 | 10/2001 | Lau et al. | |
| 2001/0038824 A1 | 11/2001 | Horii et al. | |
| 2002/0002172 A1 | 1/2002 | Bell-Huff et al. | |
| 2002/0012688 A1 | 1/2002 | Dohi et al. | |
| 2002/0040139 A1 | 4/2002 | Billotte et al. | |
| 2002/0062829 A1 | 5/2002 | Ohki et al. | |
| 2003/0199424 A1 | 10/2003 | Smith et al. | |
| 2004/0063615 A1 | 4/2004 | Oki et al. | |
| 2004/0076588 A1 | 4/2004 | Batycky et al. | |
| 2004/0092428 A1 | 5/2004 | Chen et al. | |
| 2004/0173211 A1 | 9/2004 | Kladders et al. | |
| 2004/0241232 A1 * | 12/2004 | Brown et al. ................. | 424/469 |
| 2005/0022812 A1 | 2/2005 | Hrkach | |
| 2005/0042177 A1 | 2/2005 | Ryde et al. | |
| 2005/0118272 A1 | 6/2005 | Besse et al. | |
| 2005/0142073 A1 | 6/2005 | Watts et al. | |

(Continued)

FOREIGN PATENT DOCUMENTS

| | | |
|---|---|---|
| EP | 0122036 A1 | 10/1984 |
| EP | 0147755 A2 | 7/1985 |

(Continued)

OTHER PUBLICATIONS

Topliss, John, Quantitative Structure-Activity Relationships of Drugs, 1983, pp. 2.*
Partition Coefficient, Wikipedia, accessed Mar. 31, 2014, pp. 1-8.*
Labiris, N. R. et al., Pulmonary Drug Delivery. Part I: Physiological factors affecting therapeutic effectiveness of aerosolized medications. J CLin Pharmacol, 56, 2003, pp. 588-599.*
Component definition, Dictionary.com, accessed Apr. 1, 2014, pp. 1-4.*

(Continued)

*Primary Examiner* — Scott Long
*Assistant Examiner* — Lyndsey Beckhardt
(74) *Attorney, Agent, or Firm* — Wilson, Sonsini, Goodrich & Rosati, PC

(57) ABSTRACT

Methods are provided for the engineering of inhalable dry powder pharmaceutical formulations with desired pharmacokinetic profiles and parameters. Compositions with improved pharmacokinetics are disclosed.

48 Claims, 13 Drawing Sheets

(56) References Cited

U.S. PATENT DOCUMENTS

| | | |
|---|---|---|
| 2005/0158250 A1 | 7/2005 | Oki et al. |
| 2005/0177095 A1 | 8/2005 | Tsutsui |
| 2005/0232988 A1* | 10/2005 | Venkatesh et al. ............ 424/464 |
| 2006/0057213 A1 | 3/2006 | Larhrib et al. |
| 2006/0106057 A1 | 5/2006 | Daniel et al. |
| 2006/0116657 A1 | 6/2006 | Schmid |
| 2006/0216352 A1 | 9/2006 | Nystrom et al. |
| 2006/0217658 A1 | 9/2006 | Tsutsui |
| 2006/0233715 A1 | 10/2006 | Oki et al. |
| 2007/0055200 A1 | 3/2007 | Gilbert |
| 2007/0060868 A1 | 3/2007 | Tsutsui et al. |
| 2007/0065509 A1* | 3/2007 | Kanikanti et al. ............ 424/464 |
| 2007/0098804 A1 | 5/2007 | Aronhime et al. |
| 2007/0178164 A1 | 8/2007 | Blau |
| 2007/0184109 A1* | 8/2007 | Floyd et al. ................... 424/465 |
| 2007/0249674 A1* | 10/2007 | Bolton et al. ................. 514/317 |
| 2007/0272763 A1 | 11/2007 | Dunne et al. |
| 2008/0029084 A1 | 2/2008 | Costantino et al. |
| 2008/0031959 A1* | 2/2008 | Blondino et al. ............. 424/489 |
| 2008/0090841 A1 | 4/2008 | Johnson et al. |
| 2008/0127972 A1 | 6/2008 | Morton |
| 2008/0260848 A1 | 10/2008 | Nagata et al. |
| 2008/0286362 A1 | 11/2008 | Baran Jr. et al. |
| 2009/0157037 A1 | 6/2009 | Iyer et al. |
| 2009/0169640 A1 | 7/2009 | Oki et al. |
| 2010/0178331 A1 | 7/2010 | Nagata et al. |
| 2011/0045088 A1 | 2/2011 | Tsutsui et al. |

FOREIGN PATENT DOCUMENTS

| | | | |
|---|---|---|---|
| EP | 0761248 A1 | | 3/1997 |
| EP | 0943326 A1 | | 9/1999 |
| EP | 1025859 A1 | | 8/2000 |
| EP | 1108423 A1 | | 6/2001 |
| EP | 1454648 A1 | | 9/2004 |
| EP | 1504780 A1 | | 2/2005 |
| EP | 1785145 A1 | | 5/2007 |
| GB | 2395900 A | | 6/2004 |
| GB | 2448183 | * | 10/2008 |
| JP | 3912469 | | 7/1964 |
| JP | 53127553 | | 11/1978 |
| JP | S 54-20126 A | | 2/1979 |
| JP | 54062328 | | 5/1979 |
| JP | 59-34267 | | 2/1984 |
| JP | 59-34267 A | | 2/1984 |
| JP | S 59-163313 A | | 9/1984 |
| JP | 60-185564 | | 9/1985 |
| JP | 60-224616 | | 11/1985 |
| JP | 62-42888 | | 9/1987 |
| JP | 63267731 | | 11/1988 |
| JP | 3-29146 | | 3/1991 |
| JP | 5-32560 | | 2/1993 |
| JP | 7-165613 A | | 6/1995 |
| JP | 8-098888 | | 4/1996 |
| JP | H 08-206208 A | | 8/1996 |
| JP | 08243164 | | 9/1996 |
| JP | 9-276405 | | 10/1997 |
| JP | 9-291026 A | | 11/1997 |
| JP | 10059841 | | 3/1998 |
| JP | 11/216357 | | 8/1999 |
| JP | 11-322582 | | 11/1999 |
| JP | 2000-229859 A | | 8/2000 |
| JP | 2000-239187 | | 9/2000 |
| JP | 2001-55323 A | | 2/2001 |
| JP | 2002-255795 A | | 9/2002 |
| JP | 2003-154006 A | | 5/2003 |
| JP | 2003-175103 A | | 6/2003 |
| JP | 2003-206227 A | | 7/2003 |
| WO | WO 94/04133 A1 | | 3/1994 |
| WO | WO 95/12399 A1 | | 5/1995 |
| WO | WO 95/34582 A1 | | 12/1995 |
| WO | WO 97/31626 A1 | | 9/1997 |
| WO | WO 98/30207 A1 | | 7/1998 |
| WO | WO 99/16422 A1 | | 4/1999 |
| WO | WO 99/16470 A1 | | 4/1999 |
| WO | WO 99/51205 A1 | | 10/1999 |
| WO | WO 00/12063 A1 | | 3/2000 |
| WO | WO 00/12136 A1 | | 3/2000 |
| WO | WO 00/23023 A1 | | 4/2000 |
| WO | WO 00/38811 A1 | | 7/2000 |
| WO | WO 01/26630 A1 | | 4/2001 |
| WO | WO 01/32125 A2 | | 5/2001 |
| WO | WO 02/32406 A2 | | 4/2002 |
| WO | WO 02/094233 A1 | | 11/2002 |
| WO | WO 03/004048 A1 | | 1/2003 |
| WO | WO 03/030872 A2 | | 4/2003 |
| WO | WO 03/077825 A2 | | 9/2003 |
| WO | WO 03/095008 A1 | | 11/2003 |
| WO | WO 2004/004922 A1 | | 1/2004 |
| WO | WO 2004/073729 A1 | | 9/2004 |
| WO | WO 2005/013937 A2 | | 2/2005 |
| WO | WO 2005/056008 A1 | | 6/2005 |
| WO | WO 2005/104712 A2 | | 11/2005 |
| WO | WO 2006/016530 A1 | | 2/2006 |
| WO | WO 2006/040680 A1 | | 4/2006 |
| WO | WO 2008/031028 A2 | | 3/2008 |
| WO | WO 2008/075102 A1 | | 6/2008 |
| WO | WO 2008/078730 A | | 7/2008 |
| WO | WO 2008/031028 A3 | | 11/2008 |
| WO | WO 2009/095684 | * | 8/2009 |

OTHER PUBLICATIONS

UK combined office action and search report dated Nov. 10, 2010 for Application No. GB1012959.1.
International search report (partial) dated Dec. 21, 2010 for PCT Application No. IB2010/02168.
European search report and opinion dated Dec. 19, 2011 for Application No. 07860016.0.
European search report dated Jul. 15, 2008 for Application No. 05768543.0.
International search report Jun. 8, 2010 for PCT Application No. JP2010/003285.
International search report dated Nov. 1, 2005 for PCT Application No. JP2005/014389.
International search report dated May 7, 2003 for PCT Application No. JP2003/001948.
Kleinebudde, et al. Influence of degree of polymerization on behavior of cellulose during homogenization and extrusion/spheronization. AAPS Pharmasci 2000, 2(2) Article 21, 1-10.
Rowe, et al (Eds). Handbook of Pharmaceutical Excipients. Pharmaceutical Press. 2003. p. 108-109.
U.S. Appl. No. 12/576,219, filed Oct. 8, 2009, Tsutsui et al.
International search report and written opinion dated Jun. 28, 2011 for PCT Application No. IB2010/02168.
Office action dated Sep. 28, 2011 for JP Application No. 2006-531575 (in Japanese with English translation).
UK search report dated Sep. 9, 2011 for Application No. GB1012959.1.
International search report dated Feb. 5, 2008 for PCT Application No. JP2007/074787.
Advisory action dated Sep. 13, 2013 for U.S. Appl. No. 12/848,850.
Office action dated Jan. 13, 2011 for U.S. Appl. No. 12/346,537.
Office action dated Jan. 20, 2011 for U.S. Appl. No. 12/576,219.
Office action dated Jan. 29, 2008 for U.S. Appl. No. 10/545,764.
Office action dated Mar. 4, 2013 for U.S. Appl. No. 12/848,850.
Office action dated Apr. 12, 2012 for U.S. Appl. No. 12/576,219.
Office action dated Jun. 4, 2012 for U.S. Appl. No. 12/521,116.
Office action dated Jun. 25, 2012 for U.S. Appl. No. 12/346,537.
Office action dated Sep. 6, 2011 for U.S. Appl. No. 12/346,537.
Office action dated Sep. 6, 2011 for U.S. Appl. No. 12/576,219.
Office action dated Sep. 24, 2008 for U.S. Appl. No. 10/545,764.
Office action dated Sep. 27, 2010 for U.S. Appl. No. 11/660,131.
Office action dated Oct. 15, 2012 for U.S. Appl. No. 12/848,850.
Office action dated Oct. 29, 2009 for U.S. Appl. No. 11/660,131.
Office action dated Nov. 1, 2012 for U.S. Appl. No. 11/660,131.
Office action dated Dec. 5, 2011 for U.S. Appl. No. 12/346,537.
Nagata, et al. U.S. Appl. No. 13/649,515, titled Preparation for Transnasal Application, filed Oct. 11, 2012.

(56) References Cited

OTHER PUBLICATIONS

"Fluorouracil" definition viewed on the National Cancer Institute website at www.cancergov/drugdictionary?cdrid=43130 on May 31, 2012.

Hens, et al., "BMP4 and PTHrP interact to stimulate ductal outgrowth during embryonic mammary development and to inhibit hair follicle induction," Development 2007, 234, pp. 1221-1230.

Merriam-Webster's Collegiate Dictionary, 10th edition, Merriam-Webster Incorporated: Springfield, Massachusetts, 1993, pp. 41.

Office action dated Sep. 20, 2013 for U.S. Appl. No. 13/827,859.

U.S. Appl. No. 13/827,859, filed Mar. 14, 2014, Oki et al.

Hibberd, et al. Immunization strategies for the immunocompromised host: the need for immunoadjuvants. Ann Intern Med. Jun. 15, 1989;110(12):955-6.

Ishikawa, et al. Improved nasal bioavailability of elcatonin by insoluble powder formulation. Int J Pharm. Aug. 14, 2001;224(1-2):105-14.

Office action dated May 7, 2013 for U.S. Appl. No. 11/660,131.

Office action dated Jun. 10, 2013 for U.S. Appl. No. 12/576,219.

European search report and opinion mailed Dec. 20, 2013 for Application No. 10774745.3.

Office action dated Jan. 6, 2014 for U.S. Appl. No. 12/576,219.

Office action dated Apr. 8, 2014 for U.S. Appl. No. 13/827,859.

Notice of allowance dated Sep. 24, 2014 for U.S. Appl. No. 12/576,219.

Notice of allowance dated Nov. 5, 2014 for U.S. Appl. No. 13/827,859.

Office action dated Nov. 24, 2014 for U.S. Appl. No. 13/649,515.

Office action dated Apr. 2, 2015 for U.S. Appl. No. 13/649,515.

\* cited by examiner

INTRANASAL PHARMACEUTICAL COMPOSITIONS WITH IMPROVED PHARMACOKINETICS

CROSS-REFERENCE

This application claims the benefit of priority under 35 U.S.C. §119(e) to U.S. Provisional Application No. 61/178,900, filed May 15, 2009, which application is incorporated herein by reference in its entirety for all purposes.

BACKGROUND OF THE INVENTION

Inhalation is a convenient administration route for therapeutic agents that overcomes many of the drawbacks of oral administration, such as slow drug onset and first-pass metabolism plus it can be used with patients that suffer from nausea, emesis, or dysphagia. Inhalation of a salt form of a therapeutic agent usually produces rapid systemic adsorption exemplified by an early, high peak in plasma concentration that then drops off rapidly over time. In many situations, such a pharmacokinetic profile is desirable, but in other instances, a different pharmaceutical profile would better fit the clinical need. For instance, with migraines sufferers, an ideal pharmaceutical composition would provide fast initial relief of symptoms by producing an early high peak in plasma concentration and that additionally maintains a relatively high plasma concentration over time to prevent relapse. A pharmaceutical composition with this pharmacokinetic profile would represent an important therapeutic breakthrough for the treatment of migraines. Similarly, other indications such as emesis would benefit from the ability to tailor the pharmacokinetic profile of an inhalable therapeutic agent.

There exists a need to be able to engineer inhalable pharmaceutical formulations so that the pharmacokinetic profiles more closely fit clinical requirements. The discovery that pharmacokinetic profiles can be engineered based on the careful selection of the chemical and physical properties of inhalable particles meets this need.

INCORPORATION BY REFERENCE

All publications, patents, and patent applications mentioned in this specification are herein incorporated by reference in their entirety as if each individual publication, patent, or patent application was specifically and individually indicated to be incorporated by reference.

SUMMARY OF THE INVENTION

The present disclosure provides compositions comprising inhalable dry powder pharmaceutical formulations, methods of making the formulations and methods of using the formulations. One formulation disclosed herein is an inhalable dry powder pharmaceutical formulation comprising a therapeutic agent wherein at least some of the therapeutic agent is present in a freebase form, wherein, the therapeutic agent comprises particles having a particle size distribution between about 5 µm to about 250 µm. The formulation can further comprise a salt form of the therapeutic agent. The particle size distribution of the therapeutic agent can be between about 15 µm to about 200 µm, between about 20 µm to about 150 µm, between about 38 µm to about 100 µm, or between about 53 µm to about 150 µm. In some instances, the composition further comprises a carrier and the carrier can be substantially water-soluble or a substantially water-insoluble. Examples of carriers include polysaccharides, sugars, salts, polymers, gums, proteins, and carbohydrates. In some instances, the carrier is a bioadhesive. Polysaccharide carriers can comprise native, derivatized, and/or modified forms of a polysaccharide. The polysaccharide can be a starch, such as hydroxypropyl starch, carboxymethyl starch, cross-linked starch, amylose, amylopectin, or pectin. A polysaccharide can also be cellulose, such as crystalline cellulose, cellulose, α-cellulose, methylcellulose, hydroxypropyl cellulose, carboxymethyl cellulose, and hydroxypropyl methyl cellulose. A useful crystalline cellulose can have a particle diameter range from about 5 to 250 µm a bulk density of less than 0.60 g/cm$^3$, and/or an average degree of polymerization of about 20 to about 250. Formulations disclosed herein can also comprise an additional therapeutic agent, which can be a salt of the agent, a freebase of the agent, or a mixture thereof. Sugars used in formulations disclosed herein can comprise fructose, galactose, glucose, lactitol, lactose, maltitol, maltose, mannitol, melezitose, myoinositol, palatinite, raffinose, stachyose, sucrose, trehalose, xylitol, hydrates thereof, or combinations thereof. Compositions disclosed herein can also comprise a lubricant, surfactant, acidifying agent, alkalizing agent, antimicrobial preservative, antioxidant, buffering agent, chelating agent, complexing agent, solubilizing agent, humectant, or wetting agent. One example of a fluidizer is tribasic calcium phosphate.

Also disclosed herein are inhalable dry powder pharmaceutical formulations comprising a therapeutic agent wherein at least some of which is present in a freebase form, and wherein the formulation has a water-octanol Log D 7.4 of between about 0 and about 5. In some instances the water-octanol Log D 7.4 of formulations disclosed herein is between about 1 and about 4, or between about 2 and about 4. Still other formulations have a water-octanol Log D 7.4 between about 2 and about 4, and the salt and freebase forms of the therapeutic agent individually comprise a water-octanol Log D 7.4 of less than 2 or greater than 4.

Still other formulations disclosed herein are inhalable dry powder pharmaceutical formulations comprising a therapeutic agent wherein at least some of the agent is present in a freebase form, and wherein the formulation has a water-octanol Log P of between about 0 and about 5, between about 1 and about 4, or between about 2 and about 4. Still other formulations have a water-octanol Log P of between about 2 and about 4, and wherein the salt and freebase forms of the therapeutic agent individually comprise a water-octanol Log P of less than 2 or greater than 4.

Yet another formulation disclosed herein is an inhalable dry powder pharmaceutical formulation comprising a therapeutic agent, wherein the therapeutic agent is present at a ratio of salt to freebase form that is equal to or greater than 1:2 on a molar basis, equal to or greater than 1:5 on a molar basis, or equal to or greater than 1:10 on a molar basis. Formulations can comprise the freebase form of the therapeutic agent with a particle size distribution between about 5 µm to about 250 µm, between about 15 µm to about 200 µm, between about 20 µm to about 150 µm, between about 38 µm to about 100 µm, or between about 53 µm to about 150 µm. In some embodiments, the freebase form of the therapeutic agent has a particle size distribution greater than about 100 µm.

Still another formulation disclosed herein is a pharmaceutical formulation comprising a therapeutic agent wherein at least some of therapeutic agent is present in a freebase form, and wherein following intranasal administration to a human, the taste profile is substantially less bitter or objectionable compared to the taste profile of an otherwise identical pharmaceutical formulation wherein the therapeutic agent is present as a salt form at the same molar quantity.

Also provided herein are unit dosages of any of the formulations disclosed herein. Such dosages can be any form, such as a capsule (e.g., a hydroxypropyl methylcellulose capsule). Unit dosages can also be in the form of an intranasal administration device. Devices can be disposable.

Further provided herein is an inhalable dry powder pharmaceutical formulation comprising a therapeutic agent wherein at least some of the therapeutic agent is present in a freebase form, wherein the maximal blood therapeutic concentration (Cmax) of the therapeutic agent in the pharmaceutical formulation is at least 60% of the Cmax compared to the therapeutic agent when present at 100% salt form at the same molar quantity in an otherwise identical pharmaceutical formulation when administered to a primate. In some instances, the formulation has a Cmax that is at least 80%, at least 90%, at least 95%, at least 100%, at least 110%, at least 125% or at least 150% compared to the Cmax of the therapeutic agent when present at 100% salt form at the same molar quantity in an otherwise identical pharmaceutical formulation when administered to a primate.

Another formulation provided herein is an inhalable dry powder pharmaceutical formulation comprising a therapeutic agent wherein at least some of the therapeutic agent is present in a freebase form, wherein the time to reach a blood concentration of ½ of Cmax($T_{1/2}$) of the therapeutic agent in the pharmaceutical formulation is at least 60%, at least 80%, at least 90%, at least 95%, at least 100%, at least 110%, at least 115%, at least 125%, or at least 150% of the $T_{1/2}$ compared to the therapeutic agent when present at 100% salt form at the same molar quantity in an otherwise identical pharmaceutical formulation when administered to a primate.

Still another formulation provided herein is an inhalable dry powder pharmaceutical formulation comprising a therapeutic agent wherein at least some of therapeutic agent is present in a freebase form, wherein the time to reach a blood concentration Cmax(Tmax) of the therapeutic agent in the pharmaceutical formulation is at least 60%, at least 80%, at least 90%, at least 95%, at least 100%, at least 110%, at least 115%, at least 125%, or at least 150% of the Tmax compared to the therapeutic agent when present at 100% salt form at the same molar quantity in an otherwise identical pharmaceutical formulation when administered to a primate.

Also provided herein is an inhalable dry powder pharmaceutical formulation comprising a therapeutic agent wherein at least some of the therapeutic agent is present in a freebase form, wherein the bioavailability (BA) of the therapeutic agent in the pharmaceutical formulation is at least 60%, at least 80%, at least 90%, at least 95%, at least 100%, at least 110%, at least 115%, at least 125%, or at least 150% of the BA compared to the therapeutic agent when present at 100% salt form at the same molar quantity in an otherwise identical pharmaceutical formulation when administered to a primate.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
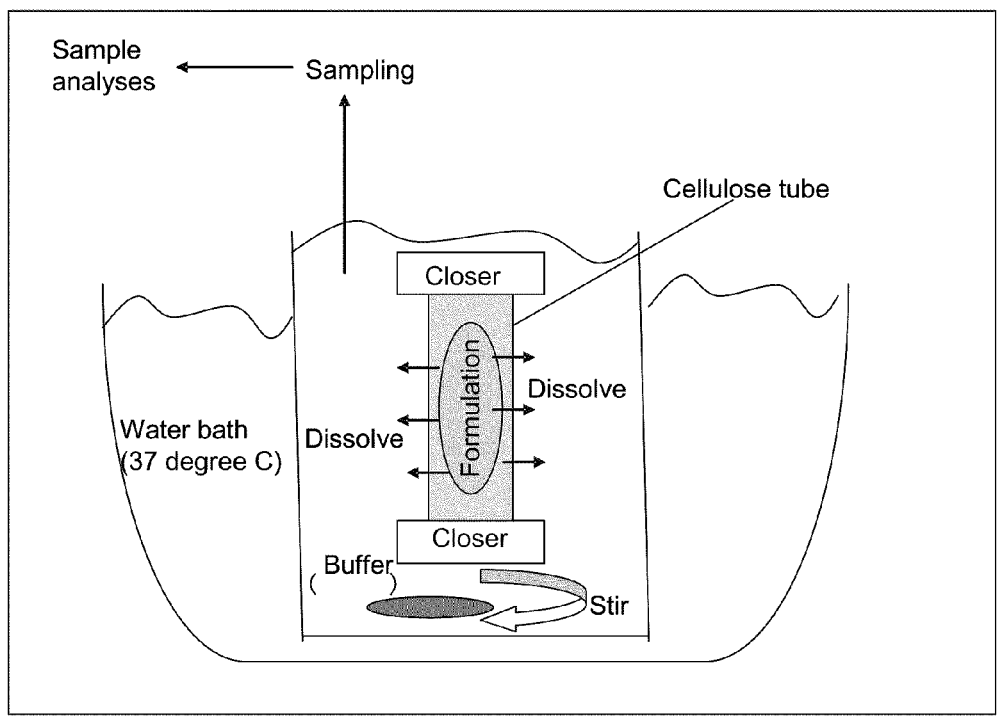
FIG. 1 is a representative apparatus used in the measurement of dry powder formulation dissolution rates.

Provided in the present disclosure are pharmaceutical compositions comprising therapeutic agents which can be in a freebase form, a salt form or a combination of the two forms. The pharmaceutical compositions are typically inhalable dry powders with particle size ranges sufficient for inhalation. In some instances, other components, such as carriers, sugars, polysaccharides, flowability agents and other components. Particle size of therapeutic agents can differ from the particle size of a mixture of the one or more therapeutic agents and the carrier(s), sugars, flowability agents, etc. Additionally, such compositions can be constructed so as to achieve a desired pharmacokinetic outcome. For example, the treatment of migraine headaches can encompass the production of a unit dose which provides rapid treatment for the symptoms of migraine (e.g., pain relief) as well as long-term treatment and/or prophylaxis of migraine symptoms. Disclosed herein are compositions and methods of producing the compositions which allow for improved pharmacokinetics.

DEFINITIONS

To facilitate an understanding of the present invention, the following terms are defined below. Unless defined otherwise, all technical and scientific terms used herein have the same meaning as is commonly understood in the field to which the claimed subject matter belongs. In the event that there is a plurality of definitions for terms herein, those in this section prevail.

Recitation of a range of values herein refers individually to each separate value falling within the range as if it were individually recited herein, whether or not some of the values within the range are expressly recited. Specific values employed herein will be understood as exemplary and not to limit the scope of the invention.

The disclosed techniques and procedures are generally performed of conventional methods and as described in various general and more specific references that are cited and discussed throughout the present specification.

It is to be understood that the methods and compositions described herein are not limited to the particular methodology, protocols, cell lines, therapeutic agents, and reagents described herein and as such may vary. It is also to be understood that the terminology used herein is for the purpose of describing particular embodiments only, and is not intended to limit the scope of the methods, compounds, compositions described herein.

The section headings used herein are for organizational purposes only and are not to be construed as limiting the subject matter described.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

The terms "kit" and "article of manufacture" can be synonyms.

The term "subject" or "patient" encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

The terms "treat," "treating" or "treatment," as used herein, include alleviating, abating or ameliorating a disease, disorder or condition symptoms, preventing additional symptoms, ameliorating or preventing the underlying causes of symptoms, inhibiting the disease, disorder or condition, e.g., arresting the development of the disease, disorder or condition, relieving the disease, disorder or condition, causing regression of the disease, disorder or condition, relieving a condition caused by the disease, disorder or condition, or stopping the symptoms of the disease, disorder or condition either prophylactically and/or therapeutically.

The terms "therapeutic agent", "active ingredient", "physiologically active substance", "therapeutic agent", "therapeutic compound", "drug" or the like, as used herein refers to a material that is administered to a subject to treat or ameliorate the symptoms of a disease, disorder, or condition. A therapeutic agent is not particularly limited, and includes drugs with systemic or local effects, vaccines, prodrugs and other derivatives, salts, or the like.

The terms "small molecule", "low molecular weight molecule", and the like as used herein refer to a small organic compound that is biologically active. The term small molecule encompasses primary and secondary metabolites. Small molecules include naturally occurring compounds like caffeine and morphine and also semi-synthetic or synthetic compounds such as fentanyl.

The terms "peptide", "oligopeptide", "protein" and the like as used herein refer to biologically active molecules that are polypeptides or polymers of amino acids. Peptides, oligopeptides and protein represent a continuum of polypeptides that become increasingly longer from peptides to oligopeptides to proteins. Peptides are generally thought of comprising of short chains of amino acids or fragments of molecules or proteins while proteins are generally longer chains of amino acids that include a complete, intact, or whole molecules.

Generally peptides have molecular weights on the order of about 100 to about 50,000 daltons. In one embodiment the peptides used in the present invention have molecular weights on the order of about 100 to about 30,000 daltons, though other peptides, which, due to their coiling may be larger than 30,000 daltons, are also within the scope of the invention.

Peptides include molecules with modifications or replacements to the native sequence as described in U.S. Pat. No. 6,784,157. For instance naturally occurring L-amino amino acids can be replaced with the D-amino acids, or with unnatural amino acids, such as replacing serine with isoserine. Additionally, cyclic structures can be incorporated into the backbone to rigidify the molecule or the C- or N-terminus can be chemically modified. Furthermore, deletions or additions can be made to the native amino acid sequence.

The term peptide also encompasses peptide mimetics or "peptidomimetics"; molecules that mimic the biological activity of peptides but are no longer wholly or partially peptidic in chemical nature. In other words, peptidomimetics may contain no peptide bonds (that is, amide bonds between amino acids) or they may contain substantially less peptide bonds compared to the native molecules. The term peptidomimetic includes pseudo-peptides, semi-peptides and peptoids. Whether completely or partially non-peptide, peptidomimetics provide a spatial arrangement of reactive chemical moieties that closely resembles the three-dimensional arrangement of active groups in the peptide on which the peptidomimetic is based. As a result of this similar active-site geometry, the peptidomimetic has effects on biological systems which are similar to the biological activity of the peptide.

Although the present invention will be described initially with respect to inhalable compositions and methods of use of pharmaceutically active peptides, it should be understood, however, that the present invention encompasses inhalable compositions and methods of use for peptidomimetics and/or proteins.

As used herein, amelioration of the symptoms of a particular disease, disorder or condition by administration of a particular therapeutic agent or pharmaceutical composition refers to any lessening of severity, delay in onset, slowing of progression, or shortening of duration, whether permanent or temporary, lasting or transient that are attributed to or associated with administration of the therapeutic agent or composition.

The term "acceptable" with respect to a formulation, composition or ingredient, as used herein, means having no persistent detrimental effect on the general health of the subject being treated.

By "pharmaceutically acceptable," as used herein, refers a material, such as a carrier or excipient, which does not abrogate the biological activity or properties of the compound, and is relatively nontoxic, i.e., the material is administered to an individual without causing undesirable biological effects or interacting in a deleterious manner with any of the components of the composition in which it is contained.

The terms "co-administration" or the like, as used herein, are meant to encompass administration of the selected therapeutic agents to a single patient, and are intended to include treatment regimens in which the agents are administered by the same or different route of administration or at the same or different time. Co-administration encompasses the simultaneous delivery of two or more agents in the form of a single entity, dose, or dosage unit.

The term "pharmaceutical composition" refers to a mixture of a therapeutic agent described herein with other chemical components including a carrier and/or excipients such fluidizers, lubricants, preservatives, surfactants, antistatic agents, anti-microbial agents and the like. The pharmaceutical composition can facilitate administration of antherapeutic agent to an organism.

In some embodiments, a prodrug is administered with or without the therapeutic agent. A "prodrug" refers to an agent that is converted into the therapeutic agent in vivo. In other words, the therapeutic agent is released from or is generated from the prodrug. In one embodiment, the therapeutic agent is a metabolite of the prodrug. The term metabolism includes reactions such as the hydrolysis of esters, phosphates and other labile chemical bonds that occur within or outside of cells. Prodrugs are often useful because they have properties that are more conducive for administration of therapy. For instance, the prodrug may have better processing properties in terms of creating appropriate sized particles, better flowability, or better stability in storage. Additionally, the prodrug may have improved solubility over the therapeutic agent or a more desirable diffusion or partitioning coefficient that results in a greater bioavailable of the prodrug compared to the therapeutic agent.

The terms "effective amount", pharmacologically effective amount", "physiologically effective amount" or "therapeutically effective amount," as used herein, refer to a sufficient amount of a therapeutic agent or a compound being administered which will relieve to some extent one or more of the symptoms of the disease or condition being treated. The result is reduction and/or alleviation of the signs, symptoms, or causes of a disease, or any other desired alteration of a biological system. For example, an "effective amount" for therapeutic uses is the amount of the composition that includes a therapeutic agent herein required to provide a desired level of therapeutic agent in the bloodstream or at the site of action (e.g., the sinuses, or the lung tissue) of a subject to be treated and thereby produce a clinically significant decrease in disease symptoms. The precise amount will depend upon numerous factors, e.g., the specific therapeutic agent, the activity of the therapeutic agent, the delivery device employed, the physical characteristics of the therapeutic agent, intended use by the subject (i.e., the number of doses administered per day), subject considerations, and the like, and can readily be determined by one skilled in the art, based upon the information provided herein. In some embodiments, an appropriate "effective" amount in any individual case is determined using techniques, such as a dose escalation study.

The terms "pharmaceutically acceptable salt" or "salt" includes, but is not limited to: (1) acid addition salts, formed by reacting the freebase form of a therapeutic agent with a pharmaceutically acceptable: inorganic acid, such as, for example, hydrochloric acid, hydrobromic acid, sulfuric acid, phosphoric acid, metaphosphoric acid, and the like; or with an organic acid, such as, for example, acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, butyric acid, phenylacetic acid, phenylbutyric acid, valproic acid, and the like; (2) salts formed when an acidic proton present in the parent therapeutic agent is replaced by a metal ion, e.g., an alkali metal ion (e.g. lithium, sodium, potassium), an alkaline earth ion (e.g. magnesium, or calcium), or an aluminum ion. In some cases, therapeutic agents may coordinate with an organic base, such as, but not limited to, ethanolamine, diethanolamine, triethanolamine, tromethamine, N-methylglucamine, dicyclohexylamine, tris(hydroxymethyl)methylamine. In other cases, therapeutic agents form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, sodium hydroxide, and the like.

It should be understood that a reference to a pharmaceutically acceptable salt includes the solvent addition forms or crystal forms thereof, particularly solvates or polymorphs. Solvates contain either stoichiometric or non-stoichiometric amounts of a solvent, and in some embodiments are formed during the process of crystallization with pharmaceutically acceptable solvents such as water, ethanol, and the like. Hydrates are formed when the solvent is water, or alcoholates are formed when the solvent is alcohol. In other embodiments the therapeutic agents exist in unsolvated as well as solvated forms. In general, the solvated forms are considered equivalent to the unsolvated forms for the purposes of the compositions, formulations and methods provided herein.

The term "freebase" includes, but is not limited to, the unprotonated amine form of a therapeuticagent, molecule, or compound. Additionally, "freebase" includes, but is not limited to, the neutral form of a molecule or compound. Freebases are not salts of an agent, molecule or compound and they generally have reduced solubility in polar solvents such as water compared to the salt forms of an agent, molecule or compound.

The term "freebase equivalent weight" means that the salt form of a therapeutic agent is being compared or analyzed based on the weight of the therapeutic agent if the quantity of the salt form of the agent present was converted to the weight of its freebase. In other words, the molar quantity of the drug present remains the same, but for calculations or comparative purposes, the salt form of the drug is converted to the weight of a corresponding equivalent molar quantity of the freebase.

"Bioavailability" refers to the percentage of the weight of a therapeutic agent that is delivered into the general circulation of the animal or human being studied. The total exposure (AUC(0-∞)) of a drug when administered intravenously is usually defined as 100% bioavailable. "Intranasal bioavailability" refers to the extent to which a therapeutic agent is absorbed into the general circulation when the pharmaceutical composition is taken intranasally as compared to intravenous injection. "Pulmonary bioavailability" refers to the extent to which a therapeutic agent is absorbed into the general circulation when the pharmaceutical composition is taken by pulmonary administration as compared to intravenous injection.

"Blood plasma concentration", "blood concentration", "plasma concentration" or "serum concentration" refers to the concentration of a therapeuticagent in the plasma or serum component of blood of a subject. It is understood that the plasma or serum concentration of therapeutic agents may vary significantly between subjects, due to variability with respect to metabolism and/or possible interactions with other therapeutic agents. In accordance with one embodiment disclosed herein, the plasma or serum concentration of the therapeutic agents disclosed herein varies from subject to subject. Likewise, in some embodiments, values such as maximum plasma concentration ($C_{max}$) or time to reach maximum plasma concentration ($T_{max}$), or total area under the plasma concentration time curve (AUC(0-∞)) varies from subject to subject. Due to this variability, the amount necessary to constitute "a therapeutically effective amount" of a compound will vary from subject to subject.

Particle Size of Therapeutic Agents, Carriers and Excipients

The particle size distribution range of therapeutic agents, carriers, excipients and other components used in a formulation can be measured in a number of ways including sieving and laser diffraction. Generally, sieving analysis is carried out by stacking a set of sieves in ascending order of aperture size and placing the sample to be analyzed of the top sieve. A closed pan (receiver) is placed at the bottom of the stack to collect the fines and a lid is placed on top of the stack of sieves to prevent loss of particles. The stack is vibrated for a fixed amount of time and the residual weight of particles on each sieve determined. Sieve results can be highly reproducible (within 5%). A vacuum can be drawn across the sieves to increase the rate and amount of material that crosses the individual sieves. All sieving values reported herein were obtained without the use of a vacuum, unless specifically noted otherwise.

Laser diffraction depends on the analysis of the "halo" of diffracted light produced when a laser beam passes through a dispersion of particles. The angle of diffraction increases as particle size decreases, so that this method is particularly good for measuring sizes below 5 µm.

In one aspect, the invention comprises an inhalable dry powder pharmaceutical formulation comprising a therapeutic agent, wherein the therapeutic agent is present as a freebase or as a mixture of a salt and a freebase. Pharmaceutical formulations disclosed herein can be formulated as suitable for airway administration, for example, nasal, intranasal, sinusoidal, peroral, and/or pulmonary administration. Typically, formulations are produced such that they have an appropriate particle size for the route, or target, of airway administration. As such, the formulations disclosed herein can be produced so as to be of defined particle size distribution.

For example, the particle size distribution for a salt form of a therapeutic agent for intranasal administration can be between about 5 µm and about 350 µm. More particularly, the salt form of the therapeutic agent can have a particle size distribution for intranasal administration between about 5µ to about 250 µm, about 10 µm to about 200 µm, about 15 µm to about 150 µm, about 20 µm to about 100 µm, about 38 µm to about 100 µm, about 53 µm to about 100, about 53 µm to about 150 µm, or about 20 µm to about 53 µm. The salt form of the therapeutic agent in the pharmaceutical compositions of the invention can a particle size distribution range for intranasal administration that is less than about 200 µm. In other embodiments, the salt form of the therapeutic agent in the pharmaceutical compositions has a particle size distribution that is less than about 150 µm, less than about 100 µm, less than about 53 µm, less than about 38 µm, less than about 20 µm, less than about 10 µm, or less than about 5 µm. The salt form of the therapeutic agent in the pharmaceutical compositions of the invention can have a particle size distribution range for intranasal administration that is greater than about 5 µm, greater than about 10 µm, greater than about 15 µm, greater than about 20 µm, greater than about 38 µm, less than about 53 µm, less than about 70 µm, greater than about 100 µm, or greater than about 150 µm.

Additionally, the salt form of the therapeutic agent in the pharmaceutical compositions of the invention can have a particle size distribution range for pulmonary administration between about 1 µm and about 10 µm. In other embodiments for pulmonary administration, particle size distribution range is between about 1 µm and about 5 µm, or about 2 µm and about 5 µm. In other embodiments, the salt form of the therapeutic agent has a mean particle size of at least 1 µm, at least 2 µm, at least 3 µm, at least 4 µm, at least 5 µm, at least 10 µm, at least 20 µm, at least 25 µm, at least 30 µm, at least 40 µm, at least 50 µm, at least 60 µm, at least 70 µm, at least 80 µm, at least 90 µm, or at least 100 µm.

As described herein, pharmaceutical compositions of the present invention can comprise freebase forms of therapeutic agents, alone or in combination with salt forms of the same therapeutic agent. Additionally, pharmaceutical compositions comprising the salt and/or freebase form of one therapeutic agent can also comprise the salt and/or freebase form of one or more additional therapeutic agents. Like the salt forms, freebase forms useful in the present compositions can also have defined particle size distribution. This distribution can be the same as or different from the size distribution of the freebase form. For example, the particle size distribution range of a freebase form of a therapeutic agent for intranasal administration can be between about 5 µm and about 350 µm, between about 5µ to about 250 µm, about 10 µm to about 200 µm, about 15 µm to about 150 µm, about 20 µm to about 100 µm, about 38 µm to about 100 µm, about 53 µm to about 100, about 53 µm to about 150 µm, or about 20 µm to about 53 µm. In some embodiments, the freebase form of the therapeutic agent in the pharmaceutical compositions of the invention has a particle size distribution range for intranasal administration that is less than about 200 µm, less than about 150 µm, less than about 100 µm, less than about 53 µm, less than about 38 µm, or less than about 20 µm. In some embodiments, the freebase form of the therapeutic agent in the pharmaceutical compositions has a particle size distribution for pulmonary administration of less than about 20 µm, less than about 10 µm, or less than about 5 µm.

Freebase form of the therapeutic agent in the pharmaceutical compositions of the invention can have a particle size distribution range for intranasal administration that is greater than about 5 µm, greater than about 10 µm, greater than about 15 µm, greater than about 20 µm, greater than about 38 µm, less than about 53 µm, less than about 70 µm, greater than about 100 µm, or greater than about 150 µm.

In some embodiments, the freebase form of the therapeutic agent in the pharmaceutical compositions of the invention has a particle size distribution range for pulmonary administration between about 1 µm and about 10 µm. In other embodiments for pulmonary administration, particle size distribution range is between about 1 µm and about 5 µm, or about 2 µm and about 5 µm. In other embodiments, the freebase form of the therapeutic agent has a mean particle size of at least 1 µm, at least 2 µm, at least 3 µm, at least 4 µm, at least 5 µm, or at least 10 µm.

In some embodiments, the freebase form of the therapeutic agent has a mean particle size for intranasal administration of at least 10 µm. In other embodiments, the freebase form of the therapeutic agent has a mean particle size of at least 5 µm, at least 15 µm, at least 20 µm, at least 25 µm, at least 30 µm, at least 40 µm, at least 50 µm, at least 60 µm, at least 70 µm, at least 80 µm, at least 90 µm, or at least 100 µm.

Particle size distributions and the mean particle size for therapeutic agents, carriers and excipients can be determined by any method known in the art, for example, by sieving. Alternately, the therapeutic agents, carriers, excipients and other formulation components can be used as produced, without sieving, if the production process produces an acceptable particle size distribution, such as spray drying or milling. Alternatively, in other embodiments, materials can be separated into appropriate sized fractions using sieving or other suitable means prior to formulating the pharmaceutical compositions.

Pharmaceutical Compositions

Freebase-Particle Size

Pharmaceutical compositions are provided wherein the compositions can comprise of a therapeutic agent in freebase form with particles in a single particle size distribution range. Generally, it was discovered that with intranasal freebase compositions, the smaller the particle size of the therapeutic agent, the higher the observed Cmax and the shorter the observed Tmax. Thus, freebase compositions can be engineered based on the particle size of the therapeutic agent so that the pharmacokinetic profiles are substantially similar to the pharmacokinetic profile seen with identical compositions comprising the salt form that has the same freebase equivalent weight. Generally, pharmacokinetic profiles can be engineered so that a freebase formulation has one or more pharmacokinetic parameters that are ±5%, ±10%, ±20%, ±30%, or ±40% of the corresponding one or more pharmacokinetic parameters of a salt formulation. Typically, freebase particles with a size distribution range of about 5 µm to about 38 µm, about 10 µm to about 38 µm, or about 10 µm to about 20 µm administered intranasally produce pharmacokinetic profiles that may be substantially similar or have pharmacokinetic parameters that are within ±5%, ±10%, ±20%, ±30%, or ±40% of pharmacokinetic profiles seen with intranasally administered salt forms of a therapeutic agent. By substantially similar, in this aspect, is meant±1%. In some embodiments, intranasal pharmaceutical formulations are provided that have a Cmax that is within ±5%, ±10%, ±20%, ±30%, or ±40% of the Cmax seen of an otherwise identical formulation where the freebase is replaced with a salt form of a therapeutic agent at the same molar quantity. In some embodiments, intranasal pharmaceutical formulations are provided that have a Tmax that is within ±5%, ±10%, ±20%, ±30%, or ±40% of the Tmax seen with an otherwise identical formulation where the freebase is replaced with a salt form of a therapeutic agent at the same molar quantity. In some embodiments, intranasal pharmaceutical formulations are provided that have a T½ that is within ±5%, ±10%, ±20%, ±30%, or ±40% of the T½ seen with an otherwise identical formulation where the freebase is replaced with a salt form of a therapeutic agent at the same molar quantity.

Conversely, it was discovered that generally, as the freebase particle size increases, the pharmacokinetic parameters change compared to pharmacokinetic profiles seen with intranasally administered salt forms of a therapeutic agent. Generally, the Cmax decreases, the Tmax may increase and the $T_{1/2}$ may increase. In some embodiments, intranasal pharmaceutical formulations of freebase therapeutic agents are provide that have a Cmax that is no more than about 90%, 80%, 60%, 40%, 20%, or 10% of the Cmax of an identical intranasal pharmaceutical formulation where the therapeutic agent is a salt form at the same molar quantity. In some embodiments, intranasal pharmaceutical formulations of freebase therapeutic agents are provide that have a Tmax that is at least about 110%, 125%, 150%, 200%, 300%, or 400% of the Tmax of an identical intranasal pharmaceutical formulation where the therapeutic agent is a salt form at the same molar quantity. In some embodiments, intranasal pharmaceutical formulations of freebase therapeutic agents are provide that have a $T_{1/2}$ that is at least about 110%, 120%, 140%, 160%, 200%, or 400% of the $T_{1/2}$ of an identical intranasal pharmaceutical formulation where the therapeutic agent is a salt form at the same molar quantity.

Knowledge of the ability to change the pharmacokinetics of freebase therapeutics based on the particle size allows one to engineer intranasal formulations with desired pharmacokinetic parameters by using an appropriate size particle distribution range, or by formulating a mixture of two or more particle distribution ranges. For example, the inhalable pharmaceutical composition can have one size distribution of freebase of about 10 µm to about 20 µm and another size distribution of freebase of about 50 µm to about 10 µm. In this way, a Cmax that is substantially similar to a salt form is achieved primarily through the use of the smaller particle size distribution range, while a $T_{1/2}$ longer than that of the salt form is reached primarily through the contribution of the larger particle size distribution of freebase. For example, a formulation of sumatriptan for migraines can have particles of different size distributions to effect an immediate treatment and a longer-term treatment/prophylactic effect.

Mixtures of Freebase and Salt

In one aspect of the invention, dry powder pharmaceutical formulations suitable for intranasal administration are provided that comprise of a mixture of a freebase and a salt form of a therapeutic agent. It was discovered that intranasal dry powder formulations with desired pharmacokinetic profiles for can be engineered by incorporating freebase and salt forms of the therapeutic agent in the formulations. Generally, freebase forms of therapeutic agents are absorbed more slowly than salt forms of the therapeutic agent of the same size distribution. Typically, by providing an intranasal formulation with a mixture of a salt form and a freebase form of a therapeutic agent an initial, high blood concentration of the therapeutic agent can be provided predominately by the salt form, while later blood concentration will be provided chiefly by the freebase form.

The absorption rate for freebase forms of therapeutic agents can be adjusted by changing the particle size distribution with, generally, smaller size particle having a faster absorption than larger size particles. Typically, freebase therapeutic agents with small particle size distribution ranges produce a higher Cmax and/or shorter Tmax compared to larger particle size distribution ranges for the same freebase therapeutic agents. Through careful analysis and testing, intranasal formulations of freebase and salt forms of a therapeutic agent can be designed that have pharmacokinetic profiles and parameters that are improved over what is currently achieved with intranasal dry powder formulations that contain only a salt form of a therapeutic agent. Depending on the application, pharmaceutical formulations with lower, higher or equivalent Cmax, Tmax, $T_{1/2}$, or BA can be designed based on the discoveries disclosed herein. For example, a formulation can have a smaller particle size for the freebase and a larger particle size for the salt form, roughly equivalent sizes, or a smaller particle size for the salt form and a larger particle size for the freebase, depending on the pharmacokinetic profile desired for a particular formulation.

In some embodiments, the pharmacokinetic profiles of freebase and salt formulation mixtures have pharmacokinetic profiles where one or more pharmacokinetic parameters are improved compared to the pharmacokinetic parameters seen with an identical formulation made with an equal molar quantity of a salt form of the therapeutic agent. In some embodiments, the Cmax of a freebase and salt mixture formulation is equivalent or within ±5%, ±10%, ±20%, ±30%, or ±40% of the corresponding Cmax of a salt formulation, but the Tmax is at least 10%, 20%, 40%, 60%, 80%, or 100% longer than the Tmax seen with the identical (i.e., equimolar) salt formulation. In some embodiments, the Cmax of a freebase and salt mixture formulation is equivalent or within ±5%, ±10%, ±20%, ±30%, or ±40% of the corresponding Cmax of a salt formulation, but the $T_{1/2}$ is at least 10%, 20%, 40%, 60%, 80%, or 100% longer than the $T_{1/2}$ seen with the salt formulation. In some embodiments, the Tmax of a freebase and salt mixture formulation is equivalent or within ±5%, ±10%, ±20%, ±30%, or ±40% of the corresponding Tmax of a salt formulation, but the T½ is at least 10%, 20%, 40%, 60%, 80%, or 100% longer than the T½ seen with the salt formulation.

In some embodiments, intranasal pharmaceutical formulations of freebase and salt mixtures of therapeutic agents are provided that have a Cmax that is no more than about 90%, 80%, 60%, 40%, 20%, or 10% of the Cmax of an identical intranasal pharmaceutical formulation where the therapeutic agent is a salt form at the same molar quantity, but have a Tmax that is at least 10%, 20%, 40%, 60%, 80%, or 100% longer than the Tmax seen with the salt formulation. In some embodiments, intranasal pharmaceutical formulations of freebase and salt mixtures of therapeutic agents are provide that have a Cmax that is no more than about 90%, 80%, 60%, 40%, or 20% of the Cmax of an identical intranasal pharmaceutical formulation where the therapeutic agent is a salt form at the same molar quantity, but have a T½ that is at least 10%, 20%, 40%, 60%, 80%, or 100% longer than the T½ seen with the salt formulation. Such pharmacokinetic profiles can be produced by altering the relative ratios of the freebase form and the salt form as well as altering the particle size of one or both forms of the therapeutic agent.

Formulations can be engineered in a number of ways to provide the desired pharmacokinetic profile or parameters. In some embodiments, the proportion of freebase to salt form of a therapeutic agent can be varied. In some embodiments, the ratio of a salt to a freebase form of the therapeutic agent is equal to or greater than 1:1 on a molar basis. In other embodiments, the ratio of a salt to a freebase form of the therapeutic agent is equal to or greater than 3:1, 2:1, 1:2, 1:3, 1:4, 1:5, 1:10, 1:20, or 1:50 on a molar basis.

Freebase and salt forms of the therapeutic agent in the mixture can be of substantially similar or of equal size distributions. Alternately, the freebase and salt forms of the mixture can be of different size distributions. Further, more than one size distribution for a freebase or salt form of the therapeutic agent can be present in the mixture.

Intranasal formulations can contain a freebase and salt mixture wherein the percent composition of the freebase and salt forms differ and the particle size distributions also differ. For instance, a granisetron intranasal formulation can be made using a ratio of 1:4 of salt to freebase form where the salt form of granisetron has a particle size distribution of greater than 100 μm, while the freebase form of granisetron can have a particle size distribution of 38 μm to 100 μm. Additionally, the intranasal formulations can contain a freebase and salt mixture wherein the percent composition of the freebase and salt forms differ and at least the freebase therapeutic agent is present in at least two different particle size distributions.

Prodrug Mixtures

The control or engineering of pharmacokinetic profiles and parameters of intranasal compositions can also be achieved through the use of prodrugs. A prodrug can be used alone in a formulation or it can be mixed with a salt, freebase, or mixtures of salts and freebases of other therapeutic agents. Depending on the type of chemical modification used to make, or that define a prodrug, higher Cmax and/or longer $T_{1/2}$ may be observed. If the added or modified functional groups improve drug uptake across the nasal mucosa, for example, by changing the solubility of the compound, then early, increased blood concentration of the prodrug will occur. If the prodrug is rapidly processed by the body to release the therapeutic agent, a higher Cmax may result. Furthermore, if the functional groups delay the uptake of the drug across the nasal mucosa and/or the functional groups are slowly processed, the result may be longer $T_{1/2}$.

Combination of Pulmonary and Intranasal Administration

In some embodiments, the pharmaceutical compositions are suitable for simultaneous intranasal and pulmonary administration by the selection of particle size distribution ranges that are best suited for each target. For instance, a formulation of an antibiotic can be provided that has the therapeutic agent present in two particle distribution ranges, the first at 1 μm to 5 μm to treat the lungs, with the second at 20 μm to 100 μm to treat the nasal passages. Similarly, a formulation can be designed that delivers two different drugs, one to the lungs and the other to the nasal passages, wherein delivery is controlled by the particle size of each drug.

Distribution or Partition Coefficient

Many factors affect the pharmacokinetic profile (e.g. Cmax, Tmax, $T_{1/2}$, and BA) of a therapeutic agent. For example, the precise formulation of a therapeutic agent can have profound effects on the pharmacokinetic profile even with the same therapeutic agent. The formulation can, for example, include carriers or excipients that affect the release of the therapeutic agent, the stability of the therapeutic agent, the adhesive properties of the formulation when in contact with biological tissues and/or water, the flowability of the formulation, or the solubility of the therapeutic agent. The formulation can also include different forms of the same therapeutic agent that on their own exhibit different properties that affect their pharmacokinetic properties. For example, the degree of solubility of a therapeutic agent in freebase, salt form or a mixture thereof may in part determine the pharmacokinetic profile. In some embodiments the degree of solubility of a therapeutic agent in salt form, freebase, or a mixture thereof may be determined by measuring the partition or distribution coefficient. A partition (P) or distribution coefficient (D) is the ratio of concentrations of a compound in the two phases of a mixture of two immiscible solvents at equilibrium. Therefore, these coefficients are a measure of differential solubility of the compound between these two solvents.

Generally, one solvent is aqueous, usually water, while the second is hydrophobic. Suitable hydrophobic solvents include but are not limited to octanol, or another substantially water insoluble alcohol including, for example, butanol, heptanol, hexanol, or heptanol. Other substantially water insoluble organic liquids that can be used included, for example, pentane, hexane, heptane, octane, and cyclohexane. Hence, both the partition and distribution coefficient are measures of the hydrophilic ("water loving") or hydrophobic ("water fearing") property of a chemical substance. Partition coefficients are useful, for example, in predicting distribution and bioavailability of drugs within the body. In some cases, hydrophobic drugs with high partition coefficients are preferentially distributed to hydrophobic compartments such as lipid bilayers of cells while hydrophilic drugs (low partition coefficients) are, in some cases, preferentially found in hydrophilic compartments such as blood serum.

The partition coefficient is a ratio of concentrations of un-ionized compound between the two solutions. To measure the partition coefficient of ionizable solutes, the pH of the aqueous phase is adjusted such that the predominant form of the compound is un-ionized. The logarithm of the ratio of the concentrations of the un-ionized solute in the solvents is called Log P or alternatively, c Log P:

$$\log P_{oct/wat} = \log\left(\frac{[\text{solute}]_{octanol}}{[\text{solute}]_{water}^{un\text{-}ionized}}\right)$$

The distribution coefficient is the ratio of the sum of the concentrations of all forms of the compound (ionized plus neutral) in each of the two phases. For measurements of distribution coefficient, the pH of the aqueous phase is buffered to a specific value such that the pH is not significantly perturbed by the introduction of the compound. The logarithm of the ratio of the sum of concentrations of the solute's various forms in one solvent, to the sum of the concentrations of its forms in the other solvent is called Log D:

$$\log D_{oct/wat} = \log\left(\frac{[\text{solute}]_{octanol}}{[\text{solute}]_{water}^{ionized} + [\text{solute}]_{water}^{neutral}}\right)$$

In addition, Log D is pH dependent, hence one must specify the pH at which Log D is measured. Of particular interest is the Log D at pH=7.4 (the physiological pH of blood serum). For un-ionizable compounds, Log P=Log D at any pH.

Additionally, Log D may be determined from Log P calculations or measurements if the pKa of the compound is known or can be estimated. For the estimation of pKa, Hammett type equations can be used. Estimation of Log D (at a given pH) from Log P and $pK_a$.

exact expressions:

$$\log D_{acids} = \log P + \log\left[\frac{1}{(1 + 10^{pH-pK_a})}\right]$$

$$\log D_{bases} = \log P + \log\left[\frac{1}{(1 + 10^{pK_a-pH})}\right]$$

approximations for when the compound is largely ionized:

for acids with $(pH-pK_a)>1$, $\log D_{acids} \cong \log P + pK_a - pH$ for bases with $(pK_a-pH)>1$, $\log D_{bases} \cong P - pK_a + pH$ approximation when the compound is largely un-ionized:

$\log D \cong \log P$

Experimental values for Log P directly correlate to the concentration of the compound in the given solvent system. For example, Log P=1 means a compound would partition 10 parts to 1 part in the given organic: aqueous solvent system and a Log P=0 means a 1:1 partitioning would result. In some embodiments, favorable Log P values include those between about 0 and about 7, about 1 to about 6, about 2 to about 5, about 3 to about 4, about 0 to about 6, about 0 to about 5, about 0 to about 4, about 0 to about 3, about 1 to about 5, about 1 to about 4, about 1 to about 3, about 1 to about 2, about 2 to about 7, about 2 to about 6, about 2 to about 4, about 2 to about 3. In some embodiments, a favorable Log P is at least about 0, at least about 1, at least about 1.5, at least about 2, at least about 2.5, at least about 3, at least about 3.5, at least about 4, at least about 4.5, at least about 5, at least about 5.5, at least about 6, at least about 6.5, and at least about 7.

In some cases, Log D may be more indicative of a drug or compounds biological properties. For example, a compound may exhibit a Log P of 7, but due to the presence of one or more ionizable groups may exhibit a Log D at pH 7.4 of 2. Such a compound may in some cases be expected to exhibit desirable membrane permeability and bioavailability parameters as a result of its favorable Log D value at physiological pH. In some embodiments, favorable Log D values include those between about 0 and about 7, about 1 to about 6, about 2 to about 5, about 3 to about 4, about 0 to about 6, about 0 to about 5, about 0 to about 4, about 0 to about 3, about 1 to about 5, about 1 to about 4, about 1 to about 3, about 1 to about 2, about 2 to about 7, about 2 to about 6, about 2 to about 4, about 2 to about 3. In some embodiments, a favorable Log D is at least about 0, at least about 1, at least about 1.5, at least about 2, at least about 2.5, at least about 3, at least about 3.5, at least about 4, at least about 4.5, at least about 5, at least about 5.5, at least about 6, at least about 6.5, and at least about 7.

The choice of a suitable pH value to perform the Log D experiment may be readily determined by one skilled in the art by considering such factors as route of administration (e.g. oral or nasal), pKa of the compound to be tested, and the pH of the desired biological compartment to be targeted. In some embodiments, suitable pH values for determining Log D values range from the pH of stomach acid of about 2 to the pH of the intestinal lumen of about 7.5, including pH values from about 1.5 to about 8, such as about 1.5 to about 7, about 2.0 to about 7, about 2 to about 6, about 2 to about 5, about 3 to about 8, about 3 to about 7, about 3 to about 6, about 3 to about 5, about 4 to about 8, about 4 to about 7, about 4 to about 6, about 4 to about 5, about 5 to about 8, about 5 to about 7, about 5 to about 6, about 6 to about 8 or about 6 to about 7. In some embodiments, the pH is greater than 2.5, 3.0, 3.5, 4.0, 4.5, 5.0, 5.5, 6.0, 6.5, 7.0, 7.4, 7.5, 8.0, or 8.5. In some embodiments, the pH is less than 2.5, 3.0, 3.5, 4.0, 4.5, 5.0, 5.5, 6.0, 6.5, 7.0, 7.4, 7.5, 8.0, or 8.5.

In some instances, a compound may have a substantially different Log D in its freebase form in comparison to its salt form. In such cases, it may be desirable to assay both forms, or a mixture thereof, to obtain suitable solubility data. For example, a compound in salt form may be very soluble in water and nearly insoluble in an organic phase. Such a compound would have a low Log D value. In contrast, the freebase form of the same compound may be very soluble in an organic solvent, but substantially insoluble in water. Therefore, the freebase form of the same compound may have a significantly higher Log D value and hence, be expected to exhibit different pharmacokinetic profiles.

A formulation herein can be provided that is a mixture of both the salt form of the therapeutic and the freebase form of the therapeutic. The resulting mixture may possess additive, synergistic, or complementary pharmacokinetic properties with respect to the individual forms of the therapeutic alone. For example, a compound in salt form may exhibit a Log D value that is indicative of high solubility which may provide a high Cmax, or short Tmax, while the corresponding freebase form of the same compound may exhibit a substantially different Log D value that is indicative of a long $T_{1/2}$. In such cases, the methods of the present invention provide for the making of and use of formulations which are mixtures of both the salt and freebase forms of the compound. The methods of the present invention further provide for the use of such mixtures to tune the pharmacokinetic properties of a given formulation. For example, a mixture of the salt and freebase forms of the compound may provide for a pharmaceutical formulation that exhibits the aggregate or blended beneficial properties of the salt form such as for example fast absorption, high Cmax, and low Tmax, with the beneficial properties of the freebase form such as for example a long $T_{1/2}$.

The classical method of Log P or Log D determination is the shake-flask method, which consists of dissolving some of the solute in question in a volume of octanol and water by agitation or mixing for a set period of time, then measuring the concentration of the solute in each solvent. The concentration of the solute in each solvent may be measured by any number of methods commonly known in the art such as, for example, UV-Vis spectroscopy; fluorescence spectroscopy; measurement of a radioactive tracer; chromatographic methods (e.g. HPLC) such as, but not limited to, reverse phase, ion exchange, or size exclusion chromatography; or mass spectroscopy. In cases, where measurement of radioactive tracer is used, the entire sample to be measured may comprise the radioactive tracer, or a portion of the sample to be measured may comprise the radioactive tracer. For example, to measure the Log P or Log D of a compound, one may dissolve a mixture of, for example, 99.9% of the compound and 0.1% of the sample that is substituted with tritium at one hydrogen position that is resistant to solvent exchange into a water/octanol mixture in a shake flask. After reaching equilibrium, the concentration of compound in each solvent may then be measured using any number of methods or instruments for detecting radioactive decay known to the art including, but not limited to, scintillation counting, gamma counting, ccd detection, photodiode, photomultplier tube, film, an energy dispersive detector such as a germanium detector, or the like. Other suitable radionuclides suitable for use as radioactive tracers include, but are not limited to, the unstable isotopes of sulfur, iodine, phosphorous, calcium, hydrogen, iron, and carbon. Stable isotopes, but rare isotopes like deuterium can also be used to label a compound. Detection of such labeled compounds can be performed with mass spectrometry or other suitable means.

Methods for estimating partition coefficients include correlating reverse phase HPLC retention time to the retention time of similar compounds with known partition coefficient (Log P or Log D) values. This technique requires that the compounds for which the partition coefficient is unknown and compounds for which the partition coefficient is known be structurally and chemically similar. Other methods for estimating partition coefficients include computational methods such as, for example, atomic based prediction, fragment based prediction, data mining prediction, and molecule mining prediction. Exemplary programs that are capable of providing an estimated log P include Chemistry Development Kit, JOElib, ACD/LogP DB, Simulations Plus, ALOGPS, Marvin, miLogP, PreADMET, and XLOGP3.

In most cases, Log P or Log D values for compounds in an octanol/water solvent system have been shown to correlate well with the results of in vivo drug absorption studies. However, in certain cases other methods have shown improved predictive value. For example, hydrophobic compounds which have a large number of hydrogen bonding functional groups such as hydrophobic peptides or peptidomimetics may exhibit a favorable Log P value and yet show poor absorbance and bioavailability in vivo. In such cases, a delta Log P or delta Log D measurement may be a better predictor of a compound or formulation's pharmacokinetic properties. Delta Log P or delta Log D measurements may involve for example the measurement of the difference between the partition coefficient of a drug or compound in an octanol-water solvent system and the partition coefficient of a drug or compound in a cyclohexane-water solvent system.

Other methods for estimating the pharmacokinetic properties of a compound involve the use of artificial or biological membranes. Log P and Log D measurements provide hydrophobicity data, and actual cell or membrane permeability or transport must then be inferred. n contrast, methods utilizing artificial or biological membranes provide data regarding actual lipid membrane permeability. Furthermore, cell or membrane permeability may be assayed in the context of particular pharmaceutical carriers or adjuvants that may be present in a given formulation. Well known membrane based methods include, but are not limited to, methods using Caco-2, MDR1-MDCKII, or HT29 cells; and the parallel artificial membrane permeability assay (PAMPA). Cell or membrane permeability is widely acknowledged to be important in gastrointestinal drug absorption, but it also has an important role in tissue penetration such as through the blood brain barrier (BBB), and the absorption of nasally administered compounds.

Methods for performing cell permeability assays are widely used in the pharmaceutical industry and include the use of transwell plates or chambers. Cells such as, for example, Caco-2 cells, HT29 cells, MDR1-MDCKII cells, or a combination thereof, may be grown as a monolayer after seeding onto a suitable substrate such as for example the inner chamber of a transwell plate. In some embodiments approximately 2 to approximately 25 days may be required to obtain a monolayer. Variables that may affect the length of time include the number of cells seeded, the relative health of the cells used, the passage number of the cells, the cell type or mixture of cell types used, the cell growth media or media components used, and the cell growth conditions including but not limited to temperature, pH, and humidity. In some cases, the cells may be seeded and grown until they form a fully differentiated layer of intestinal epithelia. The integrity of the monolayer may be confirmed by measurement of trans epithelial electrical resistance (TEER) or Lucifer Yellow permeability. Suitable TEER values indicating an intact monolayer include values from between about 200 $\Omega$/cm2 to about 600 $\Omega$/cm2, including about 225 $\Omega$/cm2, 250 $\Omega$/cm2, 275 $\Omega$/cm2, 300 $\Omega$/cm2, 350 $\Omega$/cm2, 400 $\Omega$/cm2, 450 $\Omega$/cm2, 500 $\Omega$/cm2, and about 550 $\Omega$/cm2.

The drug, compound, or formulation to be tested may then be applied to the inner or outer chamber of the transwell plate and, after a period of incubation, the concentration may be assayed in both the inner and outer chambers using any of the previously described quantitation methods. The transport of the drug, compound, or formulation across the cell barrier is thus measured. Suitable periods of incubation typically are less than about 24 hours, and generally range between a few minutes and four hours. In some cases, the period of incubation is approximately 1, 2, or 3 hours.

The Permeability coefficient (Pc) can be calculated according to the following equation: $Pc=dA/(dt \cdot S \cdot Co)$, where $dA/dt$ is the flux of the test compound across the monolayer (nmol/s); S is the surface area of the cell monolayer (cm2); and Co is the initial concentration ($\mu$M) in the donor compartment. The Pc values are expressed as nm/s. Compounds or formulations that exhibit permeability values less than about 100 nm/s are generally considered low permeability. Compounds that exhibit greater than 100 nm/s permeability values are generally considered to exhibit high transport and expected to exhibit high bioavailability, a short Tmax, and/or a high Cmax.

In some cases, the cells forming the monolayer are polarized and exhibit an apical and a basolateral surface. The choice to apply the drug, compound or formulation to the inner or outer chamber depends on whether basolateral to apical transport or apical to basolateral transport is to be measured. Passively transported compounds show equal permeability in both directions. A high basolateral to apical transport rate in comparison to the apical to basolateral transport rate indicates that the compound is a transporter substrate.

In light of recent conclusions that 80-95% of commercial drugs are absorbed primarily by passive diffusion, there is strong interest in a rapid and inexpensive permeability assay that provides direct data on the passive absorbance mechanism. Kansy et al. *J Med Chem* 41:1007-1010 introduced a new permeability assay called "parallel artificial membrane permeability assay" (PAMPA). This technique involves no cell culture. PAMPA uses two aqueous buffer solution wells separated by an artificial membrane. The artificial membrane consists of a lipid in organic diluent, such as for example phosphatidyl choline in dodecane, 1,2-dioleoyl-sn-glycer-3-phosphocholine (DOPC) in dodecane, or mixtures of various lipids. Other variations on Kansy's method, in some cases, improve on the correlation of PAMPA results with a particular class of compound or compound transport through a particular target (e.g., blood-brain barrier). Unlike Caco-2 experiments, PAMPA assays are compatible with pH profiling at a wide range of pH values to mimic various biological compartments such as the stomach, the intestine, and blood plasma.

The lipid membrane is further supported by a porous filter plate matrix. Suitable commercially available filter matrices include 8 micron diameter pore PVDF, although other pore sizes and filter materials are contemplated as within the scope of the present invention. At the beginning of the experiment, the test compound is diluted in buffer (e.g., 25 µg/mL) and placed in a "donor" well. The compound moves from the donor well, by passive diffusion, into the artificial membrane and then into the "acceptor" well. The rate of permeation is determined by the compound's effective permeability (Pe). The time for experiment setup is greatly reduced compared with cell-monolayer methods. Only passive diffusion is tested and there is no metabolism. Therefore, there are no confounding effects due to active transport or drug degradation, making the data easier to interpret. PAMPA is performed in a 96-well format and it can be rapidly quantitated using for example a UV plate reader or any of the previously described quantitation methods. There are no transporter proteins, so saturation is not an issue.

In some embodiments, the inhalable dry powder pharmaceutical formulation has a water-octanol Log D 7.4 of between about 0 and about 5. In other embodiments, the inhalable pharmaceutical formulation has a water-octanol Log D 7.4 of between about 1 and about 4 or between about 2 and about 4. In other embodiments, the inhalable pharmaceutical formulation has a water-octanol Log D 7.4 of between about 2 and about 4, and wherein the salt and freebase form individually comprise a water-octanol Log D 7.4 of less than 2 or greater than 4.

In some embodiments, the inhalable dry powder formulation has a water-octanol Log P of between about 0 and about 5. In other embodiments, the inhalable dry powder formulation has a water-octanol Log P of between about 1 and about 4 or between about 2 and about 4. In further embodiments, the inhalable pharmaceutical formulation has a water-octanol Log P of between about 2 and about 4, and wherein the salt and freebase form individually comprise a water-octanol Log P of less than 2 or greater than 4.

Dissolution Rates

Inhalable dry powder pharmaceutical formulations can also be developed, categorized, and/or described based on in vitro dissolution rates. Methods to determine dissolution rates can be found in the various pharmacopoeia including the United States Pharmacopoeia 24 (2000), and the Japanese Pharmacopoeia 14 (2001). Typically, tablets, pills, or other solid dosage units are placed in the bottom of the apparatus filled with a dissolution medium with a paddle placed above the solid dosage unit. Alternatively, the solid dosage units are placed in a mesh basket suspended in dissolution medium that contains a stirring mechanism. The medium is held at a constant temperature with constant agitation. Periodically, samples are withdrawn from the vessel, filtered, and analyzed by HPLC, spectrophotometry or other suitable means.

As the instant invention is directed in part to dry powder formulations, the testing methodology is modified to account for the different physical characteristics of a powder. Instead of placing a solid dosage unit on the bottom of an apparatus or in a basket, the dry powder formulation is placed in dialysis tubing that is closed at both ends. FIG. 1 The sample is suspended at one end from the surface with the tubing and enclosed formulation hanging down in the medium. Typically, the dissolution media is deionized water, but aqueous buffered systems that mimic the pH and ionic strength of nasal mucus can be used. A stir bar is placed on the bottom of the container housing the medium. The container is then placed on a heater/stirrer apparatus that is then controlled at a constant temperature and stir rate. Typically, the temperature is set at 37° C. with a stir rate of 60 rpm. Samples are removed periodically and analyzed using HPLC or spectrophotometry.

Inhalable dry powder pharmaceutical formulations comprising a therapeutic agent, wherein at least some of the therapeutic agent is present in a freebase form, are disclosed that have dissolution rates that are slower than the dissolution rates for inhalable dry powder formulations comprising a therapeutic agent, wherein none of the therapeutic agent is present as a freebase. In some embodiments, the inhalable dry powder pharmaceutical formulations comprise a therapeutic agent wherein at least some of which is present in a freebase form have a dissolution rate that is less than 90%, 80%, 70%, 60%, 50%, 40%, 25%, 10% or 5% of the dissolution rate of inhalable dry powder formulations comprising a therapeutic agent wherein none of the therapeutic agent is present as a freebase when measured over the course of 1 minute, 2 minutes, 5 minutes, 10 minutes, 15 minutes, 20 minutes, 25 minutes, 30 minutes, 40 minutes, 50 minutes or 60 minutes. In other embodiments, the inhalable dry powder pharmaceutical compositions comprising a therapeutic agent wherein at least some of the therapeutic agent is present in freebase form, have a dissolution profile such that within about 1, 2, 5, 10, or 20 minutes, at least 10%, 20%, 40%, 60%, 80%, or 90% of the composition is dissolved. In still other embodiments, the inhalable dry powder pharmaceutical compositions comprising a therapeutic agent wherein at least some of the therapeutic agent is present in freebase form, have a dissolution profile such that within about 1, 2, 5, 10, or 20 minutes, less than 10%, 20%, 40%, 60%, 80%, or 90% of the composition is dissolved.

It is generally believed that for solid dosage units, therapeutic agents in salt form have a higher dissolution rate compared to a freebase and therefore salts of therapeutic agents will produce faster onset of action of a therapeutic agent and also greater bioavailability. Therefore, it was a surprising result to discover that this general phenomena did not necessarily hold true for intranasal dry powder formulations. In some embodiments, it was found that contrary to expectations, inhalable dry powder pharmaceutical formulations comprising a therapeutic agent wherein at least some of the therapeutic agent is present as a freebase have equivalent or substantially similar rapid onset of action of the therapeutic agent as measured by Cmax and Tmax. This is true even when the dissolution rate of the dry powder formulation is slower than an identical inhalable dry powder pharmaceutical formulation comprising of only a salt form of the therapeutic agent at an equal molar quantity.

Pharmacokinetic Profiles

Inhalable dry powder pharmaceutical compositions comprising a therapeutic agent wherein at least some of the therapeutic agent is present in freebase form are disclosed that have substantially similar or improved pharmacokinetic profiles and/or parameters compared to an identical pharmaceutical composition comprising of 100% of the salt form of the therapeutic agent at the same molar quantity. The freebase form of the therapeutic agent can represent 100% of the total amount of the therapeutic agent present in the composition, or the therapeutic agent can be present as a mixture of a salt form of the agent with the freebase form. Particle sizes of the salt and freebase forms, when present in the same formulation, can have the same or different mean particle sizes or particle size distributions. Pharmacokinetic profiles can be obtained through standard means known in the art. For example, the pharmacokinetic profiles can be obtained from animals, such as mammals, including primates (e.g., monkeys such as Rhesus Macaques (*Macaca mulatta*), or humans).

Comparisons between pharmaceutical compositions can be readily achieved through the examination of pharmacokinetic profiles and/or parameters measured after administration of a composition. Generally, a blood baseline drug concentration is obtained prior to administration. Post-administration, blood is drawn at various time points for drug analysis. Typically, serum or plasma is isolated from the blood samples and analyzed to determine the concentrations of the therapeutic agent. Traditionally, a graph is created of the time (x-axis) versus drug concentration (y-axis) and from this graph various pharmacokinetic parameters can be derived. Alternately, the data can be entered into a software program that will derive the pharmacokinetic parameters and fit them to a graph of the measured values. Numerous, but non-limiting, pharmacokinetic software programs which can be used in practicing the teachings of the present disclosure are described at the following website: http://www.boomer.org/pkin/soft.

Useful pharmacokinetic parameters in which to compare formulations include maximal blood therapeutic concentration (Cmax), time to reach Cmax (Tmax), time to reach a blood concentration of ½ of Cmax ($T_{1/2}$), and bioavailability (BA). Typically, BA is measured by determining an area under the curve (AUC) of a blood therapeutic concentration versus time graph. For comparative analysis between pharmaceutical compositions, the pharmacokinetic parameters can be compared individually, or in various combinations.

Freebase and Mixture Compositions

Disclosed herein are inhalable dry powder pharmaceutical formulations comprising a therapeutic agent wherein at least some of the therapeutic agent is present in a freebase form that have pharmacokinetic profiles that are substantially similar or improved compared to identical pharmaceutical formulations wherein the therapeutic agent is present only in the salt form at the same molar quantity. In some embodiments, the inhalable dry powder pharmaceutical formulations with at least some freebase present have one or more pharmacokinetic parameters that are substantially similar to the pharmacokinetic parameters observed with an identical pharmaceutical formulation with only the salt form of the therapeutic agent. In other embodiments, the freebase inhalable dry powder pharmaceutical formulation has one or more pharmacokinetic parameters that are substantially improved compared to the pharmacokinetic parameters observed with an identical pharmaceutical formulation with only the salt form of the therapeutic agent. In some embodiments of the invention, the inhalable dry powder pharmaceutical formulations only contain the therapeutic agent as a freebase, while in other embodiments the therapeutic agent is present as a mixture of the freebase form and a salt form of the therapeutic agent. In some embodiments, is the percentage of a salt form of a therapeutic agent in a mixture when calculated by molar quantity is from about 0.0% to about 99.9%. In some embodiments, the percentage of a salt form of a therapeutic agent in a mixture when calculated by molar quantity may range from about 1% to about 99%, about 5% to about 95%, about 10% to about 90%, about 20% to about 80%, 30% to about 70%, and about 40% to about 60%. In further embodiments, the percentage of a salt form of a therapeutic agent in a mixture when calculated by molar quantity is at least 0%, 1%, 5%, 10%, 20%, 30%, 40%, 50%, 60%, 70%, 80%, 90% or 95%. In other embodiments, the percentage of a salt form of a therapeutic agent in a mixture when calculated by molar quantity is less than 99%, 95%, 90%, 80%, 70%, 60%, 50%, 40%, 30%, 20%, 10%, or 5%.

Cmax

In some embodiments, an inhalable dry powder pharmaceutical formulation comprising a therapeutic agent wherein at least some of the therapeutic agent is present in a freebase form when administered to a primate has a maximal blood therapeutic concentration (Cmax) that is substantially similar to the Cmax of an identical inhalable dry powder pharmaceutical formulation comprising the salt form of the therapeutic agent when the therapeutic agent is present at the same molar quantity in both compositions. In some embodiments, the inhalable dry powder pharmaceutical formulation comprising the freebase form has a maximal blood therapeutic concentration (Cmax) that is about ±5%, ±10%, ±20%, ±30%, or ±40% of the Cmax of an identical inhalable dry powder pharmaceutical formulation comprising the salt form of the therapeutic agent when the therapeutic agent is present at the same molar quantity in both compositions.

Additionally, an inhalable dry powder pharmaceutical formulation comprising a therapeutic agent wherein at least some of the therapeutic agent is present in a freebase form when administered to a primate can have a maximal blood therapeutic concentration (Cmax) that is at least 95% of the Cmax of an otherwise identical inhalable dry powder pharmaceutical formulation comprising the salt form of the therapeutic agent when the therapeutic agent is present at the same molar quantity in both compositions. In some embodiments, an inhalable dry powder pharmaceutical formulation comprising a mixture of salt and freebase form of a therapeutic agent when administered to a primate has a Cmax that is at least 400%, 200%, 150%, 125%, 110%, 90%, 80%, 60%, or 40% of the Cmax of an otherwise identical inhalable dry powder pharmaceutical formulation comprising the salt form of the therapeutic agent when the therapeutic agent is present at the same molar quantity in both compositions.

Also disclosed herein is an inhalable dry powder pharmaceutical formulation comprising a therapeutic agent wherein at least some of the therapeutic agent is present in a freebase form that when administered to a primate can have a maximal blood therapeutic concentration (Cmax) that is substantially higher than the Cmax of an otherwise identical inhalable dry powder pharmaceutical formulation comprising the salt form of the therapeutic agent when the therapeutic agent is present at the same molar quantity in both compositions. In some embodiments, an inhalable dry powder pharmaceutical formulation comprising a freebase form of a therapeutic agent when administered to a primate has a Cmax that is at least about 150%, 200%, 300%, 400%, 500%, or 1000% greater then the Cmax of an otherwise identical inhalable dry powder pharmaceutical formulation comprising only the salt form of the therapeutic agent when the therapeutic agent is present at the same molar quantity in both compositions.

Tmax

In some embodiments, an inhalable dry powder pharmaceutical formulation comprising a therapeutic agent wherein at least some of the therapeutic agent is present in a freebase form when administered to a primate has a time to reach a blood concentration Cmax (Tmax) that is substantially similar to the Cmax of an otherwise identical inhalable dry powder pharmaceutical formulation comprising the salt form of the therapeutic agent when the therapeutic agent is present at the same molar quantity in both compositions. In some embodiments, the inhalable dry powder pharmaceutical formulation comprising the freebase form has a maximal blood therapeutic concentration (Cmax) that is about ±5%, ±10%, ±20%, ±30%, or ±40% of the Cmax of an otherwise identical inhalable dry powder pharmaceutical formulation comprising the salt form of the therapeutic agent when the therapeutic agent is present at the same molar quantity in both compositions.

In some embodiments, an inhalable dry powder pharmaceutical formulation comprising a therapeutic agent wherein at least some of the therapeutic agent is present in a freebase form when administered to a primate has a time to reach a blood concentration Cmax (Tmax) that is at least 95% of the $T_{1/2}$ of an otherwise identical inhalable dry powder pharmaceutical formulation comprising the salt form of the therapeutic agent when the therapeutic agent is present at the same molar quantity in both compositions. In some embodiments, an inhalable dry powder pharmaceutical formulation comprising a therapeutic agent wherein at least some of the therapeutic agent is present in a freebase form when administered to a primate has a Tmax that is at least 400%, 200%, 150%, 125%, 110%, 90%, 80%, 60%, or 40% of the Cmax of an otherwise identical inhalable dry powder pharmaceutical formulation comprising the salt form of the therapeutic agent when the therapeutic agent is present at the same molar quantity in both compositions.

Also disclosed herein is an inhalable dry powder pharmaceutical formulation comprising a therapeutic agent wherein at least some of the therapeutic agent is present in a freebase form that when administered to a primate can have a Tmax that is substantially higher than the Tmax of an otherwise identical inhalable dry powder pharmaceutical formulation comprising the salt form of the therapeutic agent when the therapeutic agent is present at the same molar quantity in both compositions. In some embodiments, an inhalable dry powder pharmaceutical formulation comprising a therapeutic agent wherein at least some of the therapeutic agent is present in a freebase form when administered to a primate has a Tmax that is at least about 150%, 200%, 300%, 400%, 500%, or 1000% greater then the Tmax of an otherwise identical inhalable dry powder pharmaceutical formulation comprising the salt form of the therapeutic agent when the therapeutic agent is present at the same molar quantity in both compositions.

$T_{1/2}$

In some embodiments, an inhalable dry powder pharmaceutical formulation comprising a therapeutic agent wherein at least some of the therapeutic agent is present in a freebase form when administered to a primate has a time to reach a blood concentration of ½ of Cmax ($T_{1/2}$) that is at least 95% of the $T_{1/2}$ of an otherwise identical inhalable dry powder pharmaceutical formulation comprising the salt form of the therapeutic agent when the therapeutic agent is present at the same molar quantity in both compositions. In some embodiments, an inhalable dry powder pharmaceutical formulation comprising a therapeutic agent wherein at least some of the therapeutic agent is present in a freebase form when administered to a primate has a $T_{1/2}$ that is at least 400%, 200%, 150%, 125%, 110%, 90%, 80%, 60%, or 40% of the $T_{1/2}$ of an otherwise identical inhalable dry powder pharmaceutical formulation comprising the salt form of the therapeutic agent when the therapeutic agent is present at the same molar quantity in both compositions.

Bioavailability

In some embodiments, an inhalable dry powder pharmaceutical formulation comprising a therapeutic agent wherein at least some of the therapeutic agent is present in a freebase form, wherein the bioavailability (BA) of the therapeutic agent in the pharmaceutical formulation is at least 95% of the BA of the therapeutic agent when present at 100% salt form at the same molar quantity in an otherwise identical pharmaceutical formulation when administered to a primate.

In some embodiments, an inhalable dry powder pharmaceutical comprising a therapeutic agent wherein at least some of which is present in a freebase form has a BA that is at least 800%, 400%, 200%, 150%, 125%, 110%, 90%, 80%, 60%, or 40% of the BA of the therapeutic agent when present at 100% salt form at the same molar quantity in an otherwise identical pharmaceutical formulation when administered to a primate.

Generally, pharmaceutical formulations with increased bioavailability allow for the use of smaller amounts of a therapeutic agent to achieve one or more desired pharmacological effects. In some embodiments, inhalable dry powder pharmaceutical formulations comprising a therapeutic agent wherein at least some of the therapeutic agent is present in freebase form can be administered at a dose that is about 10% below the dose required by an identical formulation containing the therapeutic agent in a salt form at equal molar quantities to achieve one or more desired pharmacological effects. In some embodiments, inhalable dry powder pharmaceutical formulations comprising a therapeutic agent wherein at least some of the therapeutic agent is present in a freebase form can be administered at a dose that is about 20% below, about 30% below, about 40% below, about 50% below, or about 75% below the dose required by an identical formulation containing a therapeutic agent in a salt form at equal molar quantities to achieve one or more desired pharmacological effects. Desired pharmacological effects depend on the disease or condition being treated and the particular drug or drug class being used, but can include a reduction in one or more symptoms of the disease or condition; a reduction in pain, inflammations, or desired biomarkers; or an increase in mobility, appetite, alertness, cognitive ability, blood counts, or desired biomarkers.

Granisetron Formulations

In some embodiments, granisetron is administered as an inhalable dry powder pharmaceutical formulation wherein at least some of the granisetron is present in a freebase form in an amount sufficient to achieve in a patient a blood plasma concentration greater than or equal to 1, 5, 10, 20, 50, 100, 150, 200, 250, 300, 350, 400, 450, 500, 550, 600, 650, 700, 750, 800, 850, 900, 950, or 1000 nM. In some embodiments, the inhalable dry powder formulation is administered in an amount sufficient to achieve a blood plasma level in a patient greater than or equal to 250 nM or 350 nM. In certain embodiments, it is administered in an amount sufficient to achieve in a patient a blood plasma concentration in the range of 1-10 nM, 1-100 nM, 10-1000 nM, 50-500 nM, 100-500 nM, 200-400 nM, 200-1000 nM, or 500-1000 nM.

In some embodiments, granisetron is administered as an inhalable dry powder pharmaceutical formulation wherein at least some of the granisetron is present in a freebase form in an amount sufficient to achieve a blood plasma concentration in a patient of at least 100 nM, at least 150 nM, at least 200 nM, at least 250 nM, at least 300 nM, at least 350 nM, at least 400 nM, at least 450 nM, at least 500 nM, at least 550 nM, or greater than 550 nM. In certain embodiments, granisetron is administered in an amount sufficient to maintain a blood concentration in a patient of at least 100 nM, at least 150 nM, at least 200 nM, at least 250 nM, at least 300 nM, at least 350 nM, at least 400 nM, at least 450 nM, at least 500 nM, at least 550 nM, or greater than 550 nM for at least 1, 2, 4, 6, 8, 10, or 12 hours.

In some embodiments, granisetron is administered as an inhalable dry powder pharmaceutical formulation, wherein at least some of the granisetron is present in a freebase form, in an amount within the range of from about 0.01 mg/kg to about 100 mg/kg, from about 0.1 mg/kg to about 50 mg/kg, from about 0.5 mg/kg to about 20 mg/kg, or from about 1.0 mg/kg to about 10 mg/kg. In particular embodiments, granisetron is administered in an amount within the range of about 1 mg/kg to about 10 mg/kg, from about 2 mg/kg to about 10 mg/kg, from about 4 mg/kg to about 8 mg/kg or about 6 mg/kg to about 8 mg/kg. In one embodiment, granisetron is administered at approximately X mg/kg. Thus, in particular embodiments, a total amount of between approximately 100-1000 mg, 100-500 mg, 200-500 mg, 300-500 mg, or 400-500 mg of granisetron is administered to a patient as a single or multiple dose. In one embodiment, approximately 450 mg is administered to a patient.

In some embodiments, the granisetron inhalable dry powder pharmaceutical formulations, wherein at least some of the granisetron is present in a freebase form have following a mg dose to a human, a Cmax that is greater than about 440 ng/mL, greater than about 450 ng/mL, greater than about 500 ng/mL, greater than about 550 ng/mL, greater than about 600 ng/mL, greater than about 650 ng/mL, greater than about 700 ng/mL, greater than about 750 ng/mL, greater than about 800 ng/mL, greater than about 850 ng/mL, greater than about 900 ng/mL, greater than about 950 ng/mL, greater than about 1000 ng/mL, greater than about 1050 ng/mL, greater than about 1100 ng/mL, greater than about 1150 ng/mL, greater than about 1200 ng/mL, greater than about 1250 ng/mL, greater than about 1300 ng/mL, about 1350 ng/mL, or greater than about 1400 ng/mL.

In comparative pharmacokinetic testing with an injectable granisetron composition (e.g., Kytril®) a granisetron inhalable dry powder pharmaceutical formulation, wherein at least some of the granisetron is present in a freebase form, administered at 2.0 mg exhibits in a patient a Cmax which is greater than about 5%, greater than about 10%, greater than about 15%, greater than about 20%, greater than about 30%, greater than about 40%, greater than about 50%, greater than about 60%, greater than about 70%, greater than about 80%, greater than about 90%, greater than about 100%, greater than about 110%, greater than about 120%, greater than about 130%, greater than about 140%, or greater than about 150% than the Cmax exhibited by intravenous granisetron administered at 10 µg/kg.

Following administration of a 2 mg dose of a granisetron inhalable dry powder pharmaceutical formulation to a patient, wherein at least some of the granisetron is present in a freebase form of the invention, the resulting Cmax is preferably greater than about 5.0 ng/mL, greater than about 8.0 ng/mL, greater than about 10.0 ng/mL, greater than about 12.0 ng/mL, greater than about 15.0 ng/mL, greater than about 18.0 ng/mL, greater than about 20.0 ng/mL, greater than about 22.0 ng/mL, or greater than about 24.0 ng/mL.

In comparative pharmacokinetic testing with an injectable granisetron composition (e.g., Kytril®) a granisetron inhalable dry powder pharmaceutical formulation, wherein at least some of the granisetron is present in a freebase form, administered at 2.0 mg to a patient exhibits an AUC which is greater than about 5%, greater than about 10%, greater than about 15%, greater than about 20%, greater than about 30%, greater than about 40%, greater than about 50%, greater than about 60%, greater than about 70%, greater than about 80%, greater than about 90%, greater than about 100%, greater than about 110%, greater than about 120%, greater than about 130%, greater than about 140%, or greater than about 150% than the AUC exhibited by intravenous granisetron administered a 10 µg/kg.

In some embodiments, the granisetron inhalable dry powder pharmaceutical formulations of the present invention, wherein at least some of the granisetron is present in a freebase form will produce following a 2.0 mg dose to a human, a Cmax that is greater than about 5.0 ng/mL, greater than about 10.0 ng/mL, greater than about 15.0 ng/mL, greater than about 20.0 ng/mL, greater than about 25.0 ng/mL, greater than about 30.0 ng/mL, greater than about 35.0 ng/mL, or greater than about 40 ng/mL.

In some embodiments, the granisetron inhalable dry powder pharmaceutical formulations, wherein at least some of the granisetron is present in a freebase form have following a 2.0 mg dose to a human, a Tmax of less than about 90 minutes, less than about 80 minutes, less than about 60 minutes, less than about 50 minutes, less than about 40 minutes, less than about 30 minutes, or less than about 20 minutes.

In some embodiments, the granisetron inhalable dry powder pharmaceutical formulations, wherein at least some of the granisetron is present in a freebase form have following a 2.0 mg dose to a human, a $T_{1/2}$ of at least about 4.0 hours, at least about 5.0 hours, at least about 6.0 hours, at least about 7.0 hours, at least about 8.0 hours, at least about 9.0 hours, at least about 10.0 hours, at least about 11.0 hours, at least about 12.0 hours, at least about 13.0 hours, or at least about 14.0 hours.

In some embodiments, the granisetron inhalable dry powder pharmaceutical formulations, wherein at least some of the granisetron is present in a freebase form have following a 2.0 mg dose to a human, a BA of at least about 60%, at least about 70%, at least about 80%, at least about 90%, at least about 95% or at least about 99%.

Sumatriptan Formulations

In some embodiments, the sumatriptan inhalable dry powder pharmaceutical formulations, wherein at least some of the sumatriptan is present in a freebase form when administered to a rhesus monkey at a 6.0 mg dose have a Cmax that is greater than about 200 ng/mL, greater than about 300 ng/mL, greater than about 400 ng/mL, greater than about 500 ng/mL, greater than about 600 ng/mL, greater than about 700 ng/mL, greater than about 800 ng/mL, or greater than about 900 ng/mL.

In some embodiments, the sumatriptan inhalable dry powder pharmaceutical formulations, wherein at least some of the sumatriptan is present in a freebase form when administered to a rhesus monkey at a 6.0 mg dose have a Tmax of less than about 90 minutes, less than about 80 minutes, less than about 60 minutes, less than about 50 minutes, less than about 40 minutes, less than about 30 minutes, or less than about 20 minutes.

In some embodiments, the sumatriptan inhalable dry powder pharmaceutical formulations, wherein at least some of the sumatriptan is present in a freebase form when administered to a rhesus monkey at a 6.0 mg dose have a $T_{1/2}$ of at least about 4.0 hours, at least about 5.0 hours, at least about 6.0 hours, at least about 7.0 hours, at least about 8.0 hours, at least about 9.0 hours, at least about 10.0 hours, at least about 11.0 hours, at least about 12.0 hours, at least about 13.0 hours, or at least about 14.0 hours.

In some embodiments, the sumatriptan inhalable dry powder pharmaceutical formulations, wherein at least some of the sumatriptan is present in a freebase form when administered to a rhesus monkey at a 6.0 mg dose have a BA of at least about 60%, at least about 70%, at least about 80%, at least about 90%, at least about 95% or at least about 99%.

Zolmitriptan Formulations

In some embodiments, zolmitriptan is administered as an inhalable dry powder pharmaceutical formulation wherein at least some of the zolmitriptan is present in a freebase form in an amount sufficient to achieve in a rhesus monkey a blood plasma concentration greater than or equal to 1, 5, 10, 20, 50, 100, 150, 200, 250, 300, 350, 400, 450, 500, 550, 600, 650, 700, 750, 800, 850, 900, 950, or 1000 nM. In some embodiments, the inhalable dry powder formulation is administered in an amount sufficient to achieve a blood plasma level greater than or equal to 250 nM or 350 nM. In certain embodiments, it is administered in an amount sufficient to achieve a blood plasma concentration in the range of 1-10 nM, 1-100 nM, 10-1000 nM, 50-500 nM, 100-500 nM, 200-400 nM, 200-1000 nM, or 500-1000 nM.

In some embodiments, zolmitriptan is administered as an inhalable dry powder pharmaceutical formulation wherein at least some of the zolmitriptan is present in a freebase form in an amount sufficient to achieve a blood plasma concentration of at least 100 nM, at least 150 nM, at least 200 nM, at least 250 nM, at least 300 nM, at least 350 nM, at least 400 nM, at least 450 nM, at least 500 nM, at least 550 nM, or at least 600 nM. In certain embodiments, zolmitriptan is administered in an amount sufficient to maintain a blood concentration of at least 100 nM, at least 150 nM, at least 200 nM, at least 250 nM, at least 300 nM, at least 350 nM, at least 400 nM, at least 450 nM, at least 500 nM, at least 550 nM, or greater than 550 nM for at least 1, 2, 4, 6, 8, 10, or 12 hours.

In some embodiments, zolmitriptan is administered as an inhalable dry powder pharmaceutical formulation, wherein at least some of the zolmitriptan is present in a freebase form, in an amount within the range of from about 0.01 mg/kg to about 100 mg/kg, from about 0.1 mg/kg to about 50 mg/kg, from about 0.5 mg/kg to about 20 mg/kg, or from about 1.0 mg/kg to about 10 mg/kg. In particular embodiments, zolmitriptan is administered in an amount within the range of about 1 mg/kg to about 10 mg/kg, from about 2 mg/kg to about 10 mg/kg, from about 4 mg/kg to about 8 mg/kg or about 6 mg/kg to about 8 mg/kg. In one embodiment, zolmitriptan is administered at approximately X mg/kg. Thus, in particular embodiments, a total amount of between approximately 100-1000 mg, 100-500 mg, 200-500 mg, 300-500 mg, or 400-500 mg of zolmitriptan is administered to a patient as a dose. In one embodiment, approximately 450 mg is administered to a patient.

In some embodiments, the zolmitriptan inhalable dry powder pharmaceutical formulations, wherein at least some of the zolmitriptan is present in a freebase form have following a mg dose to a human, a Cmax that is greater than about 440 ng/mL, greater than about 450 ng/mL, greater than about 500 ng/mL, greater than about 550 ng/mL, greater than about 600 ng/mL, greater than about 650 ng/mL, greater than about 700 ng/mL, greater than about 750 ng/mL, greater than about 800 ng/mL, greater than about 850 ng/mL, greater than about 900 ng/mL, greater than about 950 ng/mL, greater than about 1000 ng/mL, greater than about 1050 ng/mL, greater than about 1100 ng/mL, greater than about 1150 ng/mL, greater than about 1200 ng/mL, greater than about 1250 ng/mL, greater than about 1300 ng/mL, about 1350 ng/mL, or greater than about 1400 ng/mL.

Other Therapeutic Agents

In addition to the therapeutic agents disclosed herein in the examples and text, other agents can be prepared as one of the therapeutic components of the compositions herein. Non-limiting examples of classes of drugs include: antibiotics, antifungal agents, sulfa drugs, antituberculosis drugs, antimicrobial agents, antiviral agents, hypnotic sedatives, antiepileptic agents, narcotic analgesics, normarcotic analgesics, sedative drugs, psychotherapeutic agents, muscle relaxants, antiallergic agents, anti-rheumatic drugs, cardiotonic drugs, antiarrhythmic agents and antihypertensive agents, diuretic agents, coronary vasodilators, antidementia drugs, brain activators, brain circulation ameliorating agents, antiparkinsonian agents, antihyperlipidemic drugs, antiulcer drugs, antiemetic agents, obesity drugs, diabetic drugs, hemostatic drugs, antithrombotic agents, migraine drugs, antitussive drugs and expectorants, respiratory stimulants, asthma drugs, antidiarrheal drugs, nonsteroidal antiinflammatory agents, antipodagrics, therapeutic agents for urinary diseases, drugs for improving sexual function, agents for the uterus, steroids, prostaglandins, vitamins, histamines, antidotes, therapeutic agents for heavy metal toxification, quit smoking agents, antianaphylactic agents, and antitumor agents.

Specific, non-limiting examples of particular drugs include: antibiotics such as penicillins, carbapenems, cephems, aminoglycosides, macrolides, tetracyclines, and chloramphenicols; antifungal agents such as amphotericin B, griseofulvin, nystatin, fluconazole, flucytosine, and miconazole; sulfa drugs such as salazosulfapyridine and sulfamethoxazole; antituberculosis drugs such as isoniazid, ethambutol, and rifampicin; antimicrobial agents such as enoxacin, ofloxacin, ciproflaxacin, tosufloxacin, and norfloxacin; antiviral agents such as vidarabine, aciclovir, didanosine, zidovudine, oseltamivir, zanamivir, and valganciclovir; sleep aids such as brotizolam, triazolam, and zopiclone; antiepileptic agents such as carbamazepine, clonazepam, zonisamide, valproic acid, phenyloin, phenobarbital, and primidone; narcotic analgesics such morphine, fentanyl, and pethidine; normarcotic analgesics such as buprenorphine, pentazocine, and tramadol hydrochloride; sedative drugs such as midazolam; psychotherapeutic agents such as chlorpromazine, haloperidol, tryptanol, imipramine, clomipramine, etizolam, oxazolam, and diazepam; muscle relaxants such as eperisone, tizanidine, baclofen, suxamethonium chloride, pancuronium bromide, and dantrolene; antiallergic agents such as chlorpheniramine, cyproheptadine, mequitazine, diphenhydramine, and sodium cromoglycate; anti-rheumatic drugs such as auranofin, bucillamine, and D-penicillamine; cardiotonic drugs such as digoxin and digitoxin; antiarrhythmic agents and antihypertensive agents such as atenolol, propranolol, metoprolol, amiodarone, quinidine, procainamide, mexiletine, nicardipine, enalapril, captopril, prazosin, hydralazine, reserpine, and clonidine; diuretic agents such as hydrochlorothiazide, potassium canrenoate, spironolactone, mannitol, acetazolamide, and furosemide; coronary vasodilators such as diltiazem, nifedipine, verapamil, and dipyridamole; antidementia drugs such as donepezil hydrochloride, galanthamine, and memantine; brain activators such as citicoline and tiapride; brain circulation ameliorating agents such as ATP, isosorbide, and nicergoline; antiparkinsonian agents such as trihexyphenidyl, biperiden, levodopa, dopamine, and amantadine; antihyperlipidemic drugs such as clofibrate and pravastatin; antitumor agents such as cimetidine, famotidine, omeprazole, lansoprazole, pirenzepine, aldioxa, sofalcone, and teprenone; antiemetic agents such as granisetron, ondansetron, tropisetron, cisapride, domperidone, and metoclopramide; obesity drugs such as mazindol; diabetic drugs such as pioglitazone hydrochloride, voglibose, gliclazide, acarbose, ciglitazone, sorbinil, glimepiride, epalrestat, ganglioside, midaglizole hydrochloride, and ponalrestat; hemostatic drugs such as cabazochrome and tranexamic acid; antithrombotic agents such as heparin, low-molecular-weight heparin, warfarin, cilostazol, ticlopidine, ethyl icosapentate, andberaprost; migraine drugs such as ergotamine, dihydroergotamine, and sumatriptan; antitussive drugs and expectorants such as codeine, tipepidine, dextromethorphan, acetylcysteine, carbocysteine, and bromhexine; respiratory stimulants, such dimorpholamine, doxapram, and naloxone; asthma drugs such as salbutamol, terbutaline, procaterol, theophylline, ephedrine, ibudilast, ketotifen, terfenadine, tranilast, and beclomethasone; antidiarrheal drugs such as loperamide; nonsteroidal antiinflammatory agents such as mefenamic acid, indomethacin, ibuprofen, ketoprofen, loxoprofen, and diclofenac; antipodagrics such as allopurinol, colchicine, and benzbromarone; therapeutic agents for urinary diseases such as estramustine, chlormadinone, flavoxate, and oxybutynin; drugs for improvement in sexual function such as sildenafil, vardenafil, and apomorphine; uterus acting drugs such asisoxsuprine, dinoprost, ritodrine, oestriol, and econazole; steroids such as dexamethasone, triamcinolone, hydrocortisone, prednisolone, testosterone, estradiol, and chlormadinone; prostaglandins such as alprostadil, limaprost, and dinoprost; vitamins such as retinol, thiamine, riboflavin, pyridoxal, cobalamine, and pantothenic acid; antidotes such as pralidoxime iodide methyl, protamine, and leucovorin; therapeutic agents for heavy metal toxification such as dimercaprol and sodium thiosulfate; quit smoking aids such as nicotine; antianaphylactic agents such as epinephrine; antitumor agents such as cyclophosphamide, dacarbazine, cytarabine, tegafur, 5-FU, methotrexate, mercaptopurine, epirubicin, doxorubicin, mitomycin, and etoposide, didanosine, zidovudine, lamivudine, atazanavir, nelfenavir, sanilvudine, emtricitabine, oseltamivir, zanamivir, valganciclovir, amantadine, ketamine, pentobarbital sodium, lidocaine, estazolam, midazolam, triazolam, nitrazepam, flunitrazepam, rilmazafone, zopiclone, brotizolam, chloral hydrate, carbamazepine, clonazepam, zonisamide, sodium valproate, phenyloin, phenobarbital, primidone, gabapentin, opium, morphine, ethylmorphine, oxycodone, codeine, dihydrocodeine, fentanyl, droperidol, levorphanol, methadone, meperidine, pethidine, buprenorphine, butorphanol, tramadol, nalfurafine, pentazocine, sulpyrine, aspirin, acetaminophen, ergotamine, dihydroergotamine, sumatriptan, eletriptan, zolmitriptan, rizatriptan, naratriptan, donepezil, suxamethonium, pancuronium, sildenafil, vardenafil, apomorphine, tadalafil, atropine, scopolamine, digitoxin, digoxin, methyldigoxin, isosorbide, nitroglycerin, quinidine, disopyramide, dopamine, dobutamine, epinephrine, etilefrine, norepinephrine, phenylephrine, dimorpholamine, doxapram, naloxone, flumazenil, tipepidine, dextromethorphan, ambroxol, bromhexine, salbutamol, terbutaline, procaterol, theophylline, ephedrine, sodium cromoglycate, ketotifen, oxatomide, tranilast, granisetron, azasetron, ramosetron, tropisetron, indisetron, palonosetron, cisapride, domperidone, metoclopramide, trimebutine, loperamide, mefenamic acid, indomethacin, sulindac, ibuprofen, ketoprofen, naproxen, pranoprofen, loxoprofen, diclofenac, tiaprofenic acid, tiaramide, carbazochrome sulfonic acid, tranexamic acid, pralidoxime iodide methyl, protamine, leucovorin, dimercaprol, deferoxamine, and sodium thiosulfate.

Carrier/Formulation Technology

Types of Carrier

Within the compositions, formulations and methods of this invention, a therapeutic agent may be combined or coordinately administered with a suitable carrier or vehicle. As used herein, the term "carrier" means a pharmaceutically acceptable solid filler, diluent, encapsulating and/or carrying material. Carriers are usually inert and frequently function as a diluent for dispensing the therapeutic agent into a storage container like a capsule or in a device. Often, the dose to be administered is very small, for example 200 micrograms or 400 micrograms. Usually, such small quantities cannot not be accurately dispensed by themselves into storage containers or devices. By blending the drug, usually uniformly, with a large excess of a carrier, the amount dispensed into the containers is substantially increased, thus facilitating the mechanical dispensing operation. Similarly, the use of a carrier facilitates the administration of the therapeutic agent to the patient, increases dosing homogeneity and reduces the amount of therapeutic agent that remains localized in the administration device.

In some embodiments, a pharmaceutically acceptable carrier for the present compositions and formulations include but are not limited to amino acids, peptides, proteins, non-biological polymers, biological polymers, simple sugars, carbohydrates, gums, inorganic salts and metal compounds which may be present singularly or in combination. In some embodiments, the pharmaceutically acceptable carrier comprises native, derivatized, modified forms, or combinations thereof.

In some embodiments, useful proteins include, but are not limited to, gelatin or albumin. In some embodiments, useful sugars that can serve as pharmaceutically acceptable carriers include, but are not limited to fructose, galactose, glucose, lactitol, lactose, maltitol, maltose, mannitol, melezitose, myoinositol, palatinite, raffinose, stachyose, sucrose, trehalose, xylitol, hydrates thereof, and combinations of thereof.

In some embodiments, useful carbohydrates that can serve as pharmaceutically acceptable carriers include, but are not limited to starches such as corn starch, potato starch, amylose, amylopectin, pectin, hydroxypropyl starch, carboxymethyl starch, and cross-linked starch. In other embodiments, useful carbohydrates that can serve as pharmaceutically acceptable carriers include, but are not limited to cellulose, crystalline cellulose, microcrystalline cellulose, α-cellulose, methylcellulose, hydroxypropyl cellulose, carboxymethyl cellulose, ethyl cellulose, hydroxypropyl methyl cellulose, and cellulose acetate.

In another embodiment, useful inorganic salts or metal compounds include, but are not limited to aluminum, calcium, magnesium, silicon, and zinc salts. In some embodiments, the aluminum salts include for example, aluminum hydroxychloride, aluminum magnesium hydroxide, aluminum hydroxide, aluminum sulfate, aluminum stearate, aluminum monostearate and potassium aluminum sulfate. In other embodiments, the calcium salts include for example, apatite, hydroxyapatite, calcium carbonate, calcium chloride, calcium citrate, calcium silicate, calcium oxide, calcium hydroxide, calcium stearate, calcium phosphate tribasic, calcium lactate, calcium oleate, calcium palmirate, calcium hydrogenphosphate, calcium primary phosphate, calcium acetate, and calcium sulfate. In some embodiments, the magnesium compounds include, for example, magnesium chloride, magnesium aluminate silicate, magnesium silicate, magnesium oxide, magnesium hydroxide, magnesium stearate, magnesium carbonate, magnesium sulfate, and sodium magnesium silicate. Further useful metal compounds in the form of crystalline polyvalence metal compounds are listed in U.S. Pat. No. 5,603,943.

Substantially Water Insoluble Carriers

In some embodiments, the carrier is substantially water insoluble. In further embodiments, the substantially water insoluble carrier is selected from the group consisting of peptides, proteins, non-biological polymers, biological polymers, carbohydrates, gums, inorganic salts and metal compounds. In some embodiments, substantially water insoluble carbohydrates include cellulose, crystalline cellulose, and microcrystalline cellulose. Substantially water insoluble carriers can absorb water, often forming gels, however, their solubility in water is less than X g/l.

Substantially Water Soluble Carriers

In some embodiments, the carrier is substantially water soluble. In further embodiments, the substantially water soluble carrier is selected from the group consisting of polysacchrides, sugars, salts, peptides, proteins, carbohydrates, non-biological polymers, biological polymers, gums, inorganic salts and metal compounds. In some embodiments, the substantially water soluble polysaccharide is cellulose. In some embodiments, the cellulose is hydroxypropyl cellulose, carboxymethyl cellulose, ethyl cellulose, hydroxypropyl methyl cellulose, or cellulose acetate. In other embodiments, the substantially water soluble polysaccharide is a starch. In some embodiments, the substantially water soluble starch is hydroxypropyl starch, carboxymethyl starch, cross-linked starch, amylose, amylopectin, or pectin and combinations of thereof. In some embodiments, the substantially water soluble sugar includes fructose, galactose, glucose, lactitol, lactose, maltitol, maltose, mannitol, melezitose, myoinositol, palatinite, raffinose, stachyose, sucrose, trehalose, xylitol, hydrates thereof, and combinations of thereof.

Size of Carrier

Usually, carriers have a mean particle size and/or particle size distribution that is substantially larger than that of the drug. The small particle size of therapeutic agents frequently exhibit very poor flow properties that compromise the filling accuracy of the dispensed agent when it is loaded into storage containers like capsules or into devices. The same poor flow properties will also impede aerosolisation and compromise the intended amount of therapeutic agent to be delivered to the patient. By blending a microtine therapeutic agent with an excess of carrier that has a substantially larger median particle size, the flow properties of the composition will essentially determine the properties of the carrier thereby improving the handling characteristics required for accurate dispensing and administration.

For some formulations herein, the carrier particles have a mean particle size of at least 1 µm, at least 2 µm, at least 3 µm, at least 4 µm, at least 5 µm, at least 10 µm, at least 15 µm, at least 20 µm, at least, 25 µm, at least 30 µm, at least 40 µm, at least 50 µm, at least 60 µm, at least 70 µm, at least 80 µm, at least 90 µm, at least 100 µm, at least 150 µm, at least 200 µm, or at least 250 µm.

In other formulations, the carrier particles have a size distribution range of about 10 µm to about 350 µm. In other embodiments, the particle size range is from about 10 µm to about 250 µm, about 10 µm to about 200 µm, about 10 µm to about 150 µm, about 10 µm to about 100 µm, about 20 µm to about 100 µm, about 20 µm to about 53 µm, about 38 µm to about 100 µm, or about 38 µm to about 53 µm. In some embodiments, the carrier particles have a size distribution range of less than about 350 µm, less than about 250 µm, less than about 200 µm, less than about 150 µm, less than about 100 µm, less than about 53 µm, less than about 38 µm, less than about 25 µm, less than about 10 µm, or less than about 5 µm. In further embodiments, the carrier particles have a size distribution range of at least 5 µm, at least 10 µm, at least 20 µm, at least 25 µm, at least 38 µm, at least 53 µm, at least 75 µm, at least 100 µm, at least 150 µm, or at least 200 µm. In other embodiments, the carrier particles have a particle size distribution range of about 1 µm to about 10 µm, about 1 µm to about 5 µm, or about 2 µm to about 5 µm.

In still other formulations, two or more mean particle sizes or particle size distribution ranges of a carrier can be combined for use in a formulation. For example, a formulation can comprise of carrier particles having one group with a particle size range of less than about 25 µm and another group of particles with a range of about 100 µm to about 200 µm. Such combinations can be used in formulations where different sites are targeted for the administration (e.g., both intranasal and pulmonary administration).

The particle composition of a defined range, such as one that is composed of particles less than 100 µm, can be further described based on the percent composition of particles that make up sub-ranges within the defined range. For example, a defined particle range composed of particles less than 100 µm, can be further described to be composed of one group of particles with a diameter smaller than about 25 µm that make up 10 weight % or less of the defined range; a second group of particles with a diameter of about 25 µm to about 38 µm that make up 20% to 60 weight % of the defined range; a third group with a diameter greater than about 38 µm to about 53 µm that make up 20% to 60 weight % of the defined range; with a fourth group of particles that represent all particles having a diameter greater than 53 µm, but less than 100 µm.

Within any given particle size range, at least about 60%, at least about 70%, at least about 80%, at least about 90% or at least about 95% of the stated particles can have a size within the stated range. For example, when a carrier or other component is stated to have a particle size from about 20 µm to about 38 µm, at least 60%, 70%, 80%, 90% or 95% of the particles of the carrier or component have a particle size within this range.

In some embodiments, milling, grinding or other standard particle size reduction techniques are used to generate a desired particle size range for therapeutic agent and also for any of the remaining formulation components. In other embodiments, therapeutic agents of the desired size are produced by spray drying, micronisation, controlled precipitation methods (e.g. described in patent applications WO 00/38811 and WO 01/32125), through the use of supercritical fluids such as the rapid expansion of supercritical solutions (RESS), supercritical anti-solvent (SAS) and particles from gas saturated solutions (PGSS). The present invention provides no limitation on the method by which active agents are made suitable for administration by inhalation In some embodiments, the particle size reduction techniques are carried out separately for the therapeutic agent and the other components. Later, the therapeutic agent and the other components are blended or mixed together to produce the composition. In this way, it is possible to provide a composition or formulation in which the particle size of the therapeutic agent is larger or smaller than the particle size of, for example, the carrier or an excipient. The advantages of compositions of mixed particle size include the ability to design formulations wherein the therapeutic agent is deposited in a different anatomical location than the other components of the composition. A variation of this technique is possible when there are multiple therapeutic agents in a formulation. Each can be preferentially deposited in a different anatomical location based on its particle size range. For example, a composition with two therapeutic agents can be designed so that the lungs are targeted by one therapeutic agent through the use of particles with a size range of 1-5 μm, while the other nasal cavities can be targeted with the second therapeutic agent through the use of particles with a size range, 100-150 μm.

Other Carrier Properties

In some embodiments, the carrier particles are adhesion agents, i.e., they have properties that promote the adherence of the carrier and any entrained or bound therapeutic agent attached to the carrier to the nasal mucosa. Non-limiting examples of mucosal bioadhesives include, esterified hyaluronic acid, methylcellulose, sodium carboxymethylcellulose, hydroxypropyl-methylcellulose, chitosan glutamate, Carbopol 934P, polyethylene oxide 600K and Pluronic F127.

Bulk Density

Bulk density refers to the mass of particles that occupy a specific volume, usually expressed as g/cm$^3$. The volume includes particle volume, inter-particle void volume and internal pore volume. Bulk density is not an intrinsic property of a material and can change depending on how the material is handled. A freshly poured powder that settles on its own accord will have an "untapped" bulk density. When such a powder is disturbed, usually by vibration, the powder particles will move and settle closer together, resulting in a higher bulk density, usually referred to as the "tapped density."

A standardized technique for determining the "untapped" bulk density of a powder is described in Part I of Supplement I to Japanese Pharmacopoeia, Fourteenth Edition. More specifically, the density can be determined by pouring the sample evenly from above into a cylindrical vessel with an inner diameter of 46 mm and a height of 110 mm (measured volume, 180 ml) through a 1000-μm JIS standard sieve, and weighing the sample after smoothly leveling off the top of the vessel.

The untapped bulk density varies depending on particle size, shape, cohesion force, and such. In general, the untapped bulk density tends to decrease as the particle takes on a more irregular shape away from the sphere shape. Furthermore, as the particle diameter becomes smaller, the force of inter-particle cohesion, rather than the weight of particle itself, has more impact on the density, and thus the untapped bulk density tends to be smaller. In some embodiments, the carrier particles have an untapped bulk density of about 0.05 g/cm$^3$ to about 0.80 g/cm$^3$, 0.10 g/cm$^3$ to about 0.70 g/cm$^3$, 0.13 g/cm$^3$ to about 0.29 g/cm$^3$, about 0.21 g/cm$^3$ to about 0.28 g/cm$^3$, about 0.22 g/cm$^3$ to about 0.40 g/cm$^3$, about 0.26 g/cm$^3$ to about 0.48 g/cm$^3$, about 0.35 g/cm$^3$ to about 0.65 g/cm$^3$, about 0.30 g/cm$^3$ to about 0.46 g/cm$^3$, about 0.38 g/cm$^3$ to about 0.43 g/cm$^3$ or about 0.40 g/cm$^3$ to about 0.60 g/cm$^3$. In other embodiments, the carrier particles have an untapped bulk density of less than about 0.80 g/cm$^3$, of less than about 0.70 g/cm$^3$, of less than about 0.60 g/cm$^3$, of less than about 0.50 g/cm$^3$, of less than about 0.40 g/cm$^3$, of less than about 0.30 g/cm$^3$ or of less than about 0.20 g/cm$^3$. In still further embodiments, the carrier particles have an untapped bulk density of at least 0.10 g/cm$^3$, at least 0.20 g/cm$^3$, at least 0.30 g/cm$^3$, at least 0.40 g/cm$^3$, at least 0.50 g/cm$^3$, at least 0.60 g/cm$^3$, or at least 70 g/cm$^3$. In some embodiments the carrier particles have an untapped bulk density of about 0.20 g/cm$^3$, 0.21 g/cm$^3$, 0.22 g/cm$^3$, 0.23 g/cm$^3$, or 0.24 g/cm$^3$.

Specific Surface Area

Specific surface area is a material property of solids that measures the total surface area per unit of mass, or bulk volume. It is defined either by surface area divided by mass (with units of m$^2$/kg), or surface area divided by the volume (units of m$^2$/m$^3$ or m-1)

One way to measure the specific surface area is by the BET theory of the physical adsorption of gas molecules on a solid surface.

The Japanese Pharmacopoeia, Fourteenth Edition, Part I, describes a method for the calculation of the specific surface area of a material based on the BET formula from the amount of nitrogen molecules adsorbed onto the powder surface after six hours of pre-vacuation at a fixed temperature (77.35 Kelvin).

The specific surface area varies depending on particle size, surface properties, presence of pores, and the like. In general, as the particle diameter becomes smaller, the specific surface area tends to be greater. In some embodiments, the specific surface area is between about 0.4 m$^2$/g to about 6.0 m$^2$/g, 0.4 m$^2$/g to about 4.0 m$^2$/g, 0.4 m$^2$/g to about 2.0 m$^2$/g, about 2.0 m$^2$/g to about 3.5 m$^2$/g. 0.4 m$^2$/g to 1.3 m$^2$/g, 0.5 m$^2$/g to 1.0 m$^2$/g, 0.5 m$^2$/g to 1.3 m$^2$/g, or 0.7 m$^2$/g to 1.0 m$^2$/g. In some embodiments, the specific surface area of the particles is 1.3 m$^2$/g or less, 1.0 m$^2$/g or less, 0.80 m$^2$/g or less, 0.70 m$^2$/g or less, 0.60 m$^2$/g or less, 0.50 m$^2$/g or less, or 0.4.0 m$^2$/g or less. In further embodiments, the specific surface area of the particles is at least 0.4.0 m$^2$/g, at least 0.50 m$^2$/g, at least 0.60 m$^2$/g, at least 0.70 m$^2$/g, at least 0.80 m$^2$/g, at least 1.0 m$^2$/g, or at least 1.3 m$^2$/g.

Angle of Repose

The angle of repose is the maximum angle of a stable slope and is determined by friction, cohesion and the shapes of the particles. When bulk granular materials are poured onto a horizontal surface, a conical pile will form. The internal angle between the surface of the pile and the horizontal surface is known as the angle of repose. Material with a low angle of repose forms flatter piles than material with a high angle of repose. Generally, the angle of repose tends to increase as the particle diameter becomes smaller. The angle of repose serves as an indicator for powder flowability with a smaller angle of repose correlating with greater powder flowability.

The simplest method to determine the angle of repose is to pour the test material into a funnel set at fixed and know distance above the horizontal surface on which the pile will form and then measuring the angle formed by the outer surface of the pile with the horizontal surface. In some embodiments, the angle of repose is about 10° to about 80°, about 20° to about 70°, about 30° to about 60°, about 30° to about 50°, about 35° to about 55°, about 35° to about 45°, about 40° to about 53° or about 40° to about 50°. In some embodiments, the angle of repose is about 80° or less, about 70° or less, about 60° or less, about 55° or less, about 50° or less, about 45° or less, about 40° or less, about 35° or less, or about 30° or less. In further embodiments, the angle of repose is at least 30°, at least 35°, at least 40°, at least 45°, at least 50°, at least 55°, at least 60°, or at least 70°.

Degree of Polymerization

The degree of polymerization is the number of repeating units or monomers in an average polymer chain. With carbohydrates, including celluloses, the monomer is a sugar. In some embodiments, the average degree of polymerization of a polymer carrier is about 20 to about 600, about 20 to about 500, about 20 to about 400, about 20 to about 300, about 20 to about 250, or about 20 to about 200. In other embodiments, the degree of polymerization is less than 600, less than 550, less than 500, less than 450, less than 400, less than 350, less than 300, less than 250, less than 200, less than 150, or less than 100. In further embodiments, the degree of polymerization is at least 100, at least 150, at least 200, at least 250, at least 300, at least 350, at least 400, at least 450 or at least 500.

Carrier Free

In some embodiments, it is possible or desirable to use therapeutic agent in its native or processed form without the addition of a carrier agent. Such compositions and formulations are known as "carrier free."

Excipients

Frequently, the addition of other materials to a therapeutic agent is desirable. Besides carriers, other inactive material or combination of materials that are suitable for inhalation, "excipients", can be added to the composition or formulation. Frequently excipients serve to improve the features of the therapeutic agent composition, e.g., by providing more efficient and reproducible delivery of the therapeutic agent, improving the handling characteristics of powders (e.g., flowability and consistency), the stability of the agent, and/or facilitating manufacturing and filling of unit dosage forms. In particular, excipient materials may function to further improve the physical and chemical stability of the therapeutic agent, aid in adhesion or binding the formulation or therapeutic particle into the nasal and/or pulmonary mucosal layer, and enhance uptake of the therapeutic agent into the mucosal and/or avioli cells, thus increasing efficacy of the therapeutic agent. Excipients may further serve to minimize the residual moisture content and/or hinder moisture uptake, minimize particle aggregation, modify particle surface properties (i.e., rugosity), increase the ease of inhalation, improve and the targeting of particles to the sinuses and/or lung. An excipient may also serve as a bulking agent when it is desired to reduce the concentration of therapeutic agent in the formulation. Furthermore, an excipient may server as a masking agent for objectionable smells and/or tastes.

Useful excipients that may be added to the compositions and formulations of the invention include, but are not limited to, fluidizers, lubricants, adhesion agents, surfactants, acidifying agents, alkalizing agents, agents to adjust pH, antimicrobial preservatives, antioxidants, anti-static agents, buffering agents, chelating agents, humectants, gel-forming agents, or wetting agents. Excipients also include coloring agents, coating agents, sweetening, flavoring and perfuming and other masking agents. The compositions and formulations of this invention may include a therapeutic agent with an individual excipient or with multiple excipients in any suitable combination, with or without a carrier. In some embodiments, a fluidizer is added to the intranasal compositions to improve the flowability of the composition. Typically, fluidizers help prevent compositions from aggregating or clumping and allow for improved powder handling. Use of fluidizers may increase capsule filling efficiency and consistency along with increasing dose administration consistency and efficiency of the nasal administration devices. Examples of fluidizers include tribasic calcium phosphate, magnesium sterate, or disclosed in U.S. Pat. No. 5,098,907, anhydrous silicic acid. Fluidizing agents can be used alone or in combination. In some embodiments, tribasic calcium phosphate is used. Generally, the percentage of tribasic calcium phosphate in a formulation ranges from about 0.1 to about 10 (W/W) %. In some embodiments, increased fluidizing effect results when tribasic calcium phosphate is combined with two or more sizes of one carrier or optionally, different materials as disclosed in International Application No. PCT/JP2007/074787.

Examples of lubricants include magnesium stearate. pH adjusting agents include, for example, dibasic sodium phosphate, citric acid, and sodium citrate. Examples of pharmaceutically acceptable antioxidants include water soluble antioxidants such as ascorbic acid, cysteine hydrochloride, sodium bisulfate, sodium metabisulfite, sodium sulfite and the like, while examples of oil-soluble antioxidants such include ascorbyl palmitate, butylated hydroxyanisole (BHA), butylated hydroxytoluene (BHT), lecithin, propyl gallate, alpha-tocopherol and the like. Examples of preservatives include, for example, benzalkonium chloride.

Suitable antistatic agents may be selected from, for example, sorbitan fatty acid esters, polyoxyelhylene sorbitan fatty acid esters, dioctyl sodium sulphosuccinate, and fatty amine salts of alkylarylsulphonic acids. Suitable anti-static agents are also disclosed in International Application WO 94/04133.

In some embodiments, adhesion agents are bioadhesion and/or mucoadhesion promoting agent. In some embodiments, the adhesion agents are carrier particles, while in other embodiments, the adhesion agents coat the carrier particles or the therapeutic agent. Alternatively, the adhesion agent may be added to the formulation in its free state unbound to the carrier or drug. Bioadhesion and/or mucoadhesion agents increase the adherence of a therapeuticagent or agents to the nasal mucosa. Generally, the bioadhesion and/or mucoadhesion promoting agents swell and expand when placed in contact with water.

Typically, bioadhesion and/or mucoadhesion promoting agent is a polymeric substance that can be hydrated leading to swelling of the polymer. Generally, the faster the swelling of the polymer, the faster is the initiation of bioadhesion and/or mucoadhesion. Usefully bioadhesion and/or mucoadhesion promoting agents are disclosed in U.S. Patent Application Serial No. 20060216352.

Examples of buffering agents include magnesium hydroxide and aluminum hydroxide. Examples of chelating agents include citric acid, ethylenediamine tetraacetic acid (EDTA), sorbitol, tartaric acid, and phosphoric acid. Useful surfactants include bile acid surfactants as disclosed in U.S. Pat. No. 6,815,424 or phosphatidylcholines, such as dipalmitoylphosphatidylcholine, diphosphatidyl glycerol, hexadecanol, fatty alcohols such as polyethylene glycol, polyoxyethylene-9-lauryl ether, a surface active fatty acid, such as palmitic acid or oleic acid, or other surfactants as disclosed in U.S. Pat. No. 5,855,913.

In some embodiments of the invention, a water-absorbing and gel-forming material is added to the composition to improve drug absorption. Typically, this gel-forming material is used as a carrier, either alone or in combination with a water-absorbing, but non-gel-forming substance. Exemplary, gel-forming material include for example cellulose derivatives such as hydroxypropyl cellulose, hydroxypropyl methyl cellulose, methyl cellulose, hydroxy ethyl cellulose, and carboxymethyl cellulose sodium. Further disclosure of water-absorbing and gel-forming material and their use is found in U.S. Pat. No. 6,835,389.

Representative examples of wetting agents include, for example, gelatin, casein, lecithin (phosphatides), gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters (e.g., TWEEN™), polyethylene glycols, polyoxyethylene stearates, colloidal silicon dioxide, phosphates, sodium dodecylsulfate, carboxymethylcellulose calcium, carboxymethylcellulose sodium, methylcellulose, hydroxyethylcellulose, hydroxy propylcellulose, hydroxypropylmethylcellulose phthlate, noncrystalline cellulose, magnesium aluminum silicate, triethanolamine, polyvinyl alcohol, and polyvinylpyrrolidone (PVP).

Useful sweetening agents include, for example, D-sorbitol, glycyrrhizia, saccharin, and stevia.

It should be appreciated that there may be considerable overlap in function of excipients used in the powdered compositions and formulations described herein. Thus, the categorization of the above-listed excipients should be taken as merely exemplary, and not limiting, of the types of excipients that are included in the powdered compositions and formulations described herein. Further examples of pharmaceutical excipients and/or additives of the above categories suitable for use in the compositions and formulations of this invention can be found in the U.S. Pharmacopeia National Formulary, 1990, pp. 1857-1859, as well as in Raymond C. Rowe, et al., Handbook of Pharmaceutical Excipients, 5th ed., 2006, and "Remington: The Science and Practice of Pharmacy," 21st ed., 2006, editor David B. Troy, and in the Physician's Desk Reference, 52nd ed., Medical Economics, Montvale, N.J., 1998.

Generally, pharmaceutical excipients, if present, range in amounts from about 0.01% to about 95% by weight. More typically, excipients range from about 0.5 to about 80%, about 1.0% to about 50%, or about 5% to about 30% by weight of the composition.

Therapeutic agents, carriers, excipients, and other components may require grinding, milling, spray drying, or some other processing step before use. Frequently, the required processing converts the therapeutic agents into particles with a desired median size and/or a defined particle size distribution ranges. In some embodiments, the native or processed therapeutic agents carriers, excipients, and other components are suitable for intrapulmonary or intranasal use, as is. In other embodiments, these ingredients require further processing, such as sieving, to achieve the desired or necessary particle size distributions.

Formulations

In some embodiments, intranasal formulations with the following general carrier and fluidizer composition are used. Tribasic calcium phosphate in the range of 0.1 to 10 (W/W) %; a first crystalline cellulose with an average particle diameter of 150 μm at 5.0 to 30 (W/W) %; a second crystalline cellulose with an average particle diameter of 30 μm or less making up the remainder of the composition. To this is added the therapeutic agent at a weight ratio of 0.0001 to 1.2 to the fluidizer/carrier composition when the therapeutic agent is taken as its free form equivalent weight. Useful crystalline cellulose that has an average particle diameter of 150 μm include Ceolus® and Avicel® PH-101, PH-102, PH-301, and PH-302 from Asahi Kasei Chemicals (Japan) Corporation and FMC Corporation (US). Useful crystalline cellulose that has an average particle diameter of 30 μm or less include Ceolus®PH-F20JP.

Alternately, the first crystalline cellulose can be replaced with a starch that has an average particle diameter of 150 μm or less. Useful starch include cornstarch (Merck). Additionally information on preferred formulations can be found in PCT/JP2007/074787.

Drugs

In some embodiments, the dry powder composition or formulation comprises a therapeutic agent comprising a small molecule, a peptide drug, a protein drug, a cytokine, a vaccine, an allergen, nucleic acid, or a vitamin. In some embodiments, small molecules include, for example, analgesic agents such as morphine, fentanyl, oxycodone, butorphanol, and tramadol; antiemetic agents such as granisetron, ondansetron, tropisetron, palonosetron, and indisetron; antimigraine agents such as sumatriptan, zolmitriptan, rizatriptan, naratriptan, and ergotamine; sleep-inducing agents such as triazolam and melatonin; anticonvulsants such as carbamazepine; sedatives such as midazolam; antidementia agents such as donepezil; brain activators such as tiapride; antibiotics such as cefaclor; antibacterial agents such as enoxacin; antiviral agents such as aciclovir, zidvudine, didanosine, nevirapine, and indinavir; muscle relaxants such as dantrolene; cardiac stimulants such as digoxin; therapeutic agents for Parkinson's disease such as trihexyphenidyl and biperiden; antitussive agents and expectorants such as dextromethorphan; respiratory stimulants such as naloxone; antidinic agents such as betahistine; angiotonic agents such as naphazoline; coronary vasodilators such as diltiazem; therapeutic agents for asthma such as tranilast; antidiarrheal agents such as loperamide; NSAIDs such as diclofenac; steroids such as beclomethasone; antihistamic agents such as chlorpheniramine; agents for improvement in sexual function such as sildenafil and vardenafil; hair growing agents such as finasteride; antianaphylactic agents such as epinephrine; and antitumor agents such as 5-FU. Preferred small molecules include morphine, granisetron, ondansetron, fentanyl, oxycodone, sumatriptan, zolmitriptan, beclomethasone, and ketotifen.

In some embodiments, peptide and protein drugs include, for example, insulin, growth hormone, growth hormone releasing peptide, ghrelin, glucagon, calcitonin, interferon, erythropoietin, interleukin, PTH(1-84), PTH(1-34), PTH-related peptides, GLP-1, vasopressin, leuprorelin, granulocyte-colony stimulating factor, prolactin, human menopausal gonadotropin, chorionic gonadotropin, follicle stimulating hormone, luteinizing hormone, leptin, nerve growth factor (NGF), stem cell growth factor (SCGF), keratinocyte growth factor (KGF), thioredoxin, cyclosporin, influenza vaccine, and analogs thereof. Preferred peptide and protein drugs include insulin, PTH(1-34), and human menopausal gonadotropin.

In some embodiments, nucleic acids include, for example, DNA, RNA; RNAi; siRNA; and antisense DNA. In other embodiments, allergens include, for example, pollen, mold spores, latex, fur, dander and other environmental agents.

In some embodiments, antigens including proteins from pathogens, recombinant proteins, peptides, polysaccharides, conjugated polysaccharides, glycoproteins, lipopolysaccharides, inactivated toxins and polynucleotides, including naked DNA. In other embodiments, whole cells or viruses are used as antigens. In some embodiments, the cells or viruses are selected from inactivated whole viruses, disrupted viruses, or parts thereof. Cells include bacteria, fungi, other microorganisms, single cell parasites and parts thereof.

Exemplary antigens include but are not limited to influenza virus antigens (such as haemagglutinin and neuraminidase antigens), *Bordetella pertussis* antigens (such as pertussis toxin, filamentous haemagglutinin, pertactin), human papilloma virus (HPV) antigens, *Helicobacter pylori* antigens, rabies antigens, tick-borne encephalitis (TBE) antigens, meningococcal antigens (such as capsular polysaccharides of serogroup A, B, C, Y and W-135), tetanus antigens (such as tetanus toxoid), diphtheria antigens (such as diphtheria toxoid), pneumococcal antigens (such as *Streptococcus pneumoniae* type 3 capsular polysaccharide), tuberculosis antigens, human immunodeficiency virus (HIV) antigens (such as GP-120, GP-160), cholera antigens (such as cholera toxin B subunit), staphylococcal antigens (such as staphylococcal enterotoxin B), *shigella* antigens (such as *shigella* polysaccharides), vesicular stomatitis virus antigen (such as vesicular stomatitis virus glycoprotein), cytomegalovirus (CMV) antigens, hepatitis antigens (such as hepatitis A (HAV), B (HBV), C(HCV), D (HDV) and G (HGV) virus antigens), respiratory syncytial virus (RSV) antigens, herpes simplex antigens, or combinations thereof (e.g. combinations of diphtheria, pertussis and tetanus (DPT)). Suitable antigens also include those delivered for induction of tolerance, such as retinal antigens.

In some embodiments, adjuvants are co-administered with vaccine antigens, to further boost the effectiveness of vaccine compositions by stimulating the immune response (see e.g. Hibberd et al., Ann. Intern. Med., 110, 955 (1989)). Examples of adjuvants that have been shown to be effective include interferon alpha, *Klebsiella pneumoniae*, glycoprotein, and interleukin-2.

Vaccine are administered to a patient in an amount effective to stimulate a protective immune response. For example, the vaccine may be administered to humans in one or more doses, each dose containing 1-250 micrograms and more preferably 2-50 micrograms of an antigen. For example, where haemagglutinin and neuraminidase preparations are prepared from three virus strains, e.g. 2× Influenza A and I× Influenza B, a total dose of viral protein administered may be in the range 15-150 micrograms. Where *Bordetella persussis* antigens are employed, a total dose of bacterial protein administered as FHA, pertussis toxin (toxoid) or pertactin, either individually or in combination may be in the range 5-150 micrograms.

Percent Composition

In general, dry powder compositions for intranasal administration will contain from about 0.01% by weight to about 99% by weight therapeutic agent. In some embodiments, the dry powder will contain from about 0.1% to about 95%, about 0.5% to about 90%, about 1.0% to about 80%, about 2% to about 75%, about 5% to about 50%, about 10% to 30% by weight the therapeutic agent. In other embodiments, the dry powder composition will contain at least 5%, 10%, 15%, 20%, 25%, 30%, 40%, 50%, 60%, 70%, or 80% by weight the therapeutic agent. In further embodiments, the intranasal powdery medicine will contain less than 90%, 80%, 70%, 60%, 50%, 45%, 40%, 35%, 30%, 25%, 20%, 15% or 10%. The percentage composition will vary depending upon the weight of the specific therapeutic agent and also on the relative amounts of carriers, excipients, or other additives contained in the composition. In some embodiments, two or more therapeutic agents are combined in the formulation.

The dry powder formulations may be carrier free, i.e., contain only one or more therapeutic agents, but more typically, the formulations are a blend or mixture of the therapeutic agent with a carrier and, if desired, one or more excipients. The powder formulation may, if desired, be portioned and/or otherwise processed into unit dose quantities, e.g., portioned into unit dose quantities and individually placed within a dosage form or drug delivery system. Although any dosage form that contains a unit dose of the formulation is acceptable, capsules and single use devises are preferred. The capsule material may be either hard or soft, and, as will be appreciated by those skilled in the art, typically comprises a water-soluble compound such as gelatin, starch or a cellulosic material. Preferably, the capsules are composed of a cellulosic material, e.g., hydroxypropyl methylcellulose (HPMC). The capsules may be sealed, such as with gelatin bands or the like. See, for example, Remington. The Science and Practice of Pharmacy, supra, which describes materials and methods for preparing encapsulated pharmaceuticals. Methods for filling large numbers of cavities (i.e., unit dose packages) with metered doses of dry powder medicament are described, for example, in WO 97/41031. Each capsule or unit dosage form will typically contain a therapeutically effective dose of each therapeutic agent. Alternatively, the dosage forms may contain less than a therapeutically effective dose in which case administration of two or more dosage forms would be required to achieve the therapeutically effective dose.

Additionally, the powder formulation may be loaded into a dosage form or drug delivery device and not "metered out" into unit doses until used. Furthermore, the dry powder formulation may be preloaded into a device, typically, a disposable or single use device.

Usually, dry powders bulk or unit dosage forms are stored under ambient conditions, and may be stored at temperatures at or below about 25° C. and relative humidities (RH) ranging from about 15 to 80%. RH of less than about 40% can be achieved using a dessicating agent in the secondary packaging of the dosage form.

The compositions of the invention are particularly useful for therapeutic agents that are delivered in doses of from about 0.001 mg/kg/day to about 100 mg/kg/day, from about 0.01 mg/kg/day to about 75 mg/kg/day, from about 0.10 mg/kg/day to about 50 mg/kg/day, or from about 5 mg/kg/day to about 20 mg/kg/day.

Intranasal Pharmaceutical Administration

The compositions and formulations of this invention may be delivered using any suitable dry powder inhaler (DPI), i.e., an inhaler device that utilizes the patient's inhaled breath as a vehicle to transport the dry powder to the nasal passages, sinosoidal spaces, and/or lungs. In some embodiments, the pharmaceutical formulation is contained in a receptacle such as a capsule, a blister package or cartridge. Typically, the receptacle has a puncturable lid or other access surface. In some embodiments, the receptacle may contain a single dosage unit or multiple dosage units.

Suitable devices for delivering the powders described herein that use a capsule are described, for example, in U.S. Pat. No. 3,906,950, U.S. Pat. No. 4,013,075, U.S. Pat. No. 7,278,982 and U.S. Pat. No. 7,353,823.

In some embodiments, the dry powder inhaler is engineered to be disposable and/or single use and comes preloaded with the dry powder formulation. In some embodiments, use of the disposable dry powder inhaler only requires the user to snap off or remove a lid to be able to administer the formulation rather than rupturing or broaching a capsule or blister.

Dry powders may also be delivered using a pressurized, metered dose inhaler (MDI), e.g., the Ventolin™ metered dose inhaler, containing a solution or suspension of drug in a pharmaceutically inert liquid propellant, e.g., a chlorofluorocarbon or fluorocarbon, as described in U.S. Pat. No. 5,320, 094, and in U.S. Pat. No. 5,672,581.

Indications

In some embodiments, a therapeutic agent is administered prior to, concurrently with or subsequent to the appearance of symptoms of a disease, condition or disorder. In other embodiments, a therapeutic agent is administered to a subject with a family history of the disease, condition or disorder, or who has a phenotype or genotype that indicates a predisposition to a disease, condition or disorder. In some embodiments, the therapeutic agent is administered with the intent to alleviate, ameliorate, or otherwise reduce the symptoms of a disease, condition, or disorder. In other embodiments, the therapeutic agent is administered therapeutically with the intent to cure, control or reverse the underlying disease process. In still other embodiments, the therapeutic agent is administered with the prophylactically with the intent to prevent or forestall the occurrence of a disease, condition, or disorder. In some embodiments, the disclosed compositions and formulations may also contain other therapeutic agents that are selected for their therapeutic value for the condition to be treated.

Taste Reduction

Generally, the salt forms of drugs have disagreeable tastes, often of a bitter nature. With pulmonary administration, the patient usually inhales the pharmaceutical formulation through the mouth resulting in the direct or indirect exposure of the tongue. With intranasal administration, the drug exposure of the tongue is usually indirect. The disagreeable taste of the salt forms of drugs is unpleasant and may make patients reluctant to take their medication or even lead to non-compliance with patients skipping doses or stopping therapy prematurely.

In contrast, the pulmonary or intranasal administration of a pharmaceutical formulation of a freebase drug is generally much better accepted by patients because such formulations usually do not taste so objectionably. In some embodiments, the freebase drug compositions are tasteless or have substantially no discernable taste. In other embodiments, the freebase drug composition may have a slightly discernable taste. In some embodiments, the degree of discernable taste of a freebase drug composition is less than about $\frac{1}{2}$, $\frac{1}{3}$, $\frac{1}{4}$, $\frac{1}{5}$, $\frac{1}{10}$, $\frac{1}{20}$, $\frac{1}{50}$, $\frac{1}{100}$, $\frac{1}{500}$, or $\frac{1}{1000}$ of the taste of the salt form of the drug composition.

What little taste that may be present in a freebase drug composition may be more readily masked with added flavors, fragrances, sweeteners and/or other masking agents. In some embodiments, the amount of flavor and/or fragrances needed to mask an objectionable taste is reduced compared to the salt form of a drug composition. In some embodiments, the reduction in required flavors and/or fragrances needed to mask an objectionable taste is less than about $\frac{1}{2}$, $\frac{1}{3}$, $\frac{1}{4}$, $\frac{1}{5}$, $\frac{1}{10}$, $\frac{1}{20}$, $\frac{1}{50}$, $\frac{1}{100}$, $\frac{1}{500}$, or $\frac{1}{1000}$ of the amount needed to mask an objectionable taste in the salt form of a drug composition.

The lack or reduced presence of an objectionable taste, or the ability to effectively mask an objectionable taste may result in patients not becoming adverse to regularly taking their medications and may reduce or prevent patient non-compliance.

Mixtures of the salt and freebase form of a drug may also have a substantially reduced taste compared to the salt form. The intensity of an objectionable taste may depend on the ratio of the salt to freebase form were generally, the higher the ratio of salt to freebase, the greater the intensity of the objectionable taste. In some instances, intranasal pharmaceutical formulation with a salt to freebase ratio of 3:1, 2:1, 1:1, 1:2, 1:3, 1:4, 1:5, 1:10, 1:20, 1:50, 1:100, 1:500, or 1:1000 may have a reduced degree of objectionable taste compared to an intranasal pharmaceutical formulation with 100% of the therapeutic agent in salt form.

The presence and degree of an objectionable taste can be quantified by placing compositions with a standard total molar quantity of a drug, but varying in the ratio of salt to freebase, on the tongues of testers.

Kits/Articles of Manufacture

For use of the therapeutic compositions described herein, kits and articles of manufacture are also described herein. In some embodiments, such kits include a carrier, package, or container that is compartmentalized to receive one or more blister packs, bottles, tubes, capsules, and the like. In certain embodiments, the pharmaceutical compositions are presented in a pack or dispenser device which contains one or more unit dosage forms containing a compound provided herein. In other embodiments, the pack contains metal or plastic foil, such as a blister pack. In some embodiments, the pack contains capsules, vials, or tubes. In other embodiments, the pack or dispenser device is accompanied by instructions for administration. In some embodiments, the dispenser is disposable or single use, while in other embodiments, the dispenser is reusable. In certain embodiments, the pharmaceutical formulations are preloaded into the device.

In still other embodiments, the pack or dispenser also accompanied with a notice as required by a governmental agency regulating the manufacture, use, or sale of pharmaceuticals. This notice states that the drug is approved by the agency for human or veterinary administration. Such notice, for example, is the labeling approved by the U.S. Food and Drug Administration for prescription drugs, or the approved product insert. Compositions containing a compound provided herein formulated in a compatible pharmaceutical carrier are also prepared, placed in an appropriate container, and labeled for treatment of an indicated condition.

The articles of manufacture provided herein may also contain an administration or dispensing device. Examples of administration devices include pulmonary inhalers and intranasal applicators. Pumps may be provided with the inhalers and intranasal devices, or the pumps may be built into the devices. Alternatively, a propellant may be included with or it may be stored within the devices.

Such kits optionally comprise an identifying description or label for the containers. In further embodiments, the label is on a container with letters, numbers or other characters forming the label and attached, molded or etched into the container itself; a label is associated with a container when it is present within a receptacle or carrier that also holds the container, e.g., as a package insert. In some embodiments, a label is used to indicate that the contents are to be used for a specific therapeutic application. In yet other embodiments, the label also indicates directions for use of the contents, such as in the methods described herein. In some embodiments, a set of instructions may also be included, generally in the form of a package insert. The informational material may contain instructions on how to dispense the pharmaceutical composition, including description of the type of patients who may be treated, the schedule (e.g., dose and frequency), and the like.

Methods for Developing Inhalable Dry Powder Compositions

Inhalable dry powder compositions with improved pharmacokinetic profiles can be developed through a number of methodologies. In one embodiment, a plurality of inhalable dry powder pharmaceutical compositions are tested in animals, particularly mammals and more particularly, primates. Generally, the pharmaceutical compositions should be identical in their composition but vary by one, two, or three chemical or physical parameters, usually that of the therapeutic agent. Typically, the parameters that are studied include percentage of freebase, and the size of the freebase or salt particles. A constant molar quantity of the therapeutic agent should be present in all of the test compositions.

Blood is serially drawn at specific time points from the test subjects and the concentration of the drug or associated metabolite are determined. Then the pharmacokinetic profiles of the compositions including Cmax, Tmax, $T_{1/2}$), and BA are calculated and compared. From the data, the chemical or physical parameters of the compositions can be changed to further explore noted trends or characteristics. For example, if in otherwise identical compositions, a composition of a freebase drug with an average particle size of 50 µm has a Cmax that is 80% of that seen with the salt form of the drug, then for the next study, a composition can be tested that has the freebase drug in an average particle size of 20 µm to see if the Cmax is further increased. In this manner a composition can be further refined to achieve a desired pharmacokinetic profile.

EXAMPLES

The practice of the present invention will employ, unless otherwise indicated, conventional techniques of pharmaceutical formulation and the like, which are within the skill of the art. Such techniques are explained fully in the literature. The examples given herein, and the exemplary language used herein are solely for the purpose of illustration, and are not intended to limit the scope of the invention. When a list of examples is given, such as a list of compounds or molecules suitable for this invention, it will be apparent to those skilled in the art that mixtures of the listed compounds or molecules are also suitable.

In the following examples, efforts have been made to ensure accuracy with respect to numbers used (e.g., amounts, temperature, etc.) but some experimental error and deviation should be accounted for. Unless indicated otherwise, temperature is in degrees C. and pressure is at or near atmospheric. All reagents were obtained commercially unless otherwise indicated.

Example 1

Sumatriptan Studies (Monkey Studies)

Figure 2:
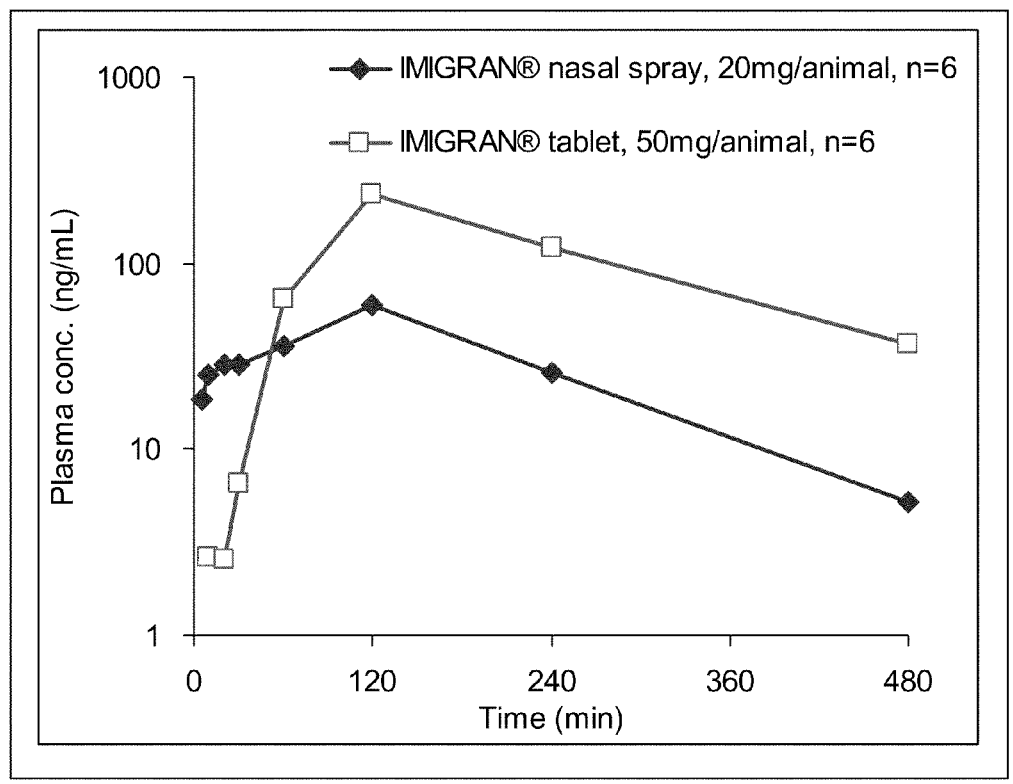
FIG. 2 illustrates the effect of the route of administration and type of formulation on the pharmacokinetic profile of sumatriptan succinate in monkeys.

Sumatriptan Pharmacokinetics—Comparison Between Oral Administration and a Liquid Nasal Spray The pharmacokinetics of sumatriptan were studied in two groups of rhesus monkeys. One group, n=6, was administered sumatriptan (IMGRAN®) in tablet form, 50 mg/animal, while the other group, n=6, was administered sumatriptan (IMGRAN®) as a nasal spray, 20 mg/animal. Blood was obtained at 10, 20, 30, 60, 120, 240, and 480 minutes post-administration from the monkeys administered the solid dosage form. For the monkeys treated with the nasal spray, blood was obtained 5, 10, 20, 30, 60, 120, 240, and 480 minutes post-treatment. The concentration of plasma sumatriptan was determined for both groups and then the data was processed to calculate the pharmacokinetic parameters for the groups and to construct a graph of the plasma concentration versus time curves (FIG. 2). Oral administration produced a Tmax of 120 minutes, a Cmax of 80 ng/ml, a T½ of, and an AUC of Intranasal administration produced a Tmax of 120 minutes, a Cmax of 48 minutes, a T½ of 104 minutes and an AUC of 11,063 ng:min/ml.

Figure 3:
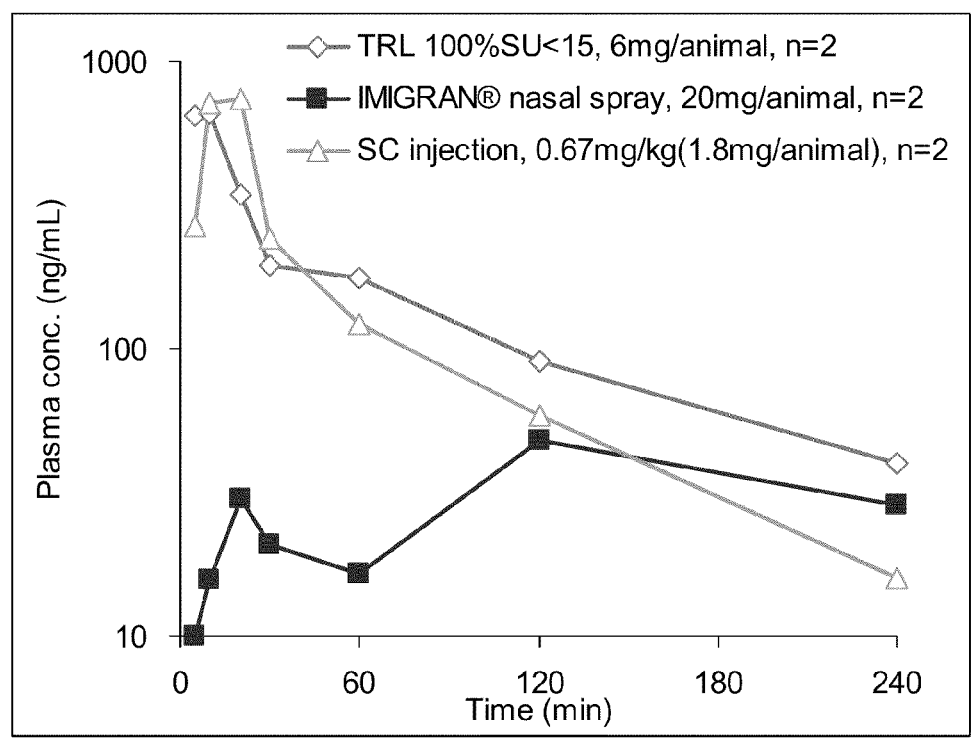
FIG. 3 illustrates the effect of the route of administration and formulation on the pharmacokinetic profile of sumatriptan succinate in monkeys.

Sumatriptan Pharmacokinetics—Comparison Between Subcutaneous Injection, Liquid Nasal Spray, an Intranasal Dry Powder Comprising Sumatriptan as the Succinate Salt The pharmacokinetics of sumatriptan were studied in three groups of rhesus monkeys. One group, n=2, was administered sumatriptan succinate by subcutaneous injection at 0.67 mg/kg, 1.8 mg/animal. A second group, n=2, was administered sumatriptan (IMGRAN®) as a nasal spray, 20 mg/animal. A third group, n=2, was administered sumatriptan succinate as a dry powder at 6 mg/animal. The particle size of the sumatriptan succinate was <15 µm. Blood was obtained at 5, 10, 20, 30, 60, 120, and 240 minutes post-administration. The concentration of plasma sumatriptan was determined for all groups and then the data was processed to calculate the pharmacokinetic parameters for the groups and to construct a graph of the plasma concentration versus time curves (FIG. 3).

Figure 4:
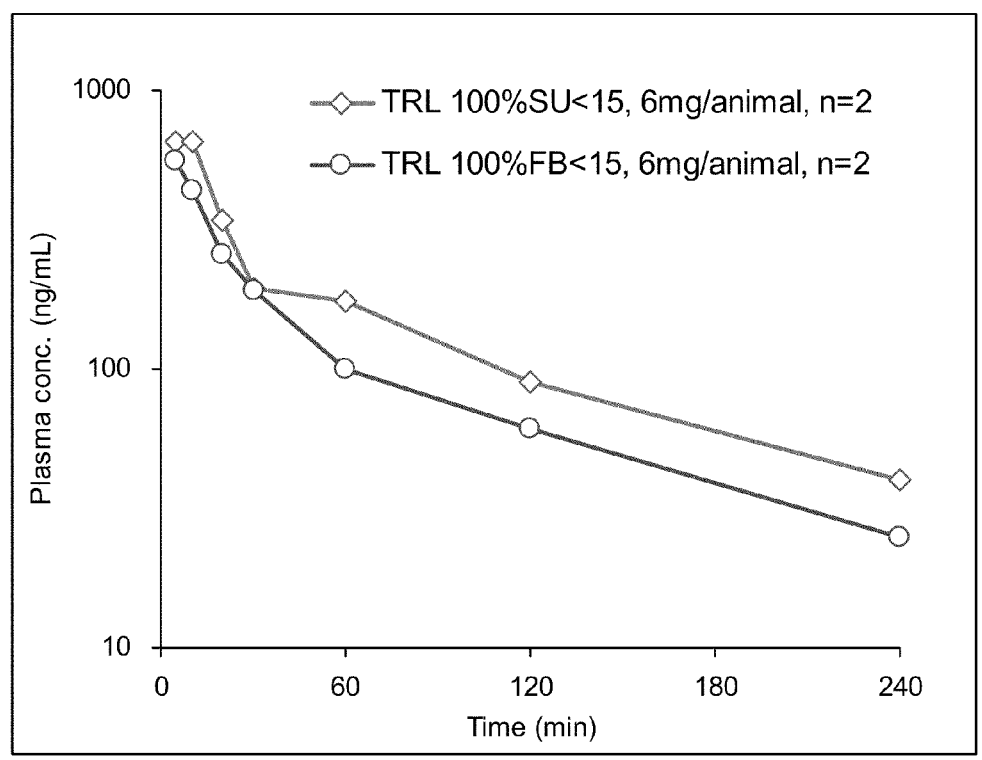
FIG. 4 illustrates the pharmacokinetic profiles of intranasally administered sumatriptan succinate and sumatriptan freebase formulations in monkeys.

Sumatriptan Pharmacokinetics—Comparison Between Intranasal Dry Powder Formulations: Succinate Versus Freebase The pharmacokinetics of sumatriptan dry powder formulations were studied in two groups of rhesus monkeys. One group, n=2, was administered intranasal sumatriptan succinate with a particle size of <15 µm. Administered dose was 6 mg/animal. A second group, n=2, was administered intranasal sumatriptan freebase, 6 mg/animal. The particle size of the sumatriptan freebase was <15 µm. Blood was obtained at 5, 10, 20, 30, 60, 120, and 240 minutes post-administration. The concentration of plasma sumatriptan was determined for both groups and then the data was processed to calculate the pharmacokinetic parameters for the administration groups and to construct a graph of the plasma concentration versus time curves (FIG. 4). Intranasal sumatriptan succinate produced a Tmax of 7.5 minutes, a Cmax of 696 ng/ml, a T½ of 114, and an AUC of 2632 ng:min/ml. Intranasal sumatriptan freebase produced a Tmax of 7.5 minutes, a Cmax of 612 ng/ml, a T½ of 119 minutes and an AUC of 1827 ng:min/ml.

Figure 5:
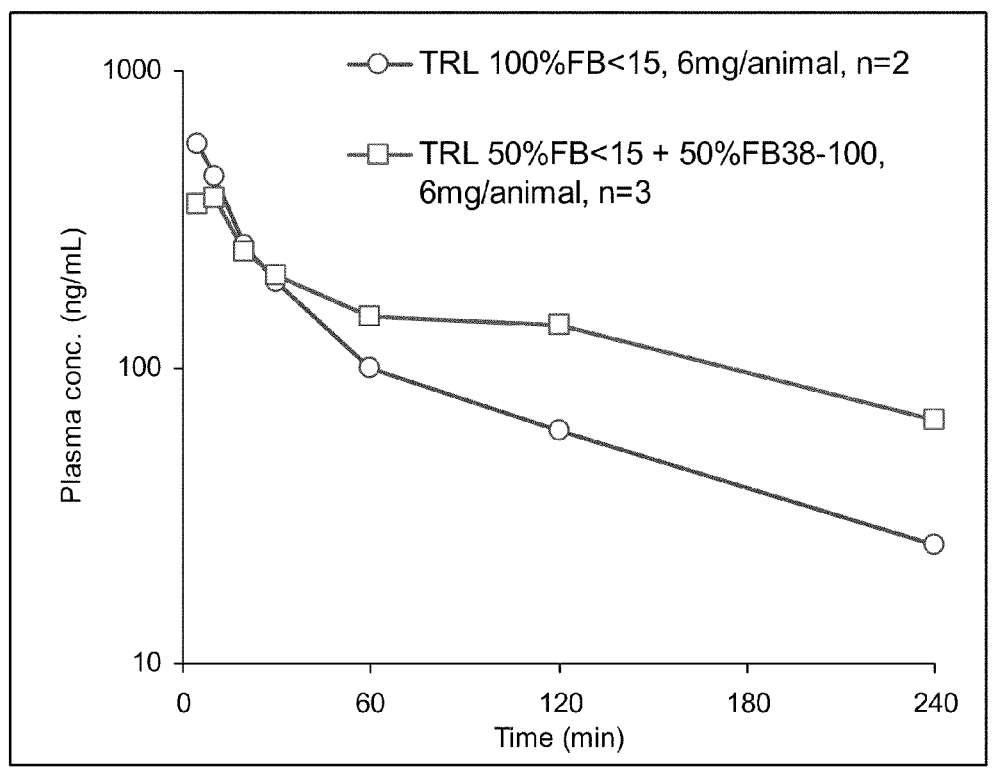
FIG. 5 illustrates the pharmacokinetic profiles of intranasally administered freebase sumatriptan formulations that differ only in their particle size distribution range.

Sumatriptan Pharmacokinetics—Comparison Between Intranasal Dry Powder Formulations: Effect of Freebase Particle Size on Pharmacokinetics The pharmacokinetics of sumatriptan dry powder formulations were studied in two groups of rhesus monkeys. One group, n=2, was administered intranasal sumatriptan freebase with a particle size of <15 µm. Administered dose was 6 mg/animal. A second group, n=2, was administered intranasal sumatriptan freebase as a mixture of 50% freebase with a particle size of <15 µm and 50% freebase with a particle size of 38 µm-100 µm. Administered dose was 6 mg/animal. Blood was obtained at 5, 10, 20, 30, 60, 120, and 240 minutes post-administration. The concentration of plasma sumatriptan was determined for both groups and then the data was processed to calculate the pharmacokinetic parameters for the administration groups and to construct a graph of the plasma concentration versus time curves (FIG. 5). Intranasal sumatriptan freebase with a particle size of <15 µm produced a Tmax of 7.5 minutes, a Cmax of 696 ng/ml, a T½ of 114, and an AUC of 2632 ng:min/ml. Intranasal sumatriptan freebase with 50% of the particles <15 µm and 50% of the particles 38 µm-100 µm produced a Tmax of 7.6 minutes, a Cmax of 373 ng/ml, a T½ of 119 minutes and an AUC of 1827 ng:min/ml.

Figure 6:
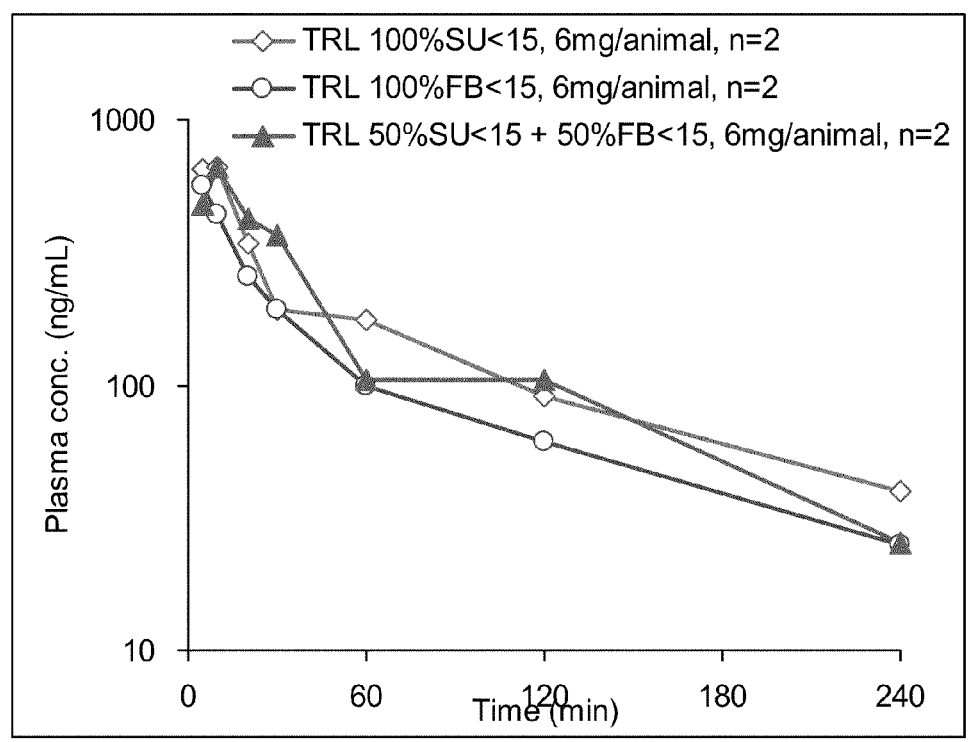
FIG. 6 illustrates the pharmacokinetic profiles of intranasally administered sumatriptan succinate, freebase sumatriptan, and a 50:50 mixture of sumatriptan succinate and sumatriptan freebase formulations. The particle size distribution range of the different sumatriptan formulations are the same, <15 μm.

Sumatriptan Pharmacokinetics—Comparison Between Intranasal Dry Powder Formulations: Effect of Succinate/Freebase with Small Particle Size The pharmacokinetics of sumatriptan dry powder formulations with a particle size of <15 µm were studied in three groups of rhesus monkeys. One group, n=2, was administered intranasal sumatriptan succinate at a dose of 6 mg/animal. A second group, n=2, was administered intranasal sumatriptan freebase at a dose of 6 mg/animal. A third group was administered a mixture of 50% sumatriptan succinate and 50% sumatriptan freebase. Total dose was 6 mg/animal. Blood was obtained at 5, 10, 20, 30, 60, 120, and 240 minutes post-administration. The concentration of plasma sumatriptan was determined for all groups and then the data was processed to calculate the pharmacokinetic parameters and to construct a graph of the plasma concentration versus time curves (FIG. 6). Intranasal sumatriptan succinate produced a Tmax of 7.5 minutes, a Cmax of 696 ng/ml, a T½ of 114, and an AUC of 2632 ng:min/ml. Intranasal sumatriptan freebase with 100% of the particles <15 µm produced a Tmax of 7.5 minutes, a Cmax of 612 ng/ml, a T½ of 119 minutes and an AUC of 1827 ng:min/ml. Intranasal sumatriptan freebase with 50% of the particles <15 µm and 50% of the particles 38 µm-100 µm produced a Tmax of 7.6 minutes, a Cmax of 373 ng/ml, a T½ of 119 minutes and an AUC of 1827 ng:min/ml.

Figure 7:
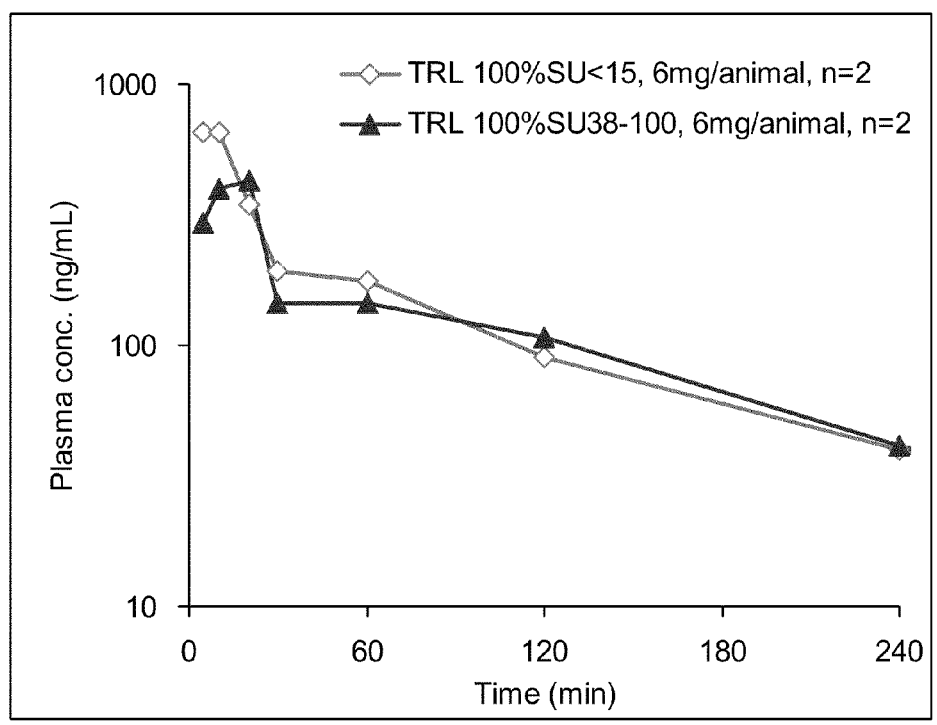
FIG. 7 illustrates the pharmacokinetic profiles of intranasally administered sumatriptan succinate formulations that differ only in their particle size distribution range.

Sumatriptan Pharmacokinetics—Comparison Between Intranasal Dry Powder Formulations: Effect of Succinate Particle Size on Pharmacokinetics The pharmacokinetics of sumatriptan dry powder formulations were studied in two groups of rhesus monkeys. One group, n=2, was administered intranasal sumatriptan succinate with a particle size of <15 µm. Administered dose was 6 mg/animal. A second group, n=2, was administered intranasal sumatriptan succinate with a particle size of 38 µm-100 µm. Administered dose was 6 mg/animal. Blood was obtained at 5, 10, 20, 30, 60, 120, and 240 minutes post-administration. The concentration of plasma sumatriptan was determined for both groups and then the data was processed to calculate the pharmacokinetic parameters and to construct a graph of the plasma concentration versus time curves (FIG. 7). Intranasal sumatriptan succinate with a particle size of <15 µm produced a Tmax of 7.5 minutes, a Cmax of 696 ng/ml, a T½ of 114, and an AUC of 2632 ng:min/ml. Intranasal sumatriptan succinate with particle size of 38 µm-100 µm produced a Tmax of 15 minutes, a Cmax of 426 ng/ml, a T½ of 119 minutes and an AUC of 39863 ng:min/ml.

There was no significant difference between the pharmacokinetics of the two groups because the difference in particle size does not significantly influence the dissolution rate of the succinate.

Figure 8:
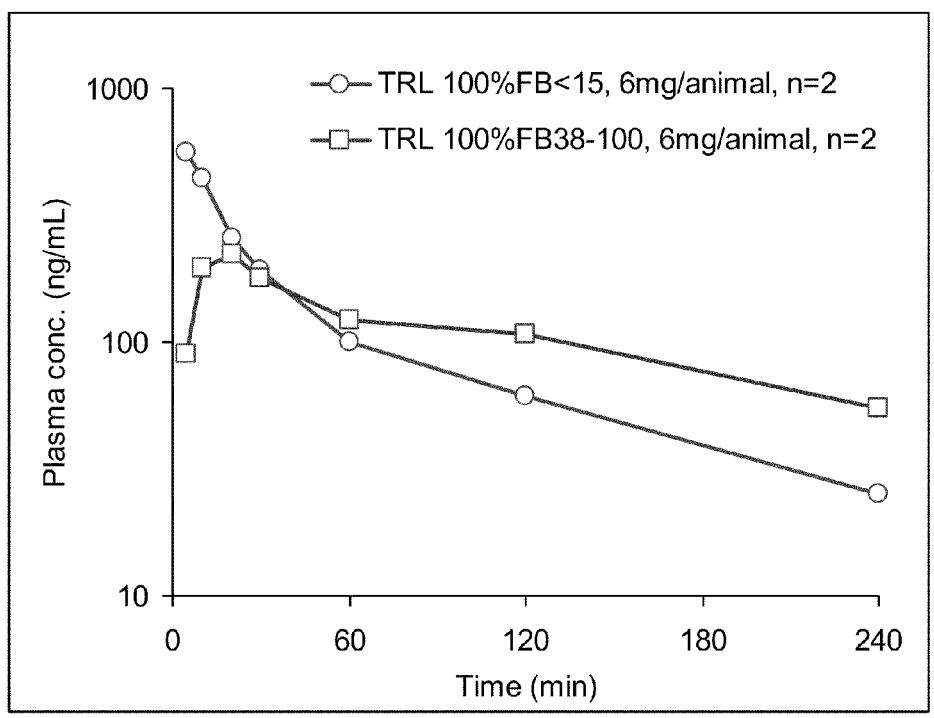
FIG. 8 illustrates the pharmacokinetic profiles of intranasally administered sumatriptan freebase formulations that differ only in their particle size distribution range.

Sumatriptan Pharmacokinetics—Comparison Between Intranasal Dry Powder Formulations: Effect of Freebase Particle Size on Pharmacokinetics The pharmacokinetics of sumatriptan dry powder formulations were studied in two groups of rhesus monkeys. One group, n=2, was administered intranasal sumatriptan freebase with a particle size of <15 µm. Administered dose was 6 mg/animal. A second group, n=2, was administered intranasal sumatriptan freebase with a particle size of 38 µm-100 µm. Administered dose was 6 mg/animal. Blood was obtained at 5, 10, 20, 30, 60, 120, and 240 minutes post-administration. The concentration of plasma sumatriptan was determined for both groups and then the data was processed to calculate the pharmacokinetic parameters and to construct a graph of the plasma concentration versus time curves (FIG. 8). Intranasal sumatriptan freebase with a particle size of <15 µm produced a Tmax of 7.5 minutes, a Cmax of 612 ng/ml, a T½ of 119, and an AUC of 1827 ng:min/ml. Intranasal sumatriptan freebase with particle size of 38 µm-100 µm produced a Tmax of 7.5 minutes, a Cmax of 345 ng/ml, a T½ of 104 minutes and an AUC of 2865 ng:min/ml.

Figure 9:
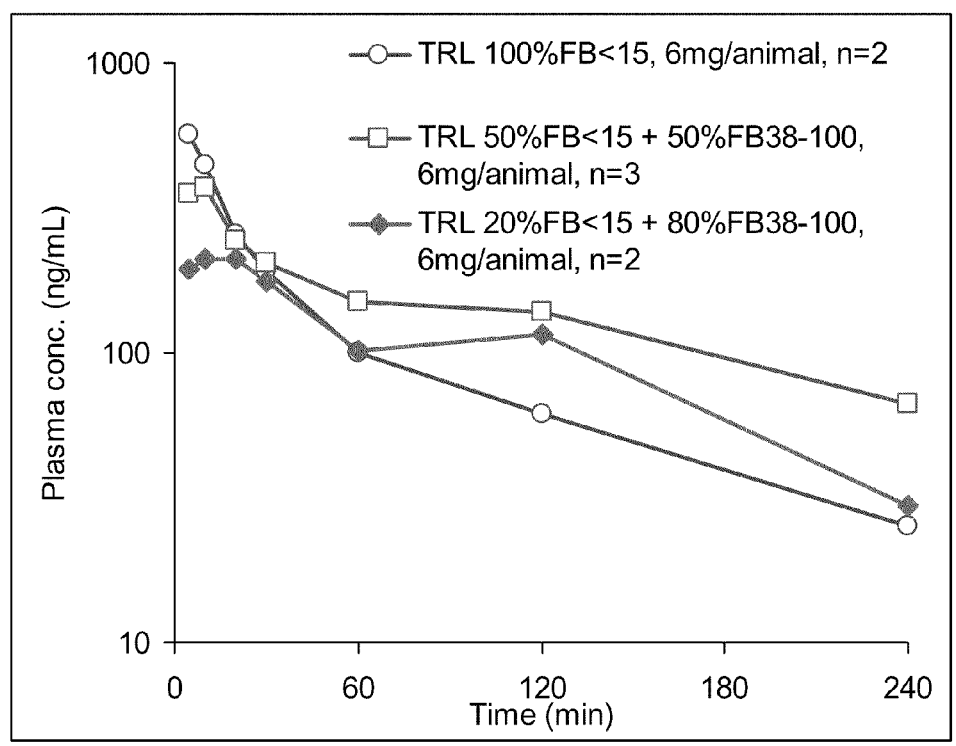
FIG. 9 illustrates the pharmacokinetic profiles of intranasally administered sumatriptan freebase formulations that differ only in their particle size distribution range.

Sumatriptan Pharmacokinetics—Comparison Between Intranasal Dry Powder Formulations: Effect of Mixtures of Different Size Freebase Particles on Pharmacokinetics The pharmacokinetics of sumatriptan dry powder formulations were studied in three groups of rhesus monkeys. One group, n=2, was administered intranasal sumatriptan freebase with a particle size of <15 µm. Administered dose was 6 mg/animal. A second group, n=3, was administered intranasal sumatriptan freebase as a mixture of 50% of the particles <15 µm and 50% of the particles in the range of 38 µm-100 µm. Administered dose was 6 mg/animal. A third group, n=2, was administered intranasal sumatriptan freebase as mixture of 20% of the particles <15 µm and 80% of the particles in the range of 38 µm-100 µm. Blood was obtained at 5, 10, 20, 30, 60, 120, and 240 minutes post-administration. The concentration of plasma sumatriptan was determined for all groups and then the data was processed to calculate the pharmacokinetic parameters and to construct a graph of the plasma concentration versus time curves (FIG. 9). Intranasal sumatriptan freebase with a particle size of <15 µm produced a Tmax of 7.5 minutes, a Cmax of 612 ng/ml, a T½ of 119, and an AUC of 1827 ng:min/ml. Intranasal sumatriptan freebase with a mixture of 50% of the particles <15 µm and 50% of the particles in the range of 38 µm-100 µm produced a Tmax of 7.5 minutes, a Cmax of 345 ng/ml, a T½ of 104 minutes and an AUC of 2865 ng:min/ml. Intranasal sumatriptan freebase with a mixture of 20% of the particles <15 µm and 80% of the particles in the range of 38 µm-100 µm produced a Tmax of 7.5 minutes, a Cmax of 345 ng/ml, a T½ of 104 minutes and an AUC of 2865 ng:min/ml.

As the percentage of particles in the range of 38 µm-100 µm increased, the observed Cmax decreased.

Figure 10:
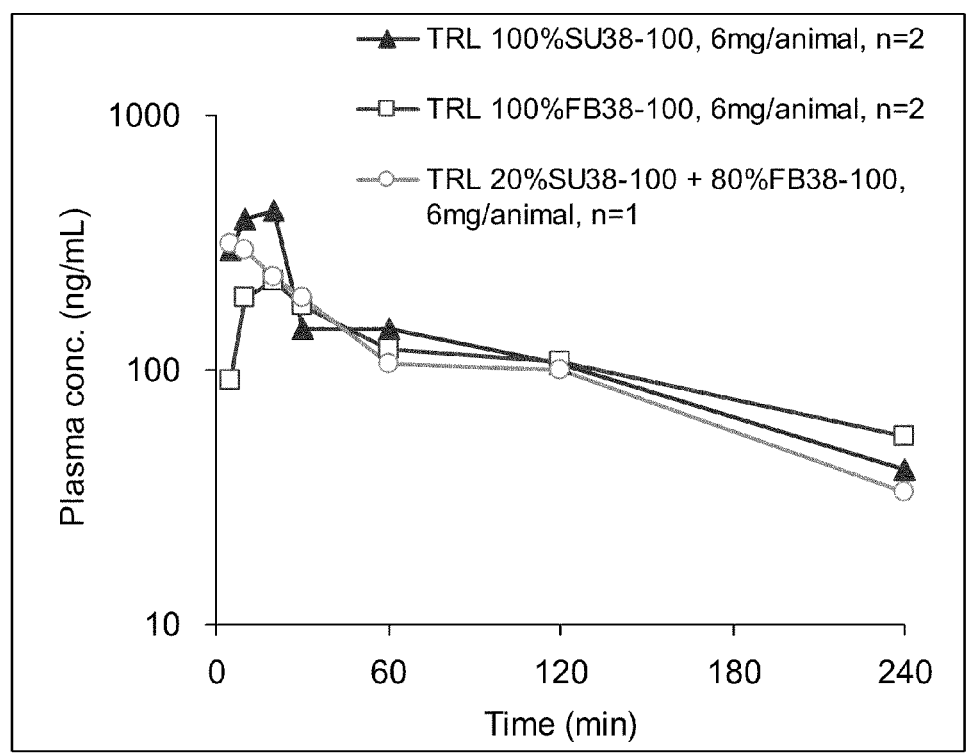
FIG. 10 illustrates the pharmacokinetic profiles of intranasally administered sumatriptan formulations that have the same particle size distribution range, but differ in the ratio of succinate to freebase.

Sumatriptan Pharmacokinetics—Comparison Between Intranasal Dry Powder Formulations: Effect of Mixtures Succinate and Freebase Particles of the Same Size on Pharmacokinetics The pharmacokinetics of sumatriptan dry powder formulations were studied in three groups of rhesus monkeys. One group, n=2, was administered intranasal sumatriptan succinate with a particle size 38 µm-100 µm. Administered dose was 6 mg/animal. A second group, n=2, was administered intranasal sumatriptan freebase with a particle size of 38 µm-100 µm. Administered dose was 6 mg/animal. A third group, n=1, was administered intranasal sumatriptan as a mixture of 20% succinate with a particle size of 38 µm-100 µm and 80% freebase with a particle size of 38 µm-100 µm. Blood was obtained at 5, 10, 20, 30, 60, 120, and 240 minutes post-administration. The concentration of plasma sumatriptan was determined for all groups and then the data was processed to calculate the pharmacokinetic parameters and to construct a graph of the plasma concentration versus time curves (FIG. 10). Intranasal sumatriptan succinate produced a Tmax of 7.5 minutes, a Cmax of 612 ng/ml, a T½ of 119, and an AUC of 1827 ng:min/ml. Intranasal sumatriptan freebase produced a Tmax of 7.5 minutes, a Cmax of 362 ng/ml, a T½ of 178 minutes and an AUC of 2287 ng:min/ml. Intranasal sumatriptan with a mixture of 20% succinate and 80% freebase produced a Tmax of 7.5 minutes, a Cmax of 345 ng/ml, a T½ of 104 minutes and an AUC of 2865 ng:min/ml.

Figure 11:
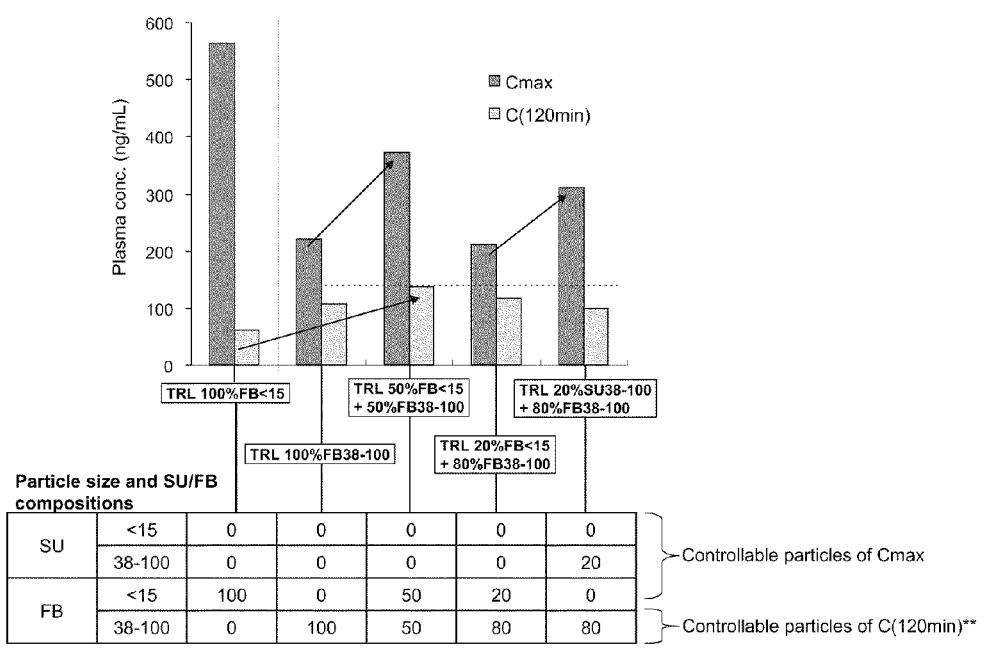
FIG. 11 represents a summary of the effects of particle size and chemical form (salt/freebase) on Cmax and $C_{120}$.

Summary of Influence of Particle Size and Salt/Freebase Form on Nasal Sumatriptan Absorption Among the formulations tested that contained freebase, the formulation with 100% freebase with particles with a particle size of <15 µm had the highest Cmax. This formulation's Cmax was comparable to that obtained with a formulation with 100% succinate with particles that are <15 µm. As the size of the freebase particles increase, the Cmax decreases (FIG. 11).

Example 2

Zolmitriptan Studies (Monkey Studies)

Figure 12:
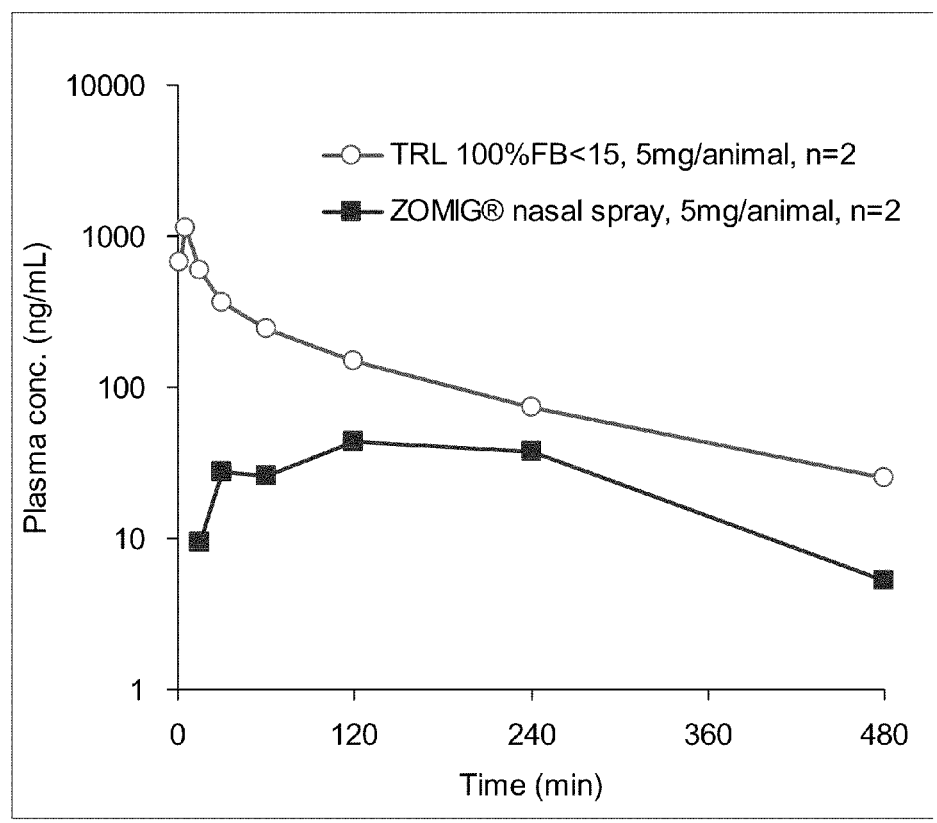
FIG. 12 illustrates the pharmacokinetic profiles of intranasally administered zolmitriptan formulations.

Zolmitriptan Pharmacokinetics—Comparison Between Liquid Nasal Spray and an Intranasal Dry Powder Comprising Freebase Zolmitriptan The pharmacokinetics of a zolmitriptan liquid nasal spray and a dry powder formulation were studied in two groups of rhesus monkeys. One group, n=2, was administered a nasal spray of zolmitriptan (Zomig®, 5 mg/100 µl in an aqueous buffered solution). A second, n=2, was administered intranasal zolmitriptan freebase with a particle size of <15 µm. The administered dose was 5 mg/animal. Blood was obtained at 10, 20, 30, 60, 120, 240 and 480 minutes post-administration (Zomig) or 5, 10, 20, 30, 60, 120, 240 and 480 minutes post-administration (dry powder). The concentration of plasma zolmitriptan was determined for both groups and then the data was processed to calculate the pharmacokinetic parameters for the administration groups and to construct a graph of the plasma concentration versus time curves (FIG. 12). The nasal spray produced a Tmax of 120 minutes, a Cmax of ng/ml, a T½ of, and an AUC of ng:min/ml. Intranasal zolmitriptan freebase with a particle size of <15 µm produced a Tmax of 10 minutes, a Cmax of ng/ml, a T½ of, and an AUC of ng:min/ml.

The freebase zolmitriptan dry powder had a significantly increased Cmax and BA compared with the liquid spray.

Figure 13:
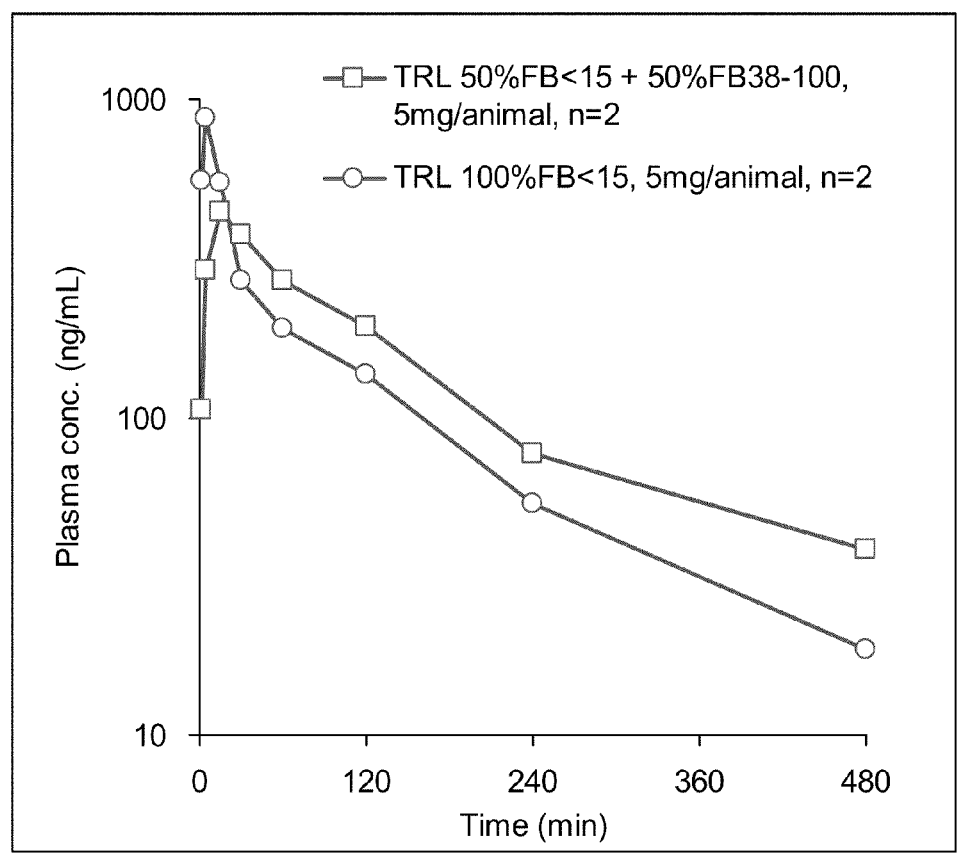
FIG. 13 illustrates the pharmacokinetic profiles of intranasally administered zolmitriptan freebase formulations that differ only in their particle size distribution range.

Zolmitriptan Pharmacokinetics—Comparison Between Intranasal Dry Powder Formulations: Effect of Mixtures of Different Size Freebase Particles on Pharmacokinetics The pharmacokinetics of zolmitriptan dry powder formulations were studied in two groups of rhesus monkeys. One group, n=2, was administered intranasal zolmitriptan freebase with a particle size of <15 µm. Administered dose was 5 mg/animal. A second group, n=2, was administered intranasal zolmitriptan freebase as a mixture of 50% freebase with a particle size of <15 µm and 50% freebase with a particle size of 38 µm-100 µm. Administered dose was 5 mg/animal. Blood was obtained at 5, 10, 20, 30, 60, 120, 240 and 480 minutes post-administration. The concentration of plasma zolmitriptan was determined for both groups and then the data was processed to calculate the pharmacokinetic parameters for the administration groups and to construct a graph of the plasma concentration versus time curves (FIG. 13). Intranasal zolmitriptan freebase with a particle size of <15 µm produced a Tmax of 10 minutes, a Cmax of ng/ml, a T½ of, and an AUC of ng:min/ml. Intranasal zolmitriptan freebase with 50% of the particles <15 µm and 50% of the particles 38 µm-100 µm produced a Tmax of 20 minutes, a Cmax of ng/ml, a T½ of minutes and an AUC of ng:min/ml.

The inclusion of larger size freebase particles lowers the Cmax and increases the BA.

Example 3

Taste Assay

This assay is intended to show that dry powder freebase formulations and dry powder mixtures of a salt and freebase have a much reduced unpleasant taste compared to a dry powder or liquid formulation of an equivalent quantity of formulations comprising the salt form alone.

Volunteers are identified and screened for inclusion and exclusion parameters of the study such as age, health, medication usage, alcohol consumption, pregnancy, smoking, allergies, dental hygiene, and impaired tastes perception. After receiving information about the study procedure, drug toxicity and risks involved, informed consent is obtained.

Volunteers are trained to understand the correct conduction of taste assessments and to ignore their personal taste preferences. Training sessions include instruction in the sample application method, the tasting of samples and sample scales, how to rank intensity, and the correct expectoration of samples. Volunteers are required to pass a basic sensory training test before becoming taste evaluators.

Standard solutions are freshly prepared with deionized water for taste assessments. The four basic tastes of sweet, salty, sour and bitter are evaluated using solutions of sucrose, NaCl, tartaric acid and quinine, respectively. Caffeine can also be used for bitterness. Standard dilutions are made for each basic taste. For quinine, the hydrochloride in concentrations of 0.01 mM, 0.03 mM, 0.10 mM, 0.30 mM, and 1.00 mM are used and correlated with a ranking of bitterness scores from 0, 1, 2, 3, and 4. (Ishizaka et al., 2004, Nakamura et al., 2003, Ogawa et al., 2004, Uchida et al., 2001). All solutions are provided at room temperature. Deionized water is used as a blank stimulus and a rinsing agent.

Dry powder standards of the salt forms of drugs are prepared, if desired, using a set formulation recipe that varies just by the quantity of drug present. Optionally, the formulation is an intranasal formulation. Typically, the quantity of drug present varies by 5-fold between samples. For example, with the drug granisetron, the range across four doses is 0.01 mg, 0.05 mg, 0.25 mg, and 1.25 mg, but any multiple or progression between samples can be used. Additionally, before comparing dry powder test formulations, the dry powder standards can be compared against the liquid standards, particular the bitterness standards, in order to correlate or titrate the given quantity of a drug in salt form that objectively produces the same degree of sensation, for example bitterness, as a standardized liquid formulation. A dry powder formulation that is devoid of the test drug serves as a blank.

Dry powder test formulations of freebase and salt mixtures are made using a set formulation recipe that will vary the ratio of freebase to salt form of the test drug while holding constant the total freebase equivalent weight of the drug. One test formulation contains only freebase.

Volunteers are required to avoid strongly flavored food on testing day. They are also required not to eat anything within an hour of testing and to refrain from taking any other food or drink until the end of the test. Prior to testing, volunteers rinse and expectorate several times with deionized water. They are also be required to rinse between samples. If needed, salty crackers are provided to help neutralize residual taste from the previous sample. Volunteers are refamiliarized with the taste standards by placing small amounts, 2-5 ml, of the standard solutions on the volunteers' tongues using disposable pipettes. The samples are held in the volunteers' mouths for a standard period of time. The taste standards are applied in a concentration increasing manner. During refamiliarization, test subjects are told of the taste's sensation (sweet, salty, sour and bitter) and intensity (0, 1, 2, 3, and 4). After refamiliarization, the testing of the dry powder formulations commences.

The dry powder formulations are applied to the tongue of the volunteers using a small spatula to provide a constant volume of powder. The dry powders are placed on the outer half of the tongue. Volunteers taste the dry powder formulations in a random order. After an appropriate time in their mouths, the volunteers are asked to rate the taste qualities and intensity to that of the standard solutions and select the standard solution having a taste equivalent to the powder formulation. (Ishizaka et al., 2004; Katsuragi et al., 1997). To confirm the rating, volunteers can ask to receive a sample of the liquid taste standard that they believe most closely corresponds. After rinsing their mouths and if needed, eating salty crackers to neutralize the taste of the previous test sample, a new dry powder sample are provided for testing.

Test formulations with the same rating as a standard are classified as equivalent. Test formulations with a rating that is one unit lower than a dry powder standard are classified as having a reduced taste, while those with a rating that is two units lower are classified as having a much reduced taste. Test formulations that have a rating that is three units lower than a standard are classified as substantially tasteless. Test formulations without a trace of the assayed test are classified as tasteless.

For odiferous samples, nose-clips are provided to the volunteers to eliminate olfactory input while rating. Volunteers can also be questioned about aftertaste, astringency and numbness following dry powder administration.

If desired, the test formulations are directly compared to the dry powder standards. Test formulations with the same rating as a standard are classified as equivalent. Test formulations with a rating that is one unit lower than a dry powder standard are classified as having a reduced taste, while those with a rating that is two units lower are classified as having a much reduced taste. Test formulations with a rating that is three units lower than a dry powder standard are classified as substantially tasteless. Test formulations without a trace of the assayed test are classified as tasteless.

As an alternate method to compare the taste perception of formulations, the dry powder formulations are tested in relation to one another without reference to the taste of the liquid standards. A dry powder formulation comprising only the salt form of the drug is compared with the a formulation comprising only the freebase or a freebase and salt mixture formulations. All test formulations have the equivalent weight of the drug when measured as the freebase. An equal volume of each formulation is put on the tongues of the volunteers and after an appropriate time, they are asked to record their perceptions. After all the samples of one freebase drug equivalent weight are tested, the volunteers are asked to rank the samples relative to each other with 0 having the least taste and 4 the most taste. Taste can be further defined based on classically defined tastes such as bitterness or saltiness. Alternatively, taste rating is based on the degree of objectionableness. If desired, volunteers are asked to describe the taste of each sample.

Three dry powder formulations each containing 1.25 mg freebase equivalent weight of granisetron are prepared. One sample contains granisetron as the hydrochloride salt. The second sample contains granisetron as the freebase. The third sample contains granisetron as a mixture of 20% granisetron hydrochloride salt and 80% granisetron freebase.

Volunteers are sequentially administered 0.5 cm³ of each powder formulation on their tongue in a random order. After a period of 1 minute following administration, they are asked to record their subjective sensory experiences. After 2 minutes, the volunteers clear their mouths by expectorating the contents and rinse three times with deionized water. After 5 minutes and again after 10 minutes, they are asked to record the presence and strength of any aftertaste.

The volunteers then eat a salty cracker and rinse their mouths will deionized water prior to being administered the next test sample. After all samples are tested, the volunteers are asked to rank the test samples two ways: 1) from least to strongest taste and 2) from least to most objectionable taste.

Volunteers find that the granisetron hydrochloride tastes the strongest, being quite bitter and objectionable. The mixture of 20% granisetron hydrochloride and 80% granisetron freebase is found to have a moderate taste, bitter, but not overtly objectionable. The granisetron freebase formulation is found to have almost no perceptible taste. The ranking of the three samples for the strength of the perceived taste is granisetron freebase<20% granisetron hydrochloride and 80% granisetron freebase<<granisetron hydrochloride. Similarly, the perceived objectionableness is granisetron freebase<20% granisetron hydrochloride and 80% granisetron freebase<<granisetron hydrochloride.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A composition comprising a therapeutic agent, wherein at least some of the therapeutic agent is present in a freebase form, and the therapeutic agent consists of two particle size distribution ranges, the first being less than 20 microns and the second being from about 38 microns to about 100 microns.

2. The composition of claim 1, comprising a salt form of the therapeutic agent.

3. The composition of claim 1, further comprising a carrier.

4. The composition of claim 3, wherein the carrier is substantially water-insoluble.

5. The composition of claim 4, wherein the carrier is selected from the group consisting of a polysaccharide, a sugar, a salt, a polymer, a gum, a protein, and a carbohydrate.

6. The composition of claim 4, wherein the carrier is selected from the group consisting of polysaccharides, polymers, carbohydrates, salts, and proteins.

7. The composition of claim 3, wherein the carrier is a bioadhesive.

8. The composition of claim 5, wherein the carrier is the polysaccharide, and wherein the polysaccharide comprises native, derivatized, modified forms, or any combination thereof, of the polysaccharide.

9. The composition of claim 5, wherein the carrier is the polysaccharide, and wherein the polysaccharide is a starch.

10. The composition of claim 9, wherein the starch is selected from the group consisting of hydroxypropyl starch, carboxymethyl starch, cross-linked starch, amylose, amylopectin, and pectin.

11. The composition of claim 5, wherein the carrier is the sugar, and wherein the sugar comprises fructose, galactose, glucose, lactitol, lactose, maltitol, maltose, mannitol, melezitose, myoinositol, palatinite, raffinose, stachyose, sucrose, trehalose, xylitol, hydrates thereof, or combinations thereof.

12. The composition of claim 5, wherein the carrier is the polysaccharide, and wherein the polysaccharide is a cellulose.

13. The composition of claim 12, wherein the cellulose is selected from the group consisting of crystalline cellulose, cellulose, α-cellulose, methylcellulose, hydroxypropyl cellulose, carboxymethyl cellulose, and hydroxypropyl methyl cellulose.

14. The composition of claim 13, wherein the cellulose is the crystalline cellulose, and wherein the crystalline cellulose has a particle diameter range from about 5 to 250 μm.

15. The composition of claim 13, wherein the cellulose is the crystalline cellulose, and wherein the crystalline cellulose has a bulk density of less than 0.60 g/cm$^3$.

16. The composition of claim 13, wherein the cellulose is the crystalline cellulose, and wherein the crystalline cellulose has an average degree of polymerization of about 20 to about 250.

17. The composition of claim 1, further comprising an additional therapeutic agent.

18. The composition of claim 17, wherein the additional therapeutic agent is a salt of the additional therapeutic agent, a freebase of the additional therapeutic agent, or a mixture thereof.

19. The composition of claim 1, further comprising a fluidizer, lubricant, surfactant, acidifying agent, alkalizing agent, antimicrobial preservative, antioxidant, buffering agent, chelating agent, complexing agent, solubilizing agent, humectant, or wetting agent.

20. The composition of claim 19, comprising the fluidizer, wherein the fluidizer comprises tribasic calcium phosphate.

21. The composition of claim 2, wherein a ratio of the salt form to the freebase form of the therapeutic agent is equal to or greater than 1:10 on a molar basis.

22. The composition of claim 1, wherein following intranasal administration to a human, a taste profile is substantially less bitter or objectionable than a taste profile of a corresponding composition wherein the therapeutic agent is present as a salt form at the same molar quantity.

23. A unit dosage form containing a composition as described in claim 1.

24. The unit dosage form of claim 23, in the form of a capsule.

25. The unit dosage form of claim 1, in the form of an intranasal administration device.

26. The composition of claim 1, wherein a maximal blood therapeutic concentration (Cmax) of the therapeutic agent in the composition is at least 100% of a Cmax of a corresponding therapeutic agent present at a 100% salt form when administered to a primate.

27. The composition of claim 26, wherein the therapeutic agent has a Cmax that is at least 110% of a Cmax of a corresponding therapeutic agent present at a 100% salt form when administered to a primate.

28. The composition of claim 1, wherein a time to reach a blood concentration of ½ of Cmax ($T_{1/2}$) of the therapeutic agent in the composition is at least 100% of a $T_{1/2}$ of a corresponding therapeutic agent present at a 100% salt form when administered to a primate.

29. The composition of claim 28, wherein the therapeutic agent has a $T_{1/2}$ that is at least 110% of a $T_{1/2}$ of a corresponding therapeutic agent present at a 100% salt form when administered to a primate.

30. The composition of claim 1, wherein a time to reach a blood concentration Cmax (Tmax) of the therapeutic agent in the composition is at least 100% of a Tmax of a corresponding therapeutic agent present at a 100% salt form when administered to a primate.

31. The composition of claim 30, wherein the therapeutic agent has a Tmax that is at least 110% of a corresponding therapeutic agent present at a 100% salt form when administered to a primate.

32. The composition of claim 1, wherein a bioavailability (BA) of the therapeutic agent in the composition is at least 100% of a BA of a corresponding therapeutic agent present at a 100% salt form when administered to a primate.

33. The composition of claim 32, wherein the therapeutic agent has a BA that at least 110% compared to a BA of a corresponding therapeutic agent present at 100% salt form when administered to a primate.

34. The composition of claim 26, wherein a time to reach a blood concentration of ½ of Cmax ($T_{1/2}$) of the therapeutic agent in the composition is at least 100% of a $T_{1/2}$ of a corresponding therapeutic agent present at a 100% salt form when administered to a primate.

35. The composition of claim 34, wherein a time to reach a blood concentration Cmax (Tmax) of the therapeutic agent in the composition is at least 100% of a Tmax of a corresponding therapeutic agent present at a 100% salt form when administered to a primate.

36. The composition of claim 35, wherein a bioavailability (BA) of the therapeutic agent in the composition is at least 100% of a BA of a corresponding therapeutic agent present at a 100% salt form when administered to a primate.

37. The composition of claim 1, which is for intranasal administration to a human.

38. The composition of claim 1, wherein the therapeutic agent is a small molecule.

39. The composition of claim 1, wherein the therapeutic agent is selected from the group consisting of: antibiotics, antifungal agents, sulfa drugs, antituberculosis drugs, antimicrobial agents, antiviral agents, hypnotic sedatives, antiepileptic agents, narcotic analgesics, nonnarcotic analgesics, sedative drugs, psychotherapeutic agents, and muscle relaxants.

40. The composition of claim 1, wherein the therapeutic agent is selected from the group consisting of: antiallergic agents, anti-rheumatic drugs, cardiotonic drugs, antiarrhythmic agents, antihypertensive agents, diuretic agents, coronary vasodilators, antidementia drugs, brain activators, brain circulation ameliorating agents, antiparkinsonian agents, antihyperlipidemic drugs, antiulcer drugs, antiemetic agents, obesity drugs, diabetic drugs, hemostatic drugs, antithrombotic agents, migraine drugs, antitussive drugs, expectorants, respiratory stimulants, asthma drugs, and antianaphylactic agents.

41. The composition of claim 1, wherein the therapeutic agent is selected from the group consisting of: antidiarrheal drugs, nonsteroidal antiinflammatory agents, antipodagrics, agents for treating urinary diseases, drugs for improving sexual function, agents for the uterus, steroids, prostaglandins, vitamins, histamines, antidotes, agents for treating heavy metal toxification, quit smoking agents, and antitumor agents.

42. The composition of claim 1, wherein the therapeutic agent is an antiemetic agent.

43. The composition of claim 42, wherein the antiemetic agent is granisetron, ondansetron, tropisetron, palonosetron, indisetron, domperidone, or metoclopramide.

44. The composition of claim 1, wherein the therapeutic agent is an antimigraine agent.

45. The composition of claim 44, wherein the antimigraine agent is sumatriptan, zolmitriptan, rizatriptan, naratriptan, ergotamine, or dihydroergotamine.

46. The composition of claim 1, wherein a Tmax of the therapeutic agent is at least 100% of a Tmax of a corresponding therapeutic agent present at a 100% salt form when administered to a primate.

47. The composition of claim 2, wherein the composition comprises sumatriptan succinate.

48. The composition of claim 2, wherein a ratio of the salt form to the freebase form of the therapeutic agent is equal to or greater than 1:4 on a molar basis.

* * * * *